US012564622B2

(12) United States Patent
Vogelstein et al.

(10) Patent No.: US 12,564,622 B2
(45) Date of Patent: \*Mar. 3, 2026

(54) PREVENTING CYTOKINE RELEASE SYNDROME

(71) Applicant: The Johns Hopkins University, Baltimore, MD (US)

(72) Inventors: Bert Vogelstein, Baltimore, MD (US); Kenneth W. Kinzler, Baltimore, MD (US); Nickolas Papadopoulos, Towson, MD (US); Shibin Zhou, Owings Mills, MD (US); Verena Staedtke, Baltimore, MD (US); Renyuan Bai, Baltimore, MD (US); Gregory J. Riggins, White Hall, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/078,645

(22) Filed: Dec. 9, 2022

(65) Prior Publication Data

US 2023/0310549 A1 Oct. 5, 2023

Related U.S. Application Data

(63) Continuation of application No. 16/957,970, filed as application No. PCT/US2018/064969 on Dec. 11, 2018, now Pat. No. 11,628,204.

(60) Provisional application No. 62/610,620, filed on Dec. 27, 2017.

(51) Int. Cl.

| | |
|---|---|
| *A61K 38/22* | (2006.01) |
| *A61K 31/137* | (2006.01) |
| *A61K 31/195* | (2006.01) |
| *A61K 31/198* | (2006.01) |
| *A61K 31/517* | (2006.01) |
| *A61P 19/02* | (2006.01) |
| *A61P 37/00* | (2006.01) |
| *A61P 37/06* | (2006.01) |

(52) U.S. Cl.
CPC ........ *A61K 38/2242* (2013.01); *A61K 31/137* (2013.01); *A61K 31/198* (2013.01); *A61K 31/517* (2013.01); *A61P 37/06* (2018.01)

(58) Field of Classification Search
CPC .......... A61K 2039/54; A61K 2039/545; A61K 2300/00; A61K 31/137; A61K 31/195; A61K 31/198; A61K 31/517; A61K 38/2242; A61K 39/3955; A61K 38/22; A61P 19/02; A61P 37/00; A61P 37/06; C07K 2319/03
See application file for complete search history.

(56) References Cited

U.S. PATENT DOCUMENTS 6,932,969 B1    8/2005   Bourel et al.

OTHER PUBLICATIONS

Hamaker et al., Chapter 41, "Adrenal Disorders," Pharmacology and Therapeutics, 2009, 623-640. (Year: 2009).*
Wang et al., "Recognition and management of phaeochromocytoma and paraganglioma," Endocrinology, 2017, pp. 496-501. (Year: 2017).*
Cytokine Release Syndrome from Cleveland Clinic, https://clevelandclinic.org/health/diseases/22700-cytokine-release-syndrome, pp. 1-11. Accessed Apr. 2, 2025. (Year: 2025).*
Parazzoli et al., "Inflammation-based Scores in Patients With Pheochromocytoma," The Journal of Clinical Endocrinology & Metabolism, 2025, 110: e630-e640. (Year: 2025).*
CNIO, "The largest genomic study of rare cancer metastatic pheochromocytoma identifies patients at highest risk of metastasis and those who would respond to Immunotherapy," pp. 1-5. Feb. 28, 2023. (Year: 2023).*
Staedtke et al., "Disruption of a self-amplifying catecholamine loop reduces cytokine release syndrome," Nature, Dec. 13, 2018, 564: 273-277. (Year: 2018).*
Agrawal et al., "Bacteriolytic therapy can generate a potent immune response against experimental tumors", PNAS 101(42), 15172-15177, 2004.
Annane et al., "Effect of Treatment With Low Doses of Hydrocortisone and Fludrocortisone on Mortality in Patients With Septic Shock", JAMA 288(7): 862-871, 2002.
Anton et al., "Inhibition of catecholamine biosynthesis by carbidopa and metyrosine in neuroblastoma", Pediatr Pharmacol (New York), 3(2): 107-117, 1983 (abstract only).
Bai et al., "Effective treatment of diverse medulloblastoma models with mebendazole and its impact on tumor angiogenesis", Neuro-Oncology 17(4), 545-554, 2015.
Bao et al., "Expression of -AR Subtypes in T Lymphocytes and Role of the a-ARs in Mediating Modulation of T Cell Function", Neuroimmunomodulation, 14: 344-353, 2007.
Berahovich et al., "FLAG-tagged CD19-specific CAR-T cells eliminate CD19-bearing solid tumor cells in vitro and in vivo", Frontiersin Bioscience, Landmark, 22, 1644-1654, 2017.
Bettegowda et al., "The genome and transcriptomes of the antitumor agent Clostridium novyi-NT", Nature Biotechnology, 24(12): 1573-1580, 2006.
Burke et al., "BMS-345541 Is a Highly Selective Inhibitor of I B Kinase That Binds at an Allosteric Site of the Enzyme and Blocks NF-B-dependent Transcription in Mice", The Journal of Biological Chemistry, 278(3): 1450-1456, 2003.
Camell et al., "Inflammasome-driven catecholamine catabolismin macrophages blunts lipolysis in the aged", Nature, 550(7674): 119-123, 2017.
Chatenoud et al., "In vivo cell activation following OKT3 administration", Transplantation 49(4): 697-702, 1990.

(Continued)

*Primary Examiner* — Julie Ha
(74) *Attorney, Agent, or Firm* — Fish & Richardson P.C.

(57) ABSTRACT

Provided herein are methods and materials for preventing cytokine release syndrome (CRS). For example, methods and materials for using one or more catecholamine inhibitors to prevent a mammal from developing CRS are provided.

15 Claims, 67 Drawing Sheets

Specification includes a Sequence Listing.

(56)                     References Cited

OTHER PUBLICATIONS

Clausen et al., "Conditional gene targeting in macrophages and granulocytes using LysMcre mice", Transgenic Research 8: 265-277, 1999.

Corrodi et al., "Central Effects of an Inhibitor of Tyrosine Hydroxylation", Psychopharmacologia (Berl.) 10, 116-125, 1966.

Davila et al., "CD19 CAR-Targeted T Cells Induce Long-Term Remission and B Cell Aplasia in an Immunocompetent Mouse Model of B Cell Acute Lymphoblastic Leukemia", PLOS One 8(4): e61338, 14 pages, 2013.

Diaz Jr. et al., "Pharmacologic and Toxicologic Evaluation of C. novyi-NT Spores", Toxicological Sciences, 88(2): 562-575, 2005.

Engelman et al., "Inhibition of Catecholamine Biosynthesis in Man," Circulation Research, Jun. 1, 1966, 18(s6): 1-104-1109, abstract only enclosed. (Year: 1966).

Fagenholz et al., "Increasing United States Hospital Admissions for Acute Pancreatitis, 1988-2003", Ann Epidemiol., 17: 491-497, 2007.

Ferran et al., "Cytokine-related syndrome following injection of anti-CD3 monoclonal antibody: further evidence for transient in vivo T cell activation", Eur. J. Immunol., 20: 509-515, 1990.

Fitzgerald et al., "Cytokine Release Syndrome After Chimeric Antigen Receptor T Cell Therapy for Acute Lymphoblastic Leukemia", Crit Care Med., 45(2): e124-e131, 2017.

Flierl et al., "Phagocyte-derived catecholamines enhance acute inflammatory injury", Nature 449, 721-726, 2007.

Forbes, "Engineering the perfect (bacterial) cancer therapy", Nat Rev Cancer, 10(11): 785-794, 2010.

Frey et al., "Cytokine release syndrome with novel therapeutics for acute lymphoblastic leukemia", Hematology Am Soc Hematol Educ Program, (1): 567-572, 2016.

Giavridis et al., "CAR T cell-induced cytokine release syndrome is mediated by macrophages and abated by IL-1 blockade", Nat Med., 24(6): 731-738, 2018.

Gill et al., "Preclinical targeting of human acute myeloid leukemia and myeloablation using chimeric antigen receptor-modified T cells", Blood, 123(15): 2343-2354, 2014.

Green et al., "Alpha-methyltyrosine in the management of phaeochromocytoma", Thorax, 37: 632-633, 1982.

Grupp et al., "Chimeric Antigen Receptor-Modified T Cells for Acute Lymphoid Leukemia", N Engl J Med., 368(16): 1509-1518, 2013.

Guglielmi et al., "Efficacy and safety of otelixizumab use in new onset type 1 diabetes mellitus", Expert Opinion on Biological Therapy, 16: 6, 841-846, 2016.

Hansel et al., "The safety and side effects of monoclonal antibodies", Nature Reviews, Drug Discovery, 9, 325-338, 2010.

Hoffman et al., "Bacterial Therapy of Cancer, Methods and Protocols", Methods in Molecular Biology 1409, 195 pages, 2016.

International Preliminary Report on Patentability in Appl. No. PCT/US2018/064969, dated Mar. 14, 2019, 6 pages.

International Search Report and Written Opinion in International Application No. PCT/US2018/064969, dated Apr. 18, 2019, 13 pages.

Jackson et al., "Retinal Dopamine Mediates Multiple Dimensions of Light-Adapted Vision", The Journal of Neuroscience, 32(27): 9359-9368, 2012.

Jacobsohn et al., "Acute graft versus host disease", Orphanet Journal of Rare Diseases, 2: 35, 9 pages, 2007.

Johnson et al., "Catecholamines mediate stress-induced increases in peripheral and central inflammatory cytokines", Neuroscience 135, 1295-1307, 2005.

Johnson et al., "Driving gene-engineered T cell immunotherapy of cancer", Cell Research, 27: 38-58, 2017.

Kopf et al., "Averting inflammation by targeting the cytokine environment", Nature Reviews, Drug Discovery, 9: 703-718, 2010.

Kuehne et al., "ClosTron-mediated engineering of Clostridium", Bioengineered 3: 4, 247-254, 2012.

Lee et al., "Current concepts in the diagnosis and management of cytokine release syndrome", Blood, 124(2): 188-195, 2014.

Lee et al., "Retroviral Transduction of Murine Primary T Lymphocytes", Methods Mol Biol., 506: 83-96, 2009.

Lofton et al., "Atrial natriuretic peptide regulation of endothelial permeability is mediated by cGMP", Biochemical and Biophysical Research Communications, 172(2): 793-799, 1990.

Maude et al., "Chimeric Antigen Receptor T Cells for Sustained Remissions in Leukemia", N Engl J Med., 371: 1507-1517, 2016.

Maude et al., "Managing Cytokine Release Syndrome Associated With Novel T Cell-Engaging Therapies", Cancer J., 20(2): 119-122, 2014.

McDermott et al., "Characteristics and Costs of Potentially Preventable Inpatient Stays, 2017", Statistical Brief #259, 18 pages, 2020.

Medzhitov et al., "Origin and physiological roles of inflammation", Nature, 454: 428-435, 2008.

Metyrosine from https:/go-drugbank.conn, pp. 1-6. Accessed Feb. 8, 2022. (Year: 2022).

Mofidi et al., "Association between early systemic inflammatory response, severity of multiorgan dysfunction and death in acute pancreatitis", British Journal of Surgery, 93: 738-744, 2006.

Moreira-Rodrigues et al., "Low epinephrine levels and selective deficiency of β2-adrenoceptor vasodilation at birth.", Life Sciences 156:c1-6, 2016.

Nathan, "Points of control in inflammation", Nature 420: 846-852, 2002.

Neelapu et al., "Chimeric antigen receptor T-cell therapy—assessment and management of toxicities", Nat Rev Clin Oncol., 15(1): 47-62, 2018.

Niece et al., "Hemophagocytic Lymphohistiocytosis in Texas: Observations on Ethnicity and Race", Pediatr Blood Cancer, 54: 424-428, 2010.

Ninomiya et al., "Tumor indoleamine 2,3-dioxygenase (IDO) inhibits CD19-CAR T cells and is downregulated by lymphodepleting drugs", Blood, 125(25): 3905-3916, 2015.

Norelli et al., "Monocyte-derived IL-1 and IL-6 are differentially required for cytokine-release syndrome and neurotoxicity due to CAR T cells", Nature Medicine 24: 739-748, 2018.

Panelli et al., Forecasting the cytokine storm following systemic 2: 17, 14 pages, 2004.

Parker et al., "Antitumour actions of interferons: implications for cancer therapy", Nature Reviews, Cancer 16: 131-144, 2016.

Peters van Ton et al., "Precision Immunotherapy for Sepsis", Front. Immunol. 9: 1926, 10 pages, 2018.

Pheochromocytoma from https://www.nnayoclinic.org/diseases-conditions/pheochronnocytonna/diagnosis-treatnnent/, pp. 1-8, Accessed Feb. 8, 2022. (Year: 2022).

Qiao et al., "A Robust Approach to Enhance Tumor-selective Accumulation of Nanoparticles", Oncotarget, 2: 59-68, 2011.

Qiu et al., "Anti-Tumor Necrosis Factor Therapy is Associated with Improved Survival in Clinical Sepsis Trials: A Meta-analysis", Crit Care Med., 41(10): 18 pages, 2013.

Riedemann et al., "Protective Effects of IL-6 Blockade in Sepsis Are Linked to Reduced C5a Receptor Expression", J Immunol., 170: 503-507, 2003.

Rittirsch et al., "Harmful molecular mechanisms in sepsis", Nat Rev Immunol., 8(10): 776-787, 2008.

Rittirsch et al., "Immunodesign of experimental sepsis by cecal ligation and puncture", Nat Protoc., 4(1): 31-36, 2009.

Roberts et al., "Intratumoral injection of Clostridium novyi-NT spores induces antitumor responses", Sci Transl Med., 6(249): 27 pages, 2014.

Rommelfanger et al., "The Efficacy Versus Toxicity Profile of Combination Virotherapy and TLR Immunotherapy Highlights the Danger of Administering TLR Agonists to Oncolytic Virus-treated Mice", Tumor Clearance Through Activation of Multiple TLR Pathways, 21(2): 349-357, 2013.

Ruella et al., "Chimeric Antigen Receptor T cells for B Cell Neoplasms: Choose the Right CAR for You", Curr Hematol Malig Rep., 11: 368-384, 2016.

Sentman et al., "Mechanisms of Acute Toxicity in NKG2D Chimeric Antigen Receptor T Cell-Treated Mice", J Immunol 197: 4674-4685, 2016.

(56)                    References Cited

OTHER PUBLICATIONS

Sevmis et al., "OKT3 Treatment for Steroid-Resistant Acute Rejection in Kidney Transplantation", Transplantation Proceedings, 37, 3016-3018, 2005.

Shaked et al., "The orphan nuclear receptor Nr4a1 couples sympathetic and inflammatory cues in CNS-recruited macrophages to limit neuroinflammation", Nat Immunol., 16(12): 1228-1234, 2015.

Shimabukuro-Vornhagen et al., "Cytokine release syndrome", Journal for Immuno Therapy of Cancer, 6(56): 14 pages, 2018.

Sigola et al., "Adrenaline inhibits macrophage nitric oxide production through b1 and b2 adrenergic receptors", Immunology 100: 359-363, 2000.

Staedtke et al., "Clostridium novyi-NT in cancer therapy", Genes & Diseases, 3, 144e152: 144-152, 2016.

Suntharalingam et al., "Cytokine Storm in a Phase 1 Trial of the Anti-CD28 Monoclonal Antibody TGN1412", The New England Journal of Medicine, 355(10): 1018-1028, 2006.

Surbatovic et al., "Cytokine profile in severe grampositive and gram-negative abdominal sepsis", Scientific Reports 5:11355, 12 pages, 2015.

Teachey et al., "Identification of Predictive Biomarkers for Cytokine Release Syndrome after Chimeric Antigen Receptor T cell Therapy for Acute Lymphoblastic Leukemia", Cancer Discov., 6(6): 664-679, 2016.

Todd et al., "Gabapentin Inhibits Catecholamine Release from Adrenal Chromaffin Cells", Anesthesiology 116(5): 1013-1024, 2012.

Tomayko et al., "Determination of subcutaneous tumor size in athymic (nude) mice", Cancer Chemother Pharmacol., 24: 148-154, 1989.

Van der Poll et al., "The immunopathology of sepsis and potential therapeutic targets", Nature Reviews, Immunology 17: 407-420, 2017.

Vollmar, "The role of atrial natriuretic peptide in the immune system", Peptides 26, 1086-1094, 2005.

Weber et al., "Interleukin-3 amplifies acute inflammation and is a potential therapeutic target in sepsis", Science, 347(6227): 1260-1265, 2015.

Wiersinga et al., "Host innate immune responses to sepsis", Virulence 5(1): 36-44, 2014.

Wunderlich et al., "A xenograft model of macrophage activation syndrome amenable to anti-CD33 and anti-IL-6R treatment", JCI Insight, 1(15): e88181, 12 pages, 2016.

Wunderlich et al., "AML xenograft efficiency is significantly improved in NOD/SCID-IL2RG mice constitutively expressing human SCF, GM-CSF and IL-3", Leukemia 24: 1785-1788, 2010.

Zhang et al., "The Isolation and Characterization of Murine Macrophages", Curr Protoc Immunol., Chapter: Unit—14.1, 18 pages, 2008.

Zheng et al., "Donor pulmonary intravascular nonclassical monocytes recruit recipient neutrophils and mediate primary lung allograft dysfunction", Sci. Transl. Med. 9, eaal4508, 13 pages, 2017.

* cited by examiner

- C. *novyi*-NT (n=**)
- ANP-C. novyi-NT (n=88)   |***
- *C. novyi*-NT + ANP pump (n=12)
- Vector-C. novyi-NT (n=5)

■ Death

▨ Alive, partial tumor eradication

☐ Alive, complete tumor eradication freshly added Epinephrine without 24 hr Incubation

FIG. 13A                                    FIG. 13B

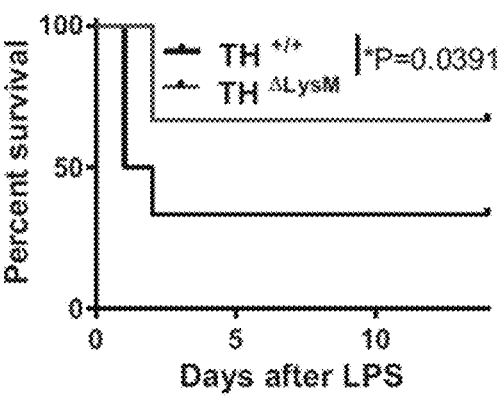
FIG. 20C
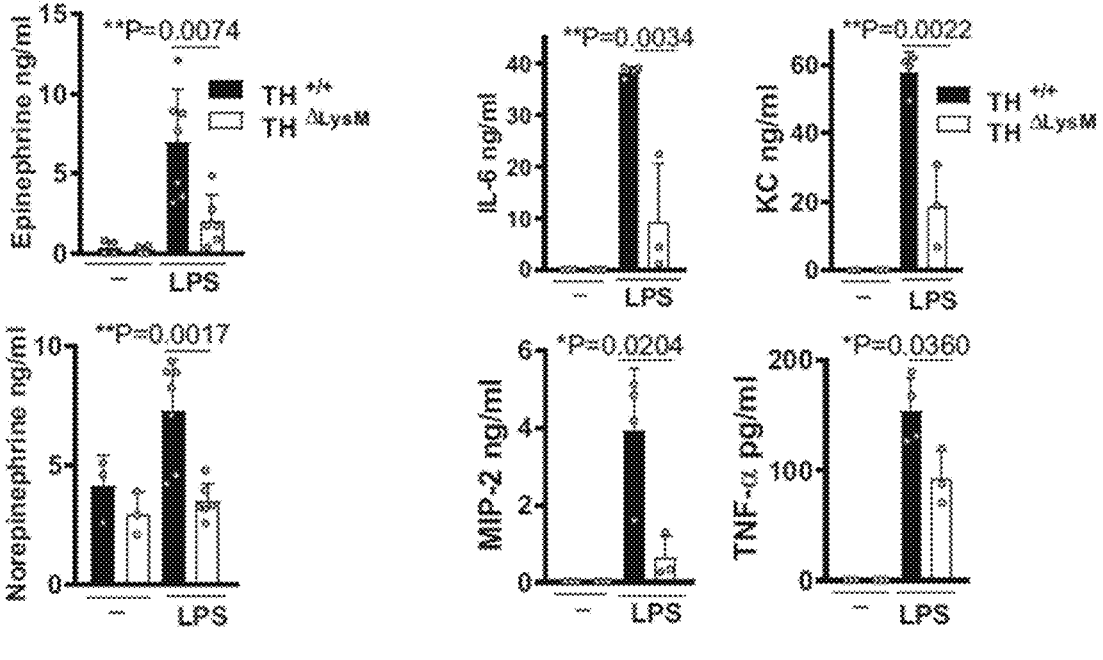
FIG. 20D                              FIG. 20E

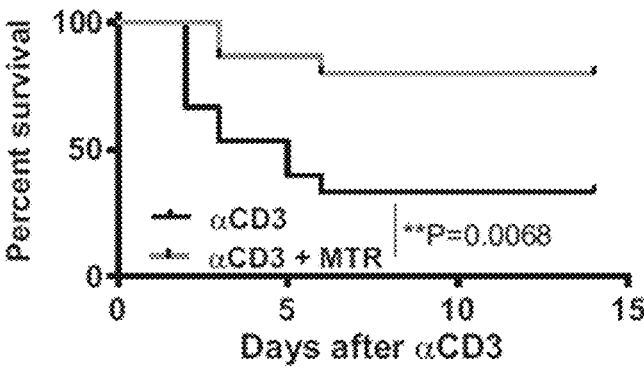
FIG. 25C
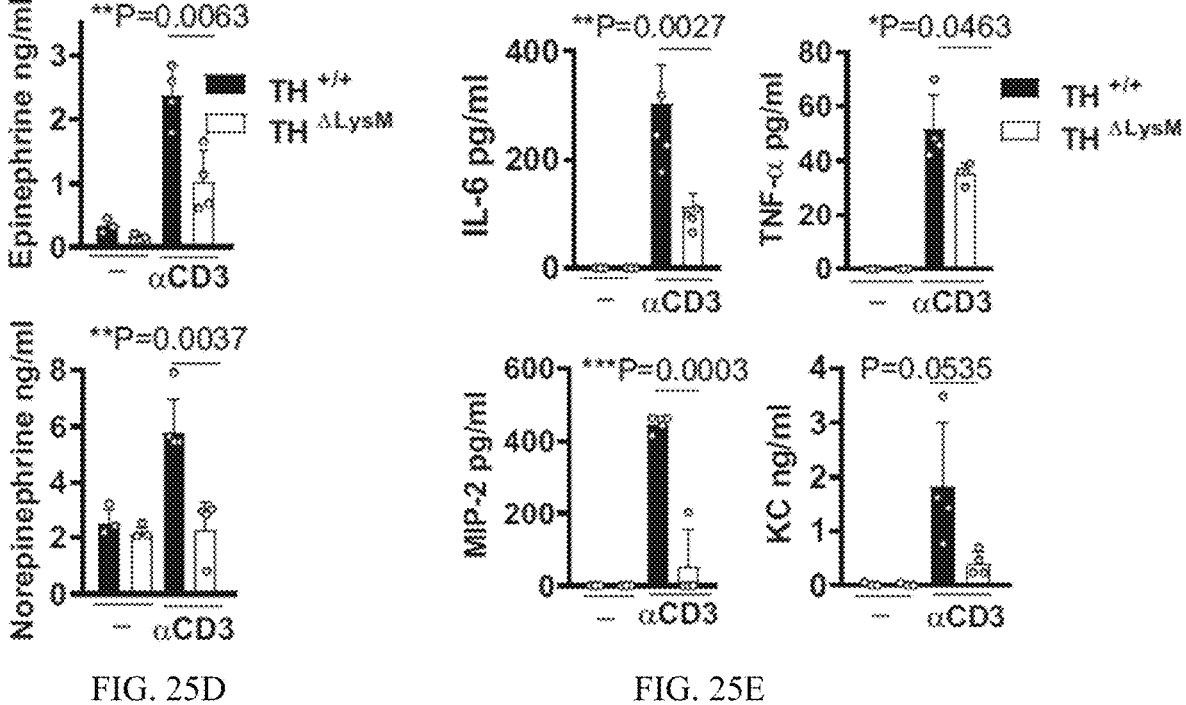
FIG. 25D                              FIG. 25E

FIG. 27A                    FIG. 27B

Day 0 of hCART19 (low tumour burden)

FIG. 28E                                      FIG. 28F

PREVENTING CYTOKINE RELEASE SYNDROME

CROSS-REFERENCE TO RELATED APPLICATIONS

This application is a continuation of U.S. application Ser. No. 16/957,970, filed Jun. 25, 2020, which is a National Stage application under 35 U.S.C. § 371 of International Application No. PCT/US2018/064969 having an International Filing date of Dec. 11, 2018, which claims the benefit of U.S. Patent Application Ser. No. 62/610,620, filed on Dec. 27, 2017. The disclosure of the prior applications are considered part of (and are incorporated by reference in) the disclosure of this application.

STATEMENT REGARDING FEDERAL FUNDING

This invention was made with U.S. government support under grant No. CA062924 from the National Institutes of Health. The U.S. government has certain rights in the invention.

SEQUENCE LISTING

This application contains a Sequence Listing that has been submitted electronically as an XML file named "44807-0301002.XML". The XML file, created on May 30, 2023, is 3000 bytes in size. The material in the XML file is hereby incorporated by reference in its entirety.

BACKGROUND

1. Technical Field

This document relates to methods and materials for treating and/or preventing cytokine release syndrome (CRS). For example, this document provides methods and materials for using one or more catecholamine inhibitors to prevent a mammal from developing CRS.

2. Background Information

Inflammation is crucial for the defense against pathogens. However, when uncontrolled, the cytokines that normally mediate protective immunity and promote recovery can themselves cause a dangerous systemic hyperinflammatory state, also referred to as cytokine release syndrome (CRS) or cytokine storm, which can lead to cardiovascular collapse, multiple organ dysfunction and ultimately death (Kopf et al., 2010 *Nat. Rev. Drug Disc.,* 9:703-18; Medzhitov, 2008 *Nature,* 454:428-35; Nathan, 2002 *Nature,* 420:846-52; Rittirsch et al., 2008 *Nat. Rev. Immunol.,* 8:776-87; van der Poll et al., 2017 *Nat. Rev. Immunol.,* 17:407-20; and Wiersinga et al., 2014 *Virulence,* 5:36-44). In addition to infections by naturally occurring pathogens as in sepsis, CRS is also observed after certain biologics and/or immunotherapeutics are administered to experimental animals or patients. These include oncolytic viruses and bacteria (Rommelfanger et al., 2013 *Mol. Ther.,* 21:348-57; and Agrawal et al., 2004 *PNAS USA,* 101:15172-7), antibodies to cells or soluble components of the immune system (Suntharalingam et al., 2006 *New Eng. J. Med.,* 355:1018-28; Ferran et al., 1990 *Eur. J. Immunol.,* 20:509-15; and Hansel et al., 2010 *Nat. Rev. Drug Disc.,* 9:325-38), cytokines (Panelli et al., 2004 *J Transl Med,* 2:17-31), and T-cells designed to kill cancer cells (Teachey et al., 2016 *Can. Disc.,* 6:664-79; Fitzgerald et al., 2017 *Crit. Care Med.,* 45:e124-e31; Grupp et al., 2013 *New Eng. J. Med.,* 368:1509-18; Lee et al., 2014 *Blood,* 124: 188-95; and Maude et al., 2014 *New Eng. J. Med.,* 371: 1507-17). In fact, the major dose-limiting toxicities of modern biotherapeutic agents can be attributed to the excessive cytokine release, thereby seriously limiting the utility of these otherwise promising agents.

SUMMARY

This document provides methods and materials for treating and/or preventing CRS. For example, this document provides methods and materials for administering one or more catecholamine inhibitors to prevent a mammal from developing CRS. For example, this document provides methods and materials for administering one or more catecholamine inhibitors to prevent CRS in a mammal at risk of developing CRS.

As demonstrated herein, catecholamines orchestrate an immune dysregulation via a self-amplifying loop in immune system cells, and catecholamine inhibitors (e.g., ANP, metyrosine, and/or prazosin) can be used to suppress catecholamine synthesis. Pharmacologic inhibition of catecholamine synthesis protected mice from the lethal complications of CRS resulting from infections and various biotherapeutic agents including oncolytic bacteria, antibodies, and CAR-T cells. Having the ability to prevent CRS by disrupting a catecholamine synthesis loop provides a unique and unrealized opportunity to treat and/or prevent life-threatening toxicities associated with therapies with biotherapeutic agents.

In general, one aspect of this document features a method for preventing cytokine release. The method includes, or consists essentially of, administering a catecholamine inhibitor to a mammal identified as being at risk of developing CRS. The CRS can be associated with sepsis. The CRS can be associated with an immunotherapy (e.g., orthoclone OKT3, muromonab-CD3, rituximab, alemtuzumab, tosituzumab, CP-870,893, LO-CD2a/BTI-322, TGN1412, tisagenlecleucel, axicabtagene ciloleucel, bi-specific T-cell engagers (BiTEs), adoptive T-cell therapy, dendritic cell therapy, interferon therapy, interleukin therapy, bacterial therapy, and/or viral therapy). The immunotherapy can be a cancer immunotherapy. The immunotherapy can be for treating an autoimmune disease (e.g., rheumatoid arthritis, juvenile idiopathic arthritis, ankylosing spondylitis, psoriasis, systemic lupus erythematosus, celiac disease, type 1 diabetes, autoimmune encephalomyelitis, multiple sclerosis, central nervous system autoimmune demyelinating diseases, chronic inflammatory demyelinating polyneuropathy, transverse myelitis, polymyositis, dermatomyositis, Crohn's disease, ulcerative colitis, autoimmune hemolytic anemia, autoimmune cardiomyopathy, autoimmune thyroiditis, Graves' disease, Sjogren's syndrome, Goodpasture syndrome, autoimmune pancreatitis, Addison's disease, alopecia, myasthenia gravis, sarcoidosis, scleroderma, pemphigus vulgaris, mixed connective tissue disease, bullous pemphigoid, or vitiligo). The mammal can be a human. The catecholamine inhibitor can include a tyrosine hydroxylase inhibitor (e.g., metyrosine). The catecholamine inhibitor can include a natriuretic peptide (e.g., atrial natriuretic peptide (ANP), brain natriuretic peptide (BNP), C-type natriuretic peptide (CNP), and dendroaspis natriuretic peptide (DNP)). When a natriuretic peptide is ANP, the ANP can include the sequence set forth in SEQ ID NO:1. The catecholamine inhibitor can include an agent that can accelerate catecholamine degradation (e.g., a monoamine oxidase A (MAO-A) activator or a catechol-O-methyltransferase (COMT) activator). The catecholamine inhibitor can include an agent that can block catecholamine release (e.g., gabapentin). The catecholamine inhibitor can include both a natriuretic peptide (e.g., ANP) and a hydroxylase inhibitor (e.g., metyrosine). The catecholamine inhibitor can include an agent that blocks an adrenergic receptor (e.g., an α1 adrenergic receptor) such as prazosin.

In another aspect, this document features a method for inhibiting catecholamine synthesis and/or catecholamine secretion in a mammal. The method includes, or consists essentially of, administering a catecholamine inhibitor to the mammal. The catecholamine can be epinephrine, norepinephrine, dopamine, or any combination thereof. For example, the catecholamine can be epinephrine. The mammal can be a human. The catecholamine inhibitor can include a tyrosine hydroxylase inhibitor (e.g., metyrosine). The catecholamine inhibitor can include a natriuretic peptide (e.g., ANP, BNP, CNP, and DNP). When a natriuretic peptide is ANP, the ANP can include the sequence set forth in SEQ ID NO:1. The catecholamine inhibitor can include an agent that can accelerate catecholamine degradation (e.g., a MAO-A activator or a COMT activator). The catecholamine inhibitor can include an agent that can block catecholamine release (e.g., gabapentin). The catecholamine inhibitor can include both a natriuretic peptide (e.g., ANP) and a hydroxylase inhibitor (e.g., metyrosine). The catecholamine inhibitor can include an agent that blocks an adrenergic receptor (e.g., an α1 adrenergic receptor) such as prazosin.

In another aspect, this document features a method for preventing transplant rejection in a mammal. The method includes, or consists essentially of, administering a catecholamine inhibitor to the mammal. The transplant rejection can include graft-versus-host disease. The mammal can be a human. The catecholamine inhibitor can include a tyrosine hydroxylase inhibitor (e.g., metyrosine). The catecholamine inhibitor can include a natriuretic peptide (e.g., ANP, BNP, CNP, and DNP). When a natriuretic peptide is ANP, the ANP can include the sequence set forth in SEQ ID NO:1. The catecholamine inhibitor can include an agent that can accelerate catecholamine degradation (e.g., a MAO-A activator or a COMT activator). The catecholamine inhibitor can include an agent that can block catecholamine release (e.g., gabapentin). The catecholamine inhibitor can include both a natriuretic peptide (e.g., ANP) and a hydroxylase inhibitor (e.g., metyrosine). The catecholamine inhibitor can include an agent that blocks an adrenergic receptor (e.g., an α1 adrenergic receptor).

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 2A shows that a series of clones were selected and analyzed for ANP secretion in bacterial cultures by an enzyme-linked immunosorbent assay (ELISA). Clone 1-29 had the highest level of ANP secretion. FIG. 2B shows that several clones of ANP-*C. novyi*-NT were selected for testing cGMP induction in bovine aortic endothelial cells. cGMP induction was measured by ELISA. FIG. 2C shows that clones of ANP-*C. novyi*-NT showed comparable growth patterns compared to the parental *C. novyi*-NT. FIG. 2D shows that plasma ANP levels of CT26 tumor-bearing mice at 36 hours after ANP-*C. novyi*-NT spore injection. FIG. 2E shows that peak levels of additional cytokines at 36 hours after spore injection. All data are presented as means±SD.

FIG. 3A shows a Kaplan-Meier Curve (top panel) and therapeutic response (bottom panel) of ANP-*C. novyi*-NT compared to parental *C. novyi*-NT with or without supplemental ANP delivered via osmotic pumps. FIG. 3B shows haematoxylin and eosin (H&E) and anti-Ly6G antibody stained sections of the lungs, liver, and spleen. FIG. 3C shows cytokine levels measured at 36 hours after spore injection. All data are presented as means±SD.

FIG. 5A contains Kaplan-Meier curves showing survival of C57BL/6 mice after CLP. ANP delivery via osmotic pump was initiated 12 hours prior to CLP and was continued for 7 days. FIG. 5B contains H&E sections of the lungs and liver obtained 24 hours after CLP showed lower or absent pulmonary septal thickening and vacuolization in ANP-treated mice, indicating reduced inflammation. FIG. 5C shows cytokine and chemokine levels obtained at 24 hours after CLP. All data are presented as means±SD.

FIG. 6B shows cytokine levels obtained at 24 hours after CLP. All data are presented as means±SD.

FIG. 8A shows peritoneal macrophages stimulated with LPS at 50 μg/ml in vitro. Culture supernatants were collected after 24 hours and analyzed by ELISA for epinephrine and norepinephrine levels. LPS induced macrophage-derived catecholamine production, which was effectively blocked by pre-incubation with ANP or metyrosine 10 minutes before. FIG. 8B shows cytokine levels that were measured in supernatants from macrophage cultures treated as in (FIG. 8A). FIG. 8C shows catecholamine levels measured in supernatants from epinephrine-stimulated peritoneal macrophages after pre-treatment with ANP or metyrosine. Epinephrine was used at the physiological concentration of 15 ng/ml. FIG. 8D shows cytokine levels measured in peritoneal macrophages treated as in (FIG. 8C). All data are presented as means±SD.

FIG. 9A shows dopamine levels in culture supernatants of peritoneal macrophages exposed to LPS and epinephrine with or without pre-treatment with ANP or metyrosine. FIG. 9B shows plasma dopamine levels in mice treated with LPS with or without pre-treatment with metyrosine. FIG. 9C shows plasma dopamine levels in CT26 tumor-bearing mice treated with the ANP-*C. novyi*-NT strain or parental *C. novyi*-NT with or without metyrosine pre-treatment. FIG. 9D shows plasma dopamine levels in mice undergoing CLP with or without metyrosine treatment. All data are presented as means±SD.

FIGS. 10A and 10B show peritoneal macrophages pre-treated with ANP or metyrosine for 10 minutes, then stimulated with epinephrine at 15 ng/ml plus LPS at 50 μg/ml. Culture supernatants were analyzed for epinephrine and norepinephrine levels (FIG. 10A) as well as levels of the indicated cytokines and chemokines (FIG. 10B). FIG. 10C shows survival of BALB/c mice after the indicated treatments. FIGS. 10D and 10E show plasma catecholamine levels (FIG. 10D) as well as levels of indicated cytokines and chemokines (FIG. 10E) in mice receiving LPS or LPS plus epinephrine with or without metyrosine pre-treatment. All data are presented as means±SD.

FIGS. 11A and 11B show co-cultures of CART19 and Raji with or without metyrosine and ANP were stimulated with 15 ng/ml of epinephrine in vitro. Culture supernatant were collected after 24 hours and analyzed for catecholamines (FIG. 11A) and the indicated cytokines (FIG. 11B). Epinephrine (old): epinephrine at 15 ng/ml was incubated at 37° C. for 24 hours in the cell-free medium. Epinephrine (new): epinephrine at 15 ng/ml was added into the cell-free medium and immediately measured. FIG. 11C shows plasma dopamine levels in mice carrying Raji tumors at two time points after CART19 treatment. Metyrosine was able to reduce dopamine production.

FIG. 12A shows survival of CT26 tumor-bearing BALB/c mice undergoing *C. novyi*-NT therapy with or without metyrosine pre-treatment. FIG. 12B shows plasma levels of epinephrine and norepinephrine from CT26 tumor-bearing mice treated with parental *C. novyi*-NT spores with or without metyrosine pre-treatment, compared to ANP-*C. novyi*-NT-treated mice. FIG. 12C shows plasma levels of indicated cytokines at 36 hrs after *C. novyi*-NT spore administration with or without metyrosine pre-treatment. FIG. 12D shows survival of C57BL/6 mice undergoing CLP with or without metyrosine and imipenem pre-treatments. FIG. 12E shows plasma levels of epinephrine and norepinephrine at different time points after CLP with or without metyrosine pre-treatment. FIG. 12F shows plasma levels of indicated cytokines after CLP, with or without metyrosine pre-treatment. Data are presented as means±SD.

FIGS. 13A-13G shows that inhibition of catecholamine synthesis reduces CRS after anti-CD3 and CART19 treatment. FIG. 13A shows survival of mice treated with anti-CD3 with or without metyrosine pre-treatment. FIG. 13B shows levels of epinephrine and norepinephrine measured at 24 hours after anti-CD3 treatment with or without metyrosine. FIG. 13C shows plasma levels of indicated cytokines at 24 hours after anti-CD3 treatment with or without metyrosine. FIG. 13D shows in vitro co-culture of CART19 with Raji cells (5:1) increased catecholamine production (epinephrine, norepinephrine). Both metyrosine and ANP suppressed the catecholamine surge. FIG. 13E shows that CART19-induced release of indicated cytokines was blocked by metyrosine and ANP in vitro. FIG. 13F shows that in vivo CART19 treatment increased circulating catecholamines, assessed at 24 and 72 hours after CART19 IV injection. Metyrosine was able to block that effect. FIG. 13G shows that the indicated circulating mouse and human cytokines were significantly lowered in metyrosine pre-treated mice. The data are presented as the mean±SD.

FIG. 14A shows levels of dopamine measured at 24 hours after anti-CD3 treatment with or without metyrosine. FIG. 14B shows levels of indicated cytokines measured at 24 hours after anti-CD3 treatment with or without metyrosine.

FIG. 16A shows Kaplan-Meier curves of mice with large subcutaneous CT26 tumours (600-900 mm$^3$), treated with intratumorally injected 12×10$^6$ *C. novyi*-NT spores and the indicated agents: anti-IL-6R (n=10), metronidazole (n=5), dexamethasone (n=6), anti-IL3 (n=6) and anti-TNF-α (n=5) compared to controls (n=5). Survival differences were analysed by two-sided log-rank test. FIGS. 16B and 16C show selected clones of ANP-*C. novyi*-NT were analysed for ANP secretion, shown as the average of a triplicate, (B) and for cGMP induction (n=3) using bovine aortic endothelial cells (C). FIG. 16D shows a growth pattern of several clones compared to the parental *C. novyi*-NT. The average of a triplicate is shown. FIGS. 16E-16G shows levels of plasma ANP (left to right, n=7, 8, 7, 5 independent samples per column) (E), plasma cGMP (n=5, 5, 4, 4 samples per column) (F) and germinated *C. novyi* strains in tumour tissue (n=4 samples per column) based on quantification cycle (C$_q$) of RT-PCR of germination-specific NT01CX1854 gene (G), measured at 36 hours after spore injection. FIG. 16H shows representative haematoxylin and eosin as well as anti-CD11b antibody stained sections from the lungs, liver, spleen and bone marrow of mice treated with ANP-*C. novyi*-NT (n=3), *C. novyi*-NT (n=3) and *C. novyi*-NT plus ANP (n=2) compared to normal controls (n=2). FIGS. 16I-16M show pulmonary permeability (n=4 mice per group), lung wet-dry ratio (n=3 mice per group) (I) as well as levels of cytokines (n=6 independent samples per column) (J), dopamine (n=3 independent samples per column) (K), haematocrit (n=3, 5, 4, 4 samples per column) (L) and calculated plasma volume (n=3, 5, 4, 4 samples per column) (M) measured 36 hours after spore treatment. Data in FIGS.

16C, 16E-16G, and 16I-16M are presented as mean±s.d. with individual data points shown, analysed by two-tailed t-test. BAEC, bovine aortic endothelial cells.

Figure 17A:
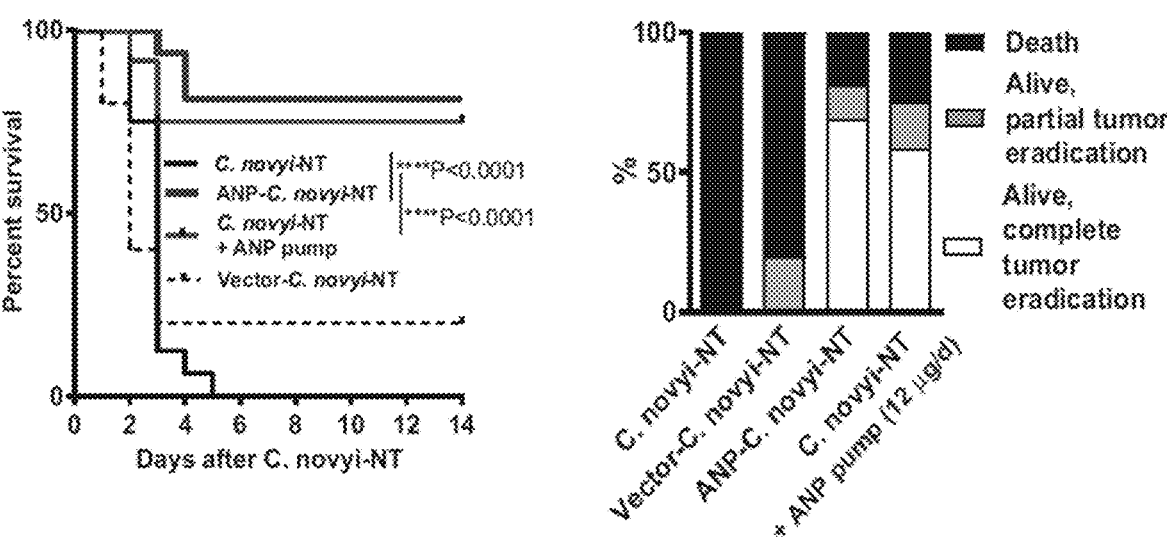
Figure 17B:
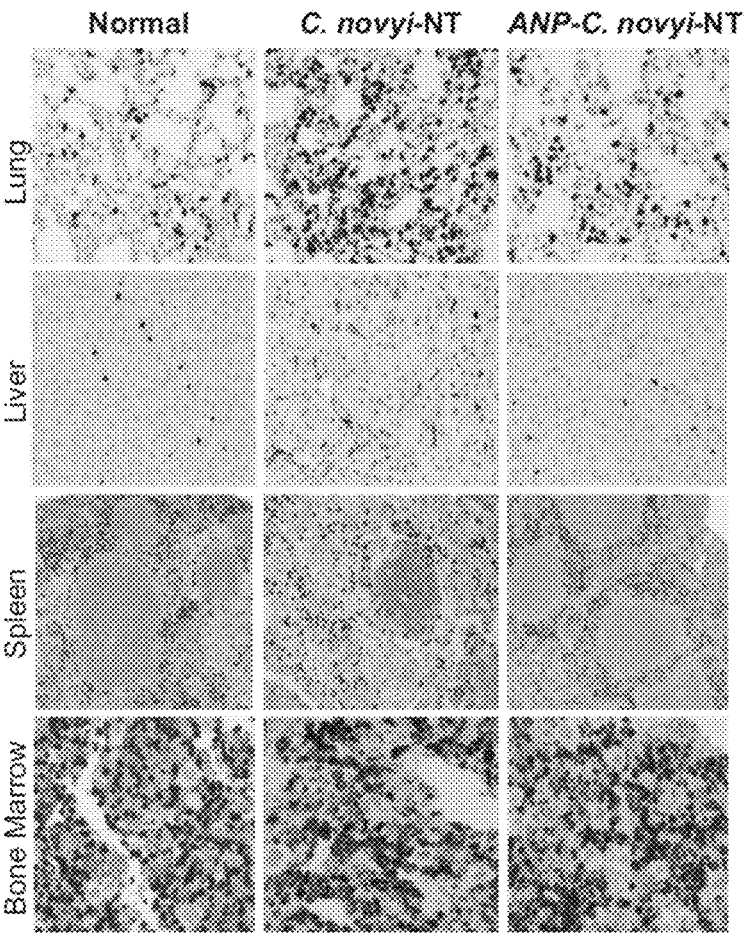
Figure 17C:
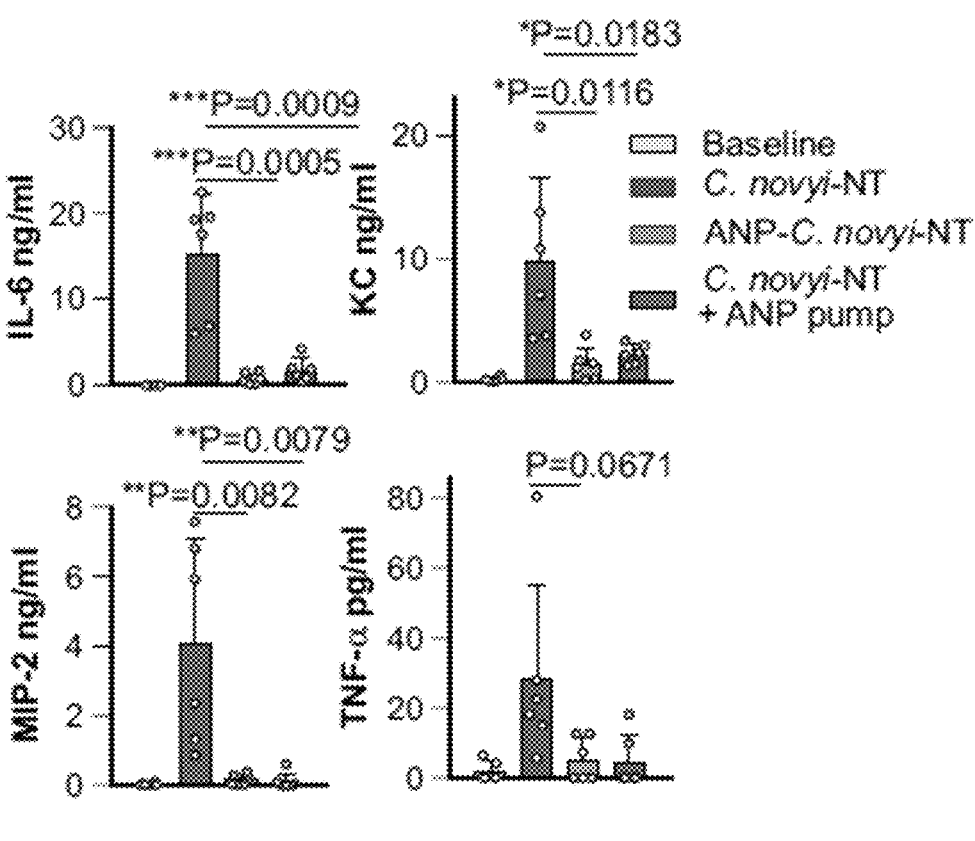
Figure 17D:
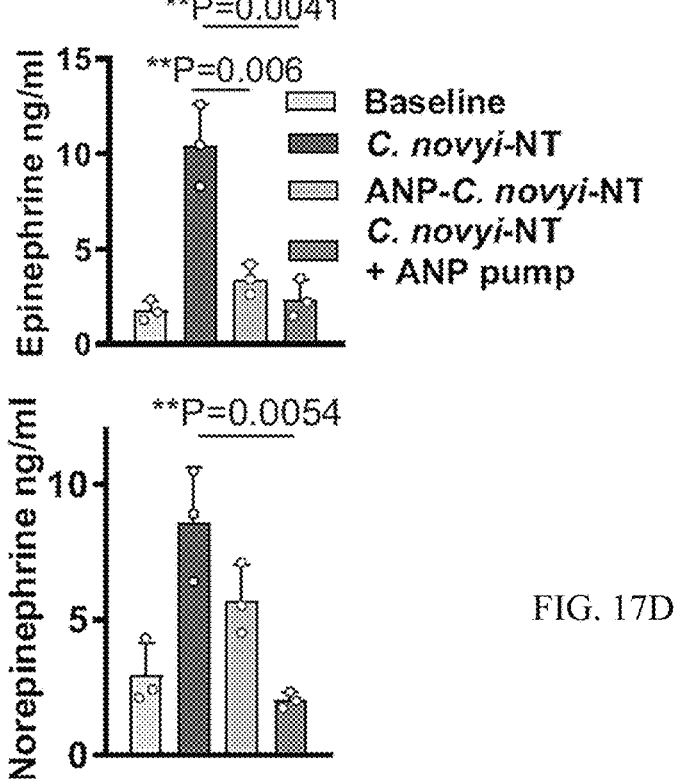

FIGS. 17A-17D show that ANP reduces mortality. FIG. 17A shows a Kaplan-Meier curve (top panel) and therapeutic response (bottom panel) of ANP-*C. novyi*-NT (n=16) compared to *C. novyi*-NT (n=16), *C. novyi*-NT with ANP via osmotic pump (n=12) and vector *C. novyi*-NT control (n=5). Statistical survival differences were evaluated by two-sided log-rank test. FIG. 17B shows representative anti-CD11b-antibody-stained sections from the lungs, liver, spleen and bone marrow of mice treated with ANP-*C. novyi*-NT (n=3) and *C. novyi*-NT (n=3) compared to normal controls (n=2). FIG. 17C shows plasma levels of indicated cytokines (n=6 independent samples per group) 36 hours after spore injection. FIG. 17D shows corresponding plasma levels of epinephrine and norepinephrine 36 hours after *C. novyi*-NT, ANP-*C. novyi*-NT and *C. novyi*-NT plus ANP pump compared to normal controls (n=3 per group). FIG. 17C and FIG. 17D data are presented as mean±s.d. with individual data points shown, analysed by two-tailed t-test.

Figure 18A:
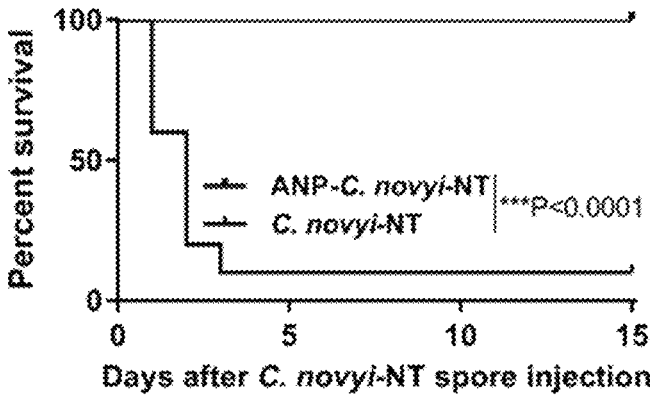
Figure 18B:
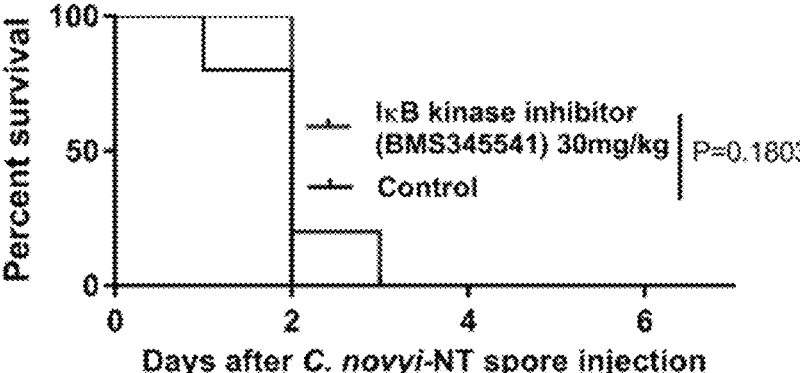

FIGS. 18A and 18B show survival of mice treated with ANP and IκB kinase inhibitor BMS345541. FIG. 18A shows survival of mice with subcutaneously implanted GL-261 tumours, treated with 12×10$^6$ of ANP-*C. novyi*-NT spores (n=10 animals per group). FIG. 18B shows survival of mice treated with *C. novyi*-NT and IκB kinase inhibitor BMS345541 (n=5 mice per group). Survival differences were analysed by two-sided log-rank test.

Figure 19A:
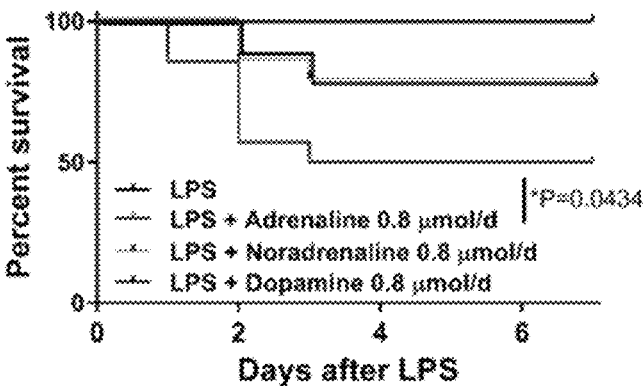
Figure 19B:
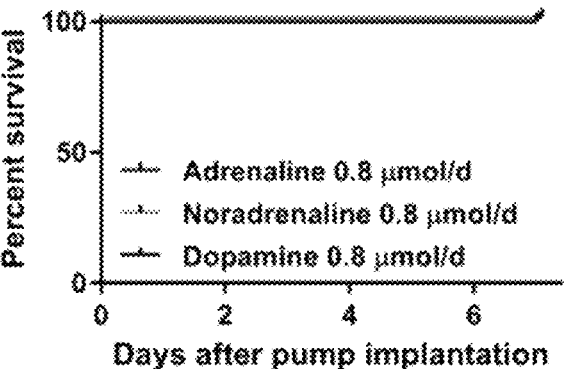
Figures 19C, 19D:
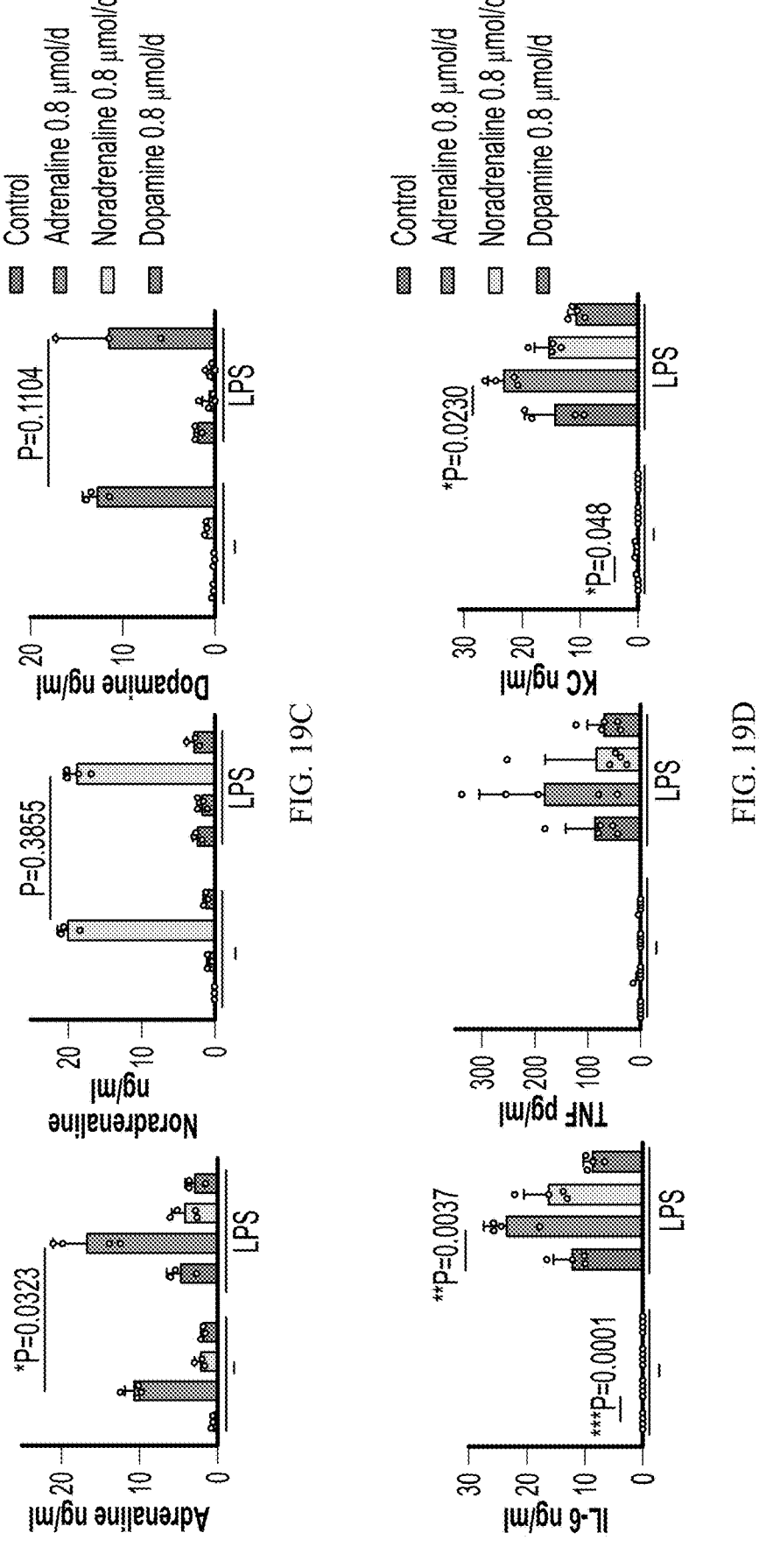
Figures 19E, 19F, 19G:
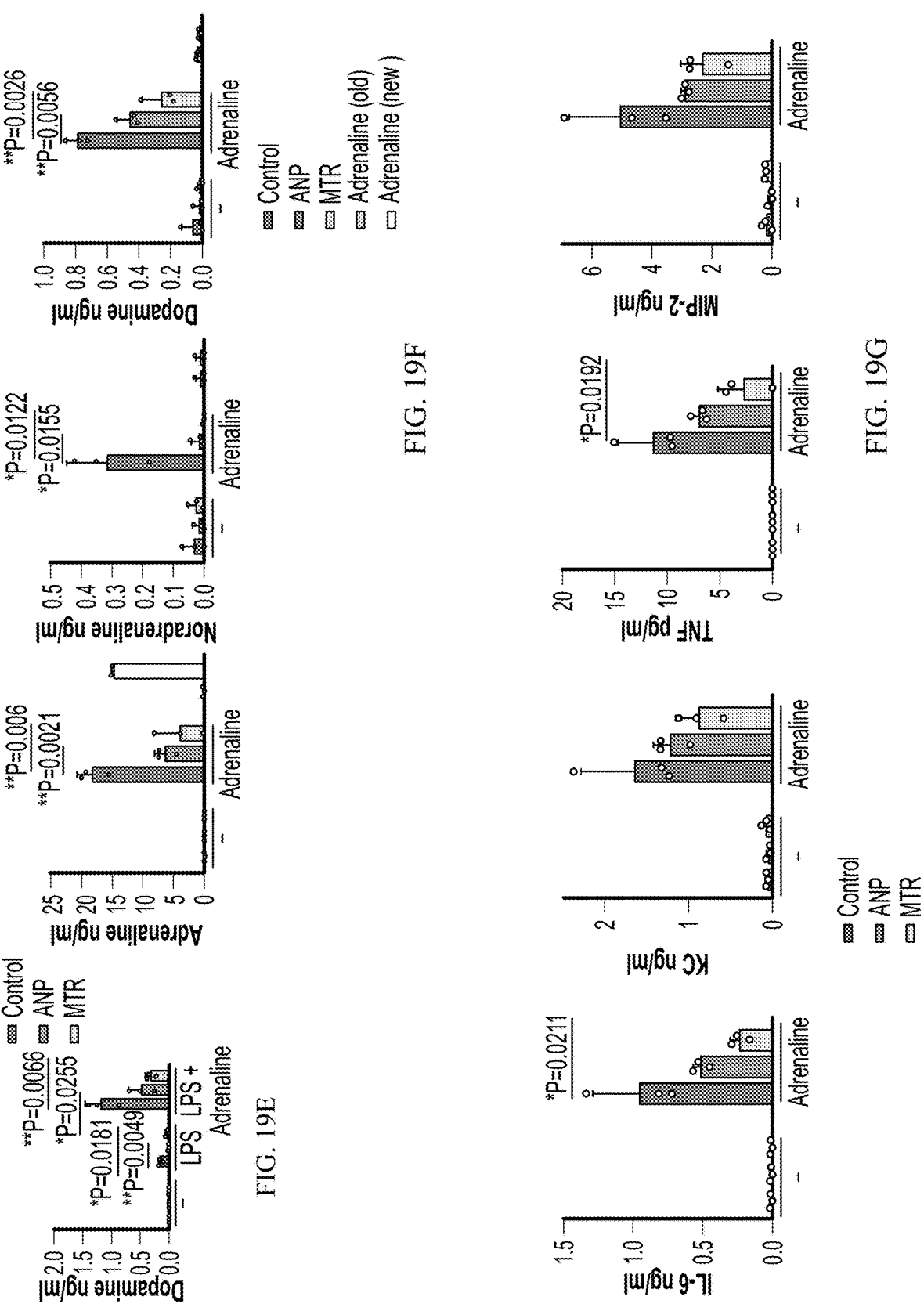

FIGS. 19A-19D show that epinephrine increases catecholamine levels and enhances the inflammatory response. FIG. 19A shows survival of BALB/c mice implanted with the indicated catecholamine pump and stimulated with a sublethal dose of LPS (n=14 mice per group) compared to LPS alone (n=19 mice). Survival differences were analysed by Gehan-Breslow-Wilcoxon test. FIG. 19B shows survival of BALB/c mice with indicated catecholamine pump without LPS stimulation (n=5 mice per group). FIGS. 19C and 19D shows 24 hour plasma levels of epinephrine (left to right, n=3, 4, 3, 3, 3, 4, 4, 3 per column), norepinephrine (n=3, 3, 3, 3, 3, 4, 4, 3) and dopamine (n=3, 3, 3, 3, 3, 4, 4, 3) (C) as well as levels of IL-6 (n=4 per column), TNF-α (n=5 per column) and KC (n=4 per column) (D) in mice receiving the indicated treatments. FIG. 19E shows dopamine concentration of LPS and epinephrine treated peritoneal macrophages pre-incubated with ANP or MTR (n=3 per column), measured after 24 hours. FIGS. 19F and 19G show levels of catecholamines (n=3 independent samples per column) (F) and several cytokines (n=3 independent samples per column) (G) in epinephrine (15 ng ml$^{-1}$)-treated peritoneal macrophages pre-incubated with ANP or MTR and measured after 24 hours. Data in FIGS. 19C-19G are presented as mean±s.d. with individual data points shown, analysed by two-tailed t-test.

Figures 20A, 20B:
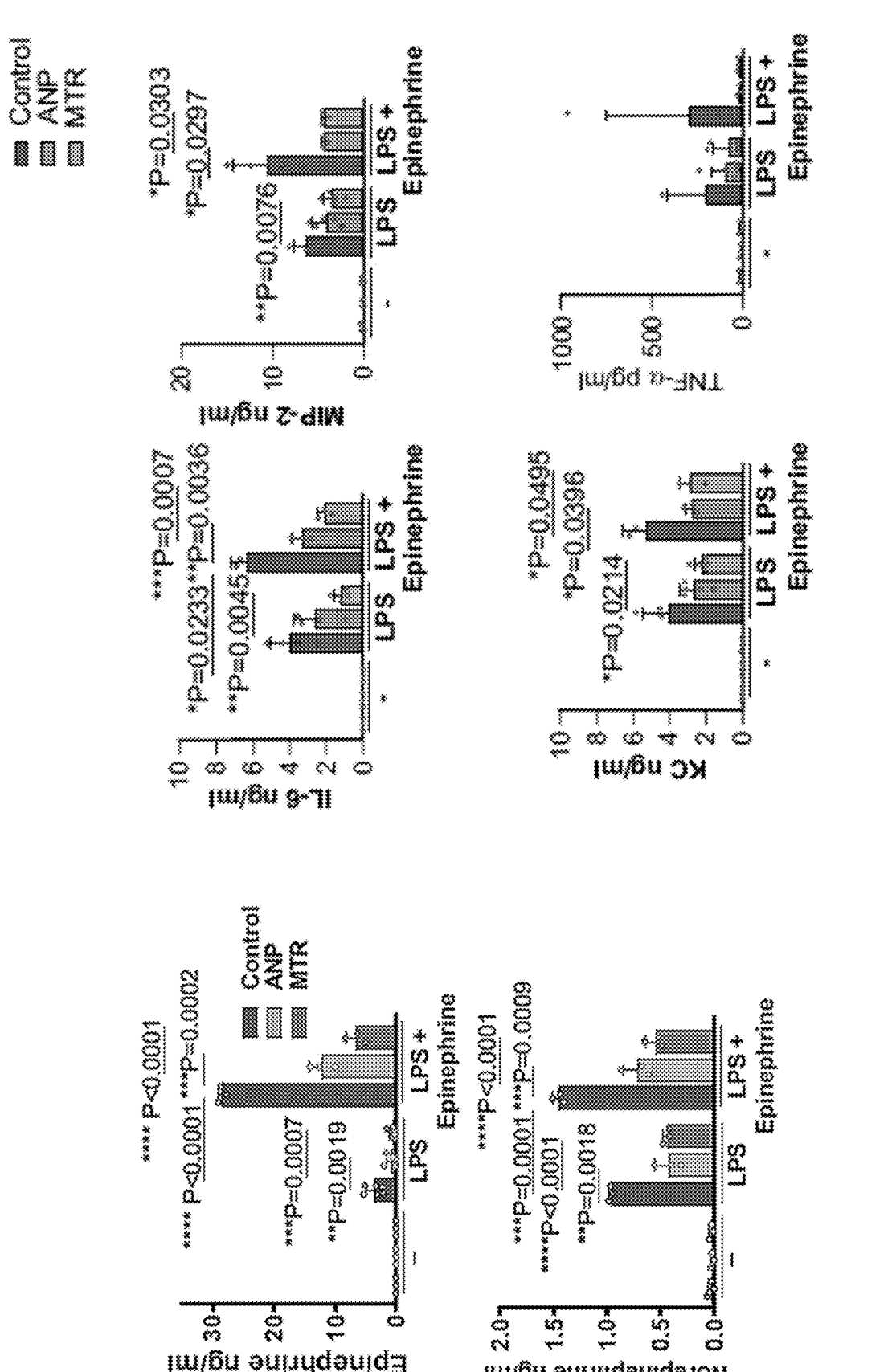

FIGS. 20A-20B show that catecholamine production in myeloid cells is essential for cytokine release. FIG. 20A shows peritoneal macrophages that were pre-incubated with ANP or MTR for 10 minutes and then stimulated with LPS (50 μg ml$^{-1}$) or a combination of LPS and epinephrine (15 ng ml$^{-1}$) in vitro. Shown are the levels of epinephrine (left to right, n=3, 3, 3, 6, 6, 6, 3, 3, 3 per column) and norepinephrine (n=3) in the supernatant after 24 hours. FIG. 20B shows corresponding cytokines from macrophage culture supernatants: IL-6 (n=3, 3, 3, 4, 4, 4, 3, 3, 3), MIP-2 (n=4, 4, 4, 4, 5, 5, 4, 3, 3), KC (n=3, 3, 3, 5, 5, 5, 3, 3, 3) and TNF-□ (n=3, 3, 3, 3, 5, 6, 4, 3, 3). Data in FIGS.

20A-20B are presented as mean s.d. with individual data points shown, analysed by two-tailed t-test.

FIGS. 20C-20E shows that catecholamines derived from myeloid cells modulate the cytokine release in vivo. FIG. 20C shows survival of Th$^{+/+}$ and Th$^{ΔLysM}$ mice treated with LPS and analysed with two-sided log-rank test (n=12; 6 male, 6 female). FIGS. 20D and 20E show plasma levels of epinephrine (n=4, 4, 7, 6) and norepinephrine (n=3, 3, 7, 6) (D) and indicated cytokines (n=3, 3, 4, 3) (E) at baseline and 24 hours after LPS treatment in Th$^{+/+}$ or Th$^{ΔLysM}$ mice. Data in FIGS. 20D and 20E are presented as mean±s.d. with individual data points shown, analysed by two-tailed t-test.

Figure 21A:
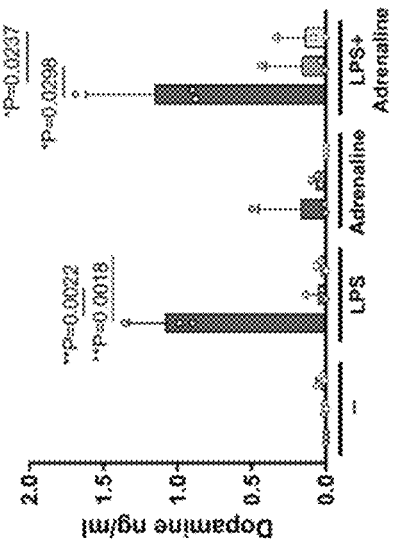
Figure 21A:
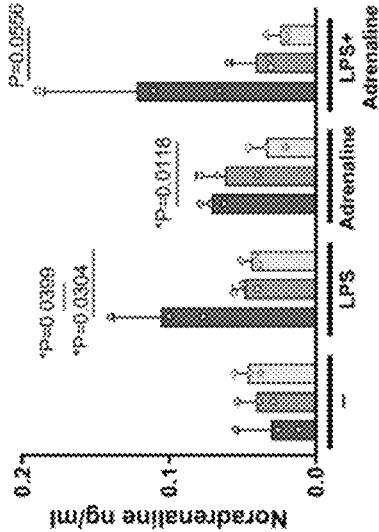
Figure 21A:
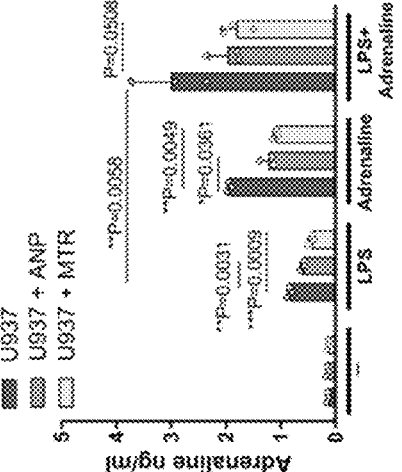
Figure 21B:
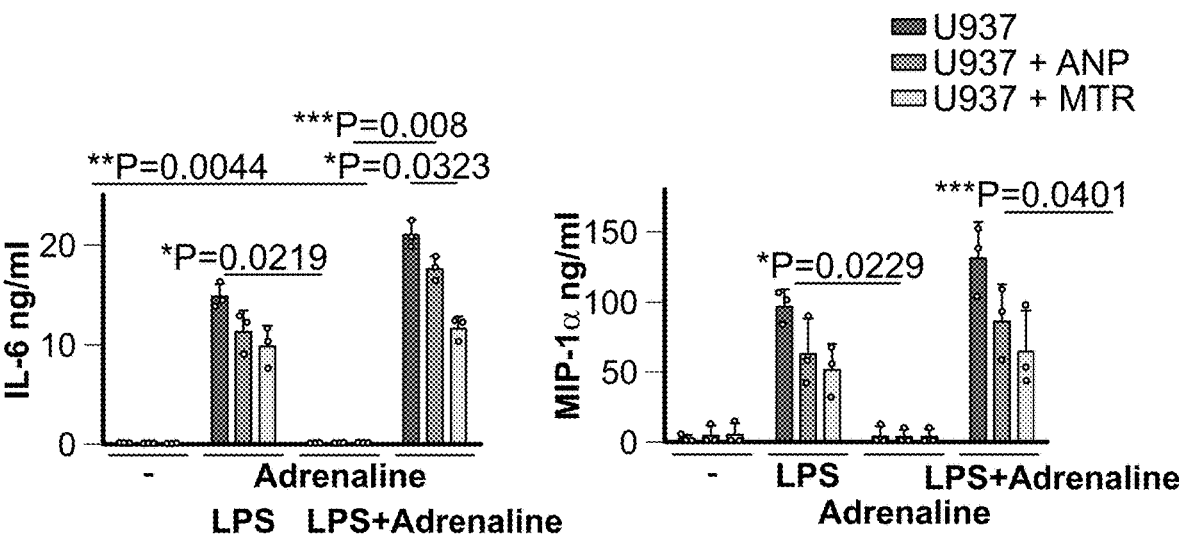
Figure 21C:
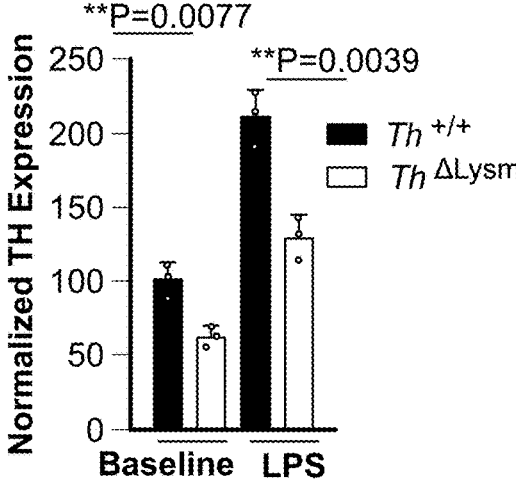
Figures 21D, 21E:
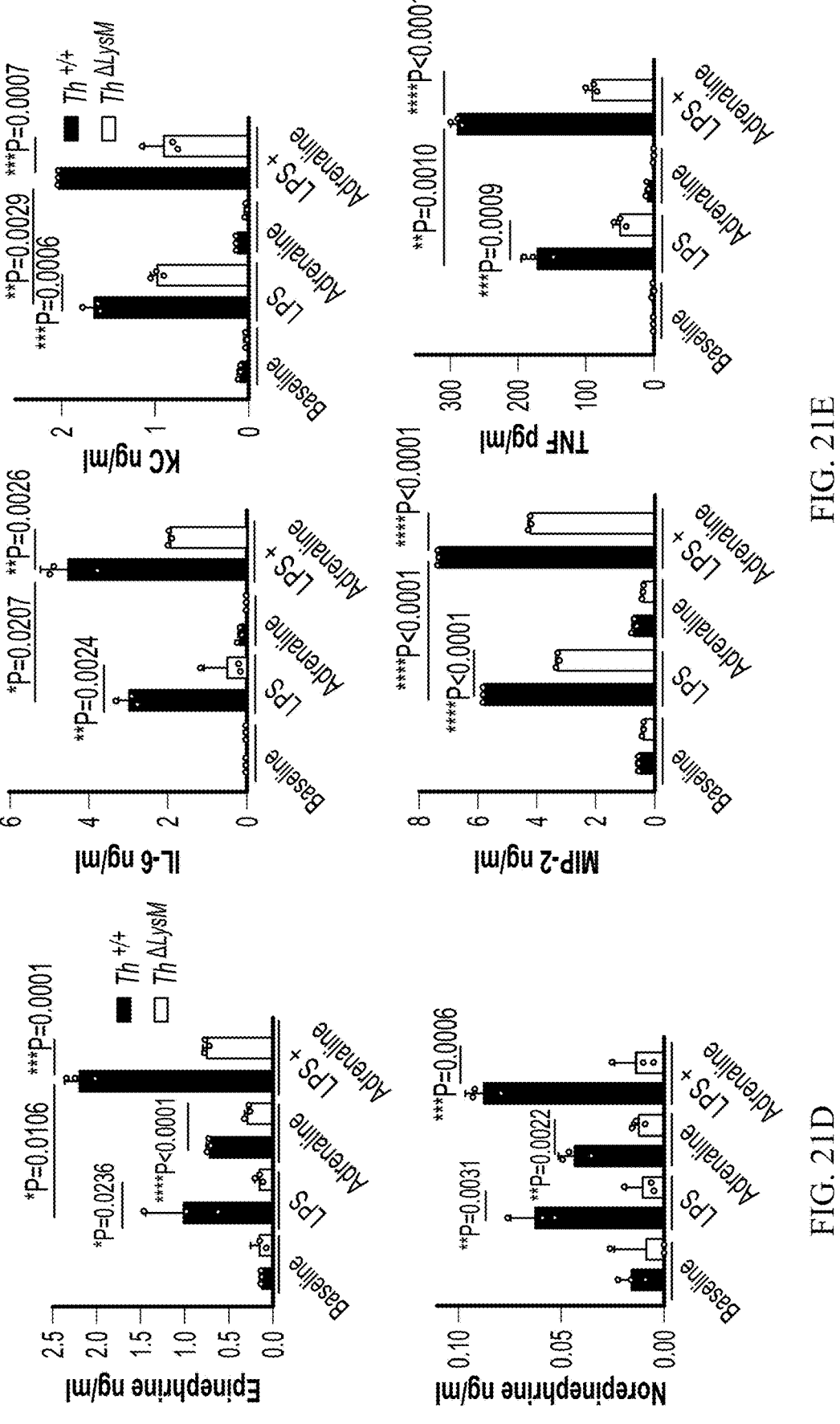

FIGS. 21A-21E shows autocrine and LPS-induced catecholamine production enhance the cytokine release in human U937 macrophage line. FIGS. 21A and 21B show U937 cells that were pre-treated with ANP or MTR for 10 minutes, then stimulated with LPS at 1 μg ml$^{-1}$ and/or epinephrine at 15 ng ml$^{-1}$. Culture supernatants were analysed for catecholamines (n=3 per column) (A) as well as the indicated cytokines (n=3 per column) (B). FIG. 21C shows TH expression of baseline and LPS-stimulated Th$^{+/+}$ or Th$^{ΔLysM}$ macrophages (n=3 per group), analysed by qPCR; results are normalized by ubiquitin C (UBC). FIGS. 21D and 21E show supernatants of collected peritoneal macrophages from Th$^{+/+}$ or Th$^{ΔLysM}$ mice, stimulated with LPS at 50 μg ml$^{-1}$, epinephrine 15 μg ml$^{-1}$ or both for 24 hours, were analysed for levels of epinephrine (n=3), norepinephrine (n=3) (D) and cytokines IL-6 (n=3), KC (n=3), MIP-2 (n=3) and TNF-α (n=3) (E). All data are presented as mean±s.d. with individual data points shown, analysed by two-tailed t-test.

Figure 22A:
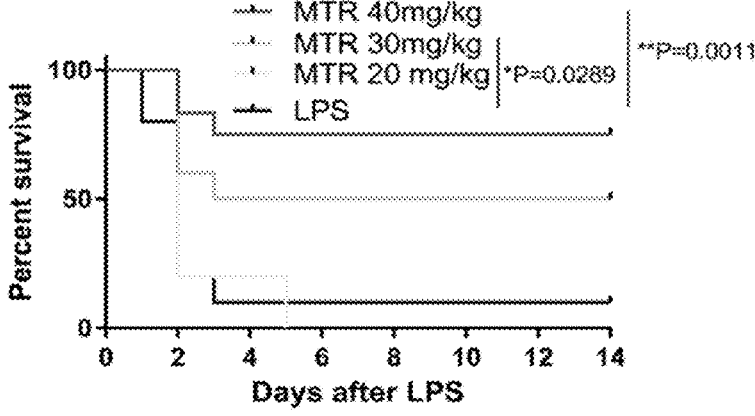
Figure 22B:
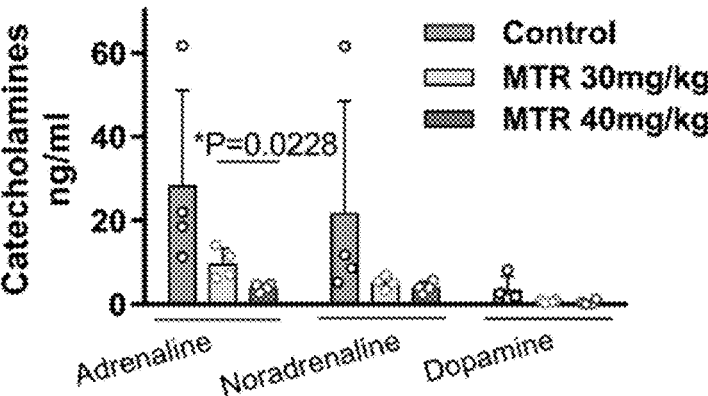
Figures 22C, 22D:
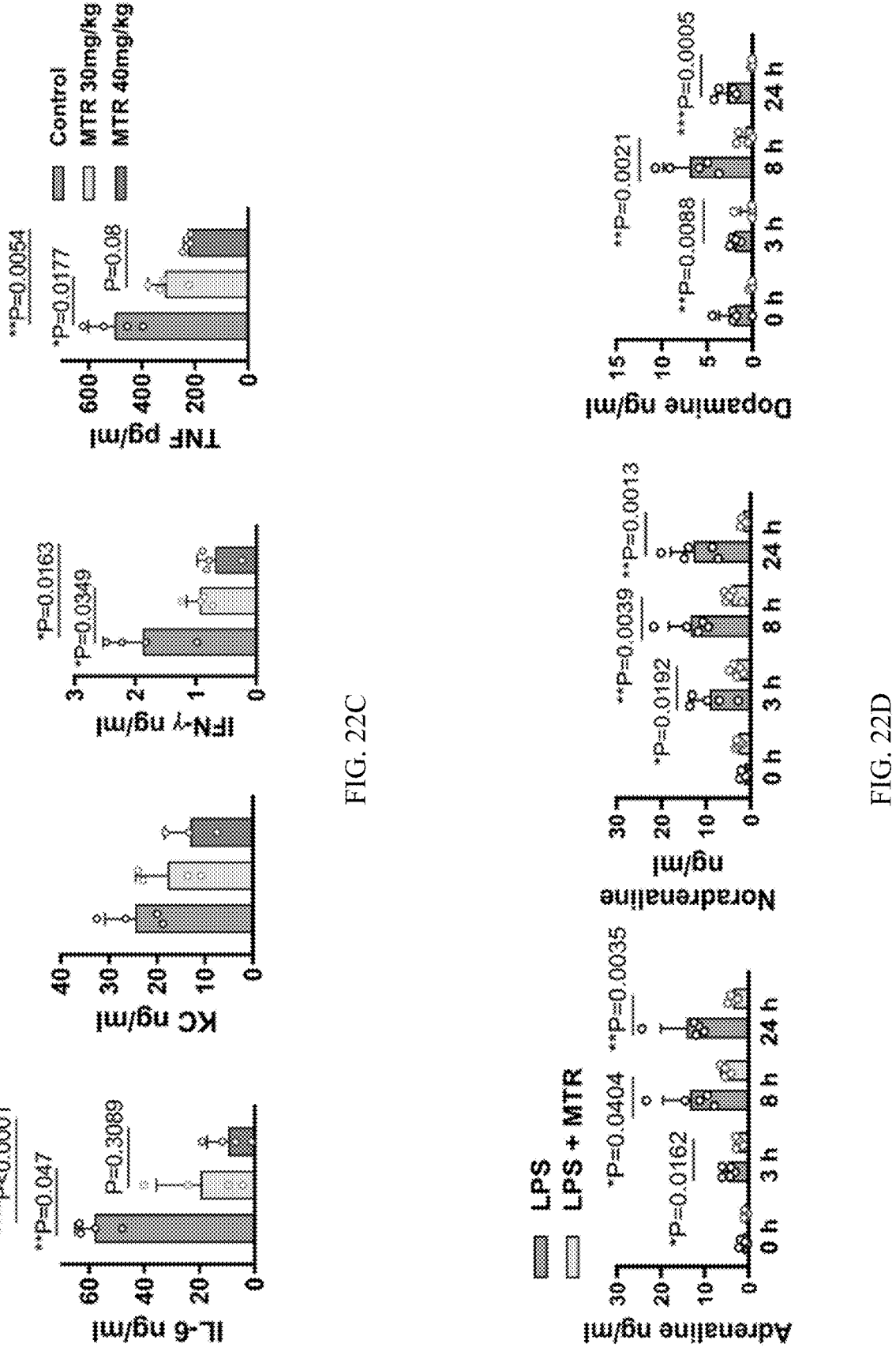
Figure 22E:
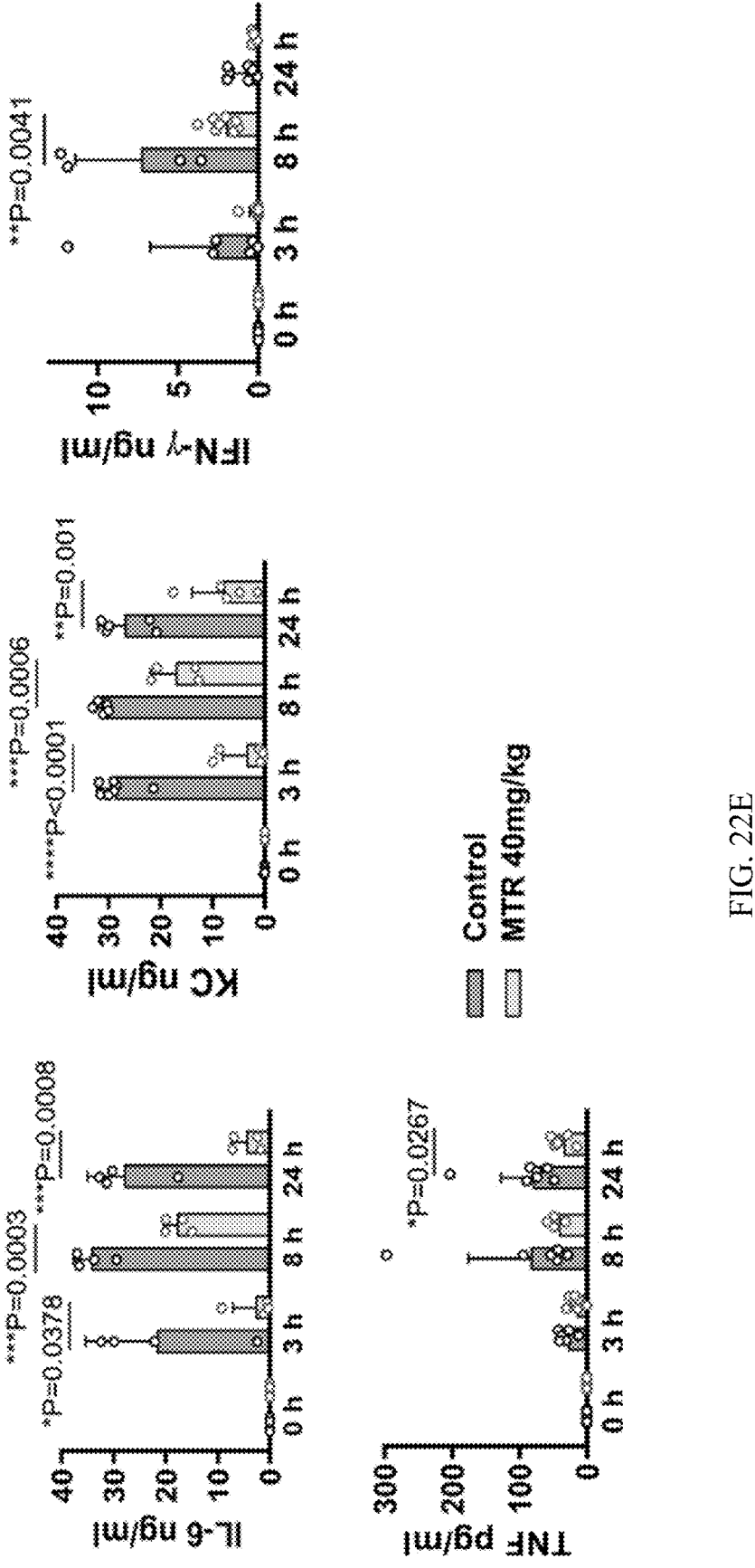

FIGS. 22A-22E show metyrosine (MTR) dose-dependently improves survival and cytokine release. FIG. 22A shows survival of BALB/c mice stimulated with a lethal dose of LPS and treated with the indicated dose of MTR. MTR 20 mg kg$^{-1}$ (n=5 mice per group); MTR 30 mg kg$^{-1}$ (n=10 mice), MTR 40 mg kg$^{-1}$ (n=12) compared to LPS (n=10 mice). Survival differences were analysed by two-sided log-rank test. FIGS. 22B and 22C show levels of plasma catecholamines (n=4 per column) (B) and IL-6 (n=4 per column), KC (left to right, n=4, 4, 3 per column), IFN-γ (n=4) and TNF-α (n=4, 4, 3) (C) at different MTR doses measured 24 hour after LPS injection. FIGS. 22D and 22E shows 24-hour-time courses of circulating epinephrine (n=5, 5, 5, 4, 5, 4, 5, 5), norepinephrine (n=5) and dopamine (n=5) (D) and corresponding levels of IL-6 (n=4), KC (n=7, 7, 7, 6, 5, 4, 5, 5), IFN-γ (n=6, 6, 6, 8, 4, 8, 6, 4) and TNF-α (n=6, 6, 6, 6, 6, 4, 7, 7) (E) in LPS-treated mice receiving MTR 40 mg kg$^{-1}$. Data in FIGS. 22B-22E are presented as mean±s.d. with individual data points shown, analysed by two-tailed t-test.

Figure 23A:
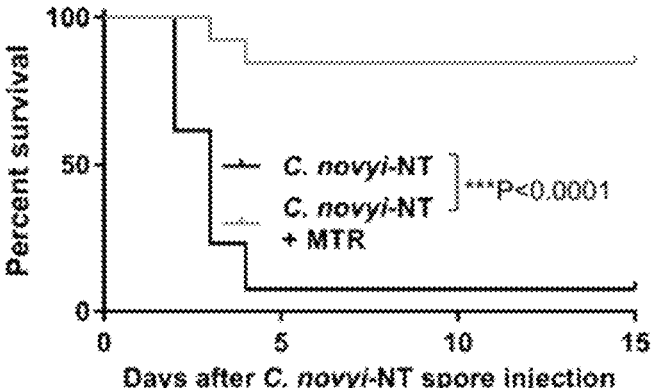
Figure 23A:
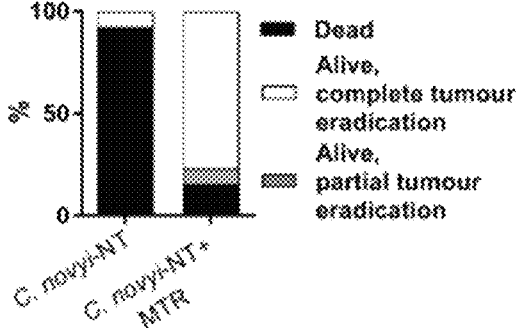
Figures 23B, 23C:
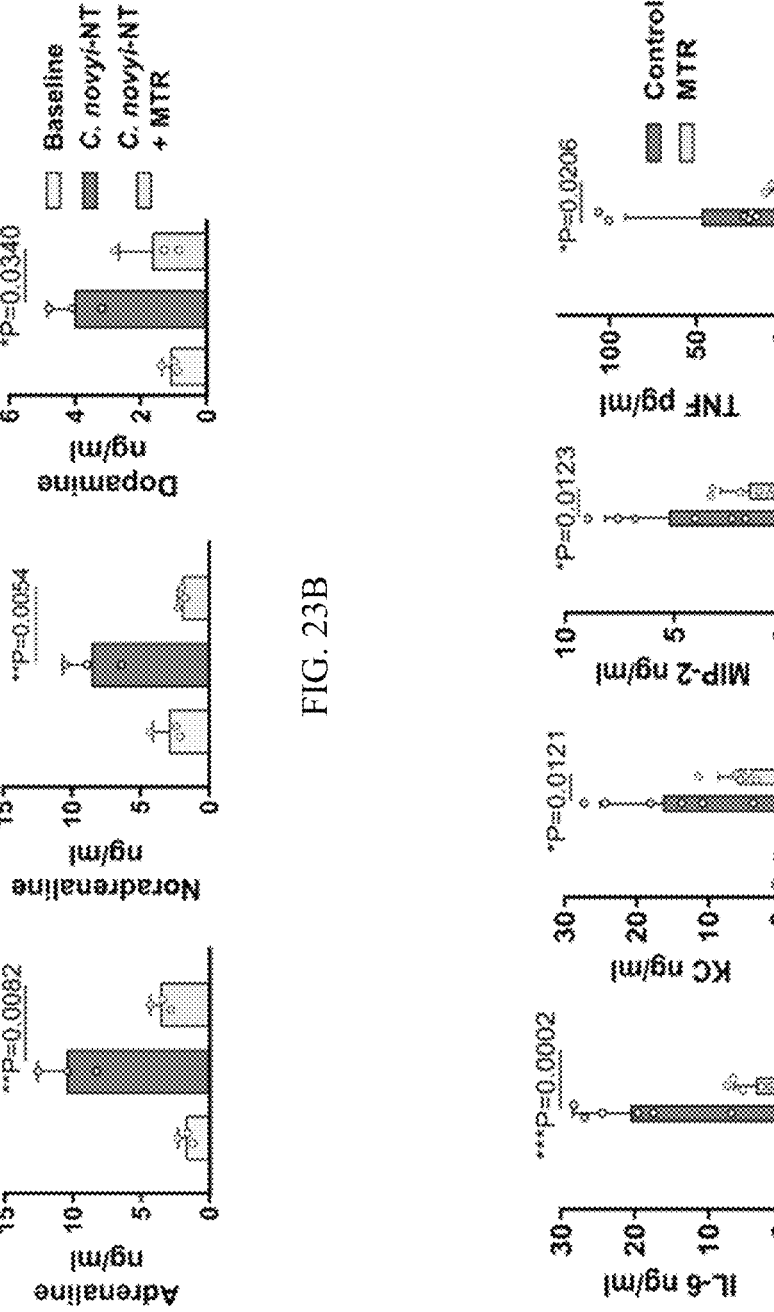
Figure 23D:
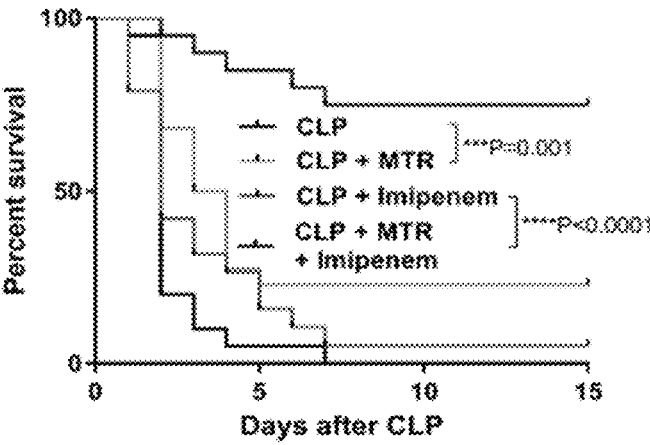
Figure 23E:
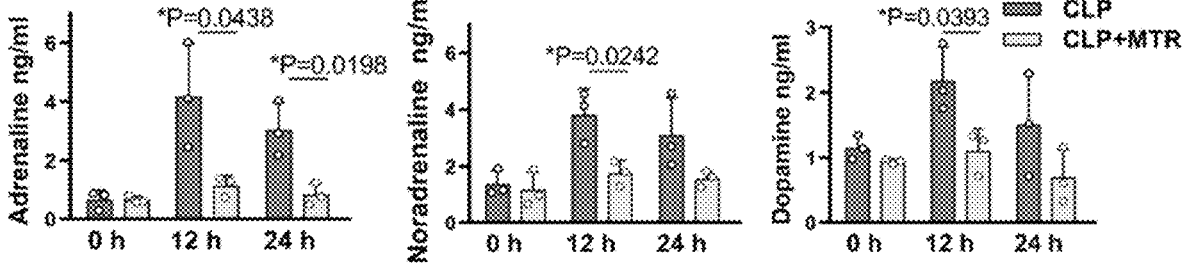
Figure 23F:
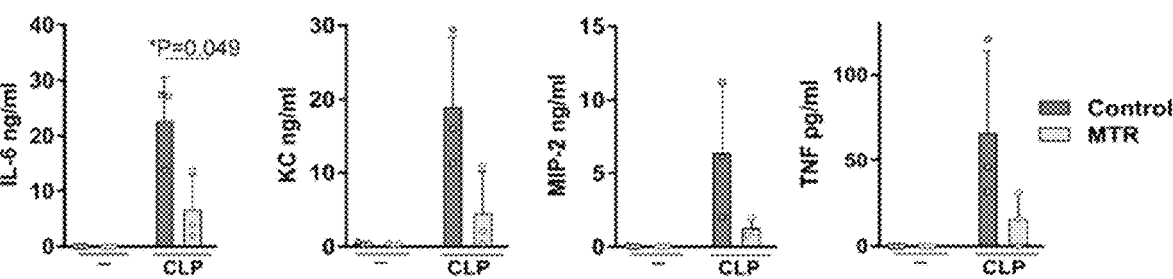
Figure 23G:
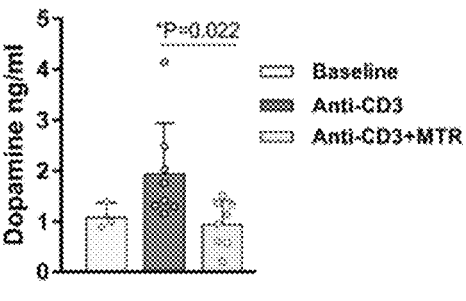
Figure 23H:
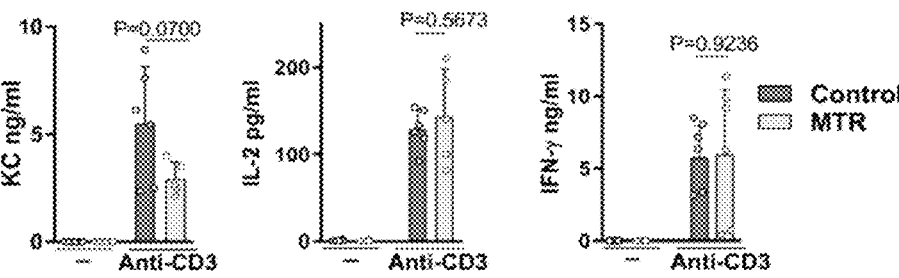

FIGS. 23A-23H shows that suppression of catecholamines with metyrosine reduces toxicity of oncolytic bacterium *C. novyi*-NT and polymicrobial sepsis. FIG. 23A shows survival (top panel) and therapeutic response (bottom panel) of CT26 tumour-bearing BALB/c mice undergoing *C. novyi*-NT treatment with or without MTR pre-treatment (n=13 mice per group). Survival differences were analysed with two-sided log-rank test. FIGS. 23B and 23C show corresponding plasma levels of epinephrine (n=3 independent samples per column), norepinephrine (n=3), dopamine (n=3) (B) and indicated cytokines (left to right, n=3, 3, 6, 7 independent samples per column) (C), measured at baseline and 36 hours after treatment. FIG. 23D shows survival of C57BL/6 mice undergoing CLP, with the indicated treatments (CLP, n=20 mice; MTR, n=22; IMP, n=19; MTR+ IMP, n=20 mice per group). Survival differences were analysed with two-sided log-rank test. FIG. 23E shows plasma levels of epinephrine (n=3), norepinephrine (n=3) and dopamine (n=3) at the indicated time points after CLP, with or without MTR pre-treatment. FIG. 23F shows levels of indicated cytokines (n=3) at baseline and 24 hours after CLP, with or without MTR pre-treatment. FIGS. 23G and 23H show levels of plasma dopamine (left to right, n=3, 8, 8 independent samples per column) (G) and KC (n=6, 6, 6, 5), IL-2 (n=6, 6, 6, 5) and IFN-γ (n=6) (H) measured 24 hours after α-CD3 treatment, with or without MTR. Data in FIGS. 23B, 23C, and 23E-23H are presented as mean±s.d. with individual data points shown, analysed by two-tailed t-test.

Figure 24A:
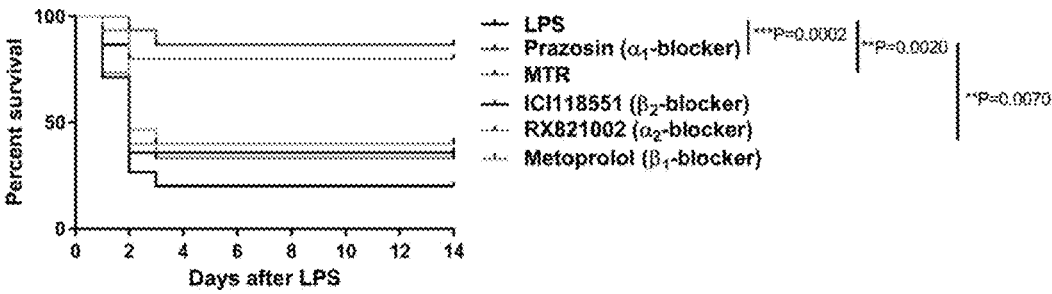
Figure 24B:
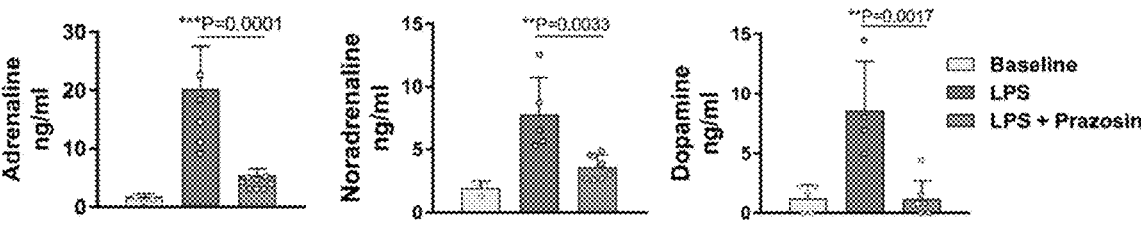
Figure 24C:
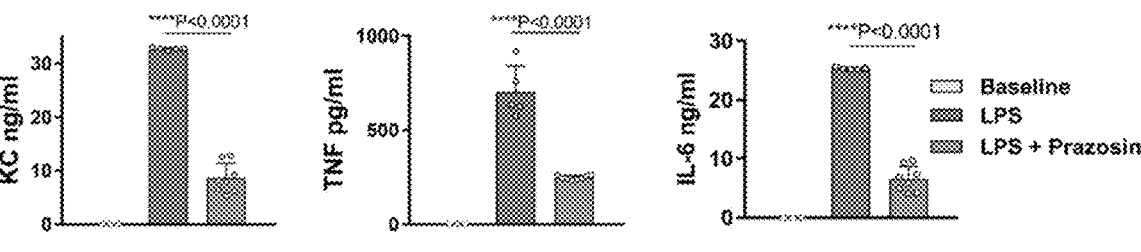

FIGS. 24A-24C shows blockage of α1-adrenoceptor mediates the survival in experimental systemic inflammatory syndrome. FIG. 24A shows Kaplan-Meier curve of LPS-injected BALB/c mice treated with the indicated adrenoreceptor blockers (n=15 animals per group). FIGS. 24B and 24C show lLevels of epinephrine, norepinephrine (left to right, n=3, 5, 8 per column) and dopamine (n=5, 4, 7) (B) as well as indicated cytokines (n=3, 5, 8) (C) measured 24 hours after LPS administration. Data in FIGS. 24B and 24C are presented as mean±s.d. with individual data points shown, analysed by two-tailed t-test.

Figure 25A:
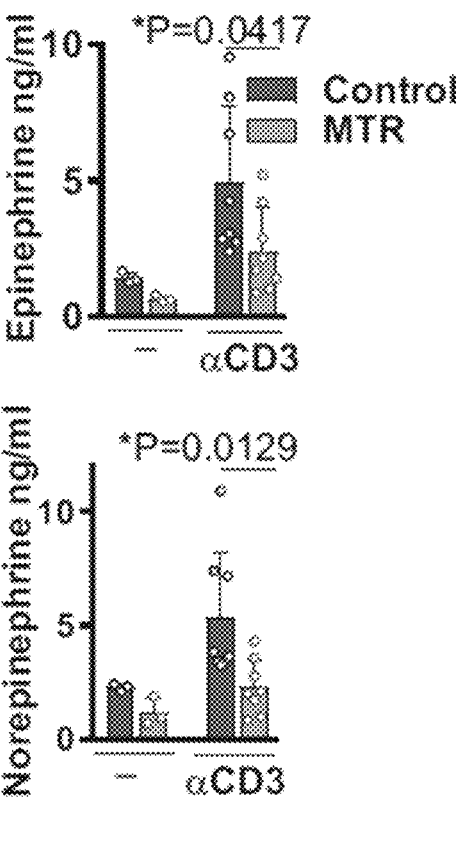
Figure 25B:
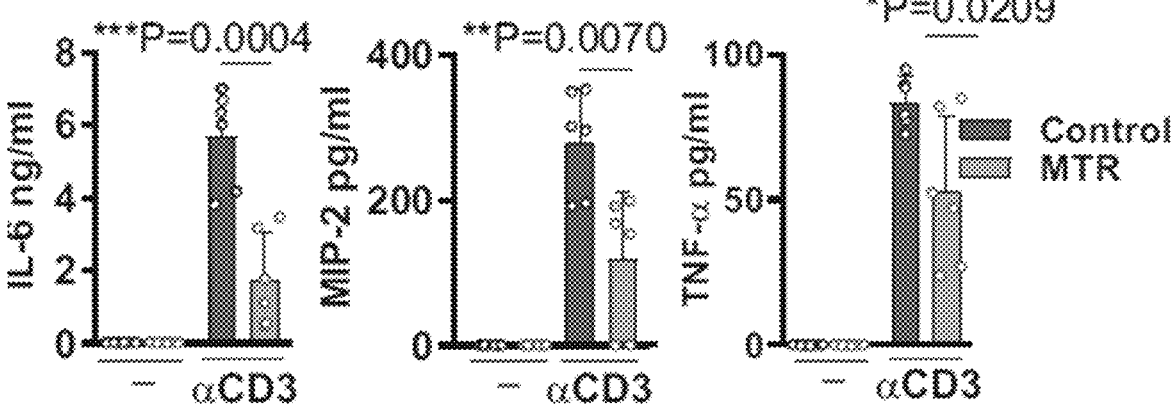

FIGS. 25A-25E show inhibition of catecholamine synthesis reduces CRS after anti-CD3 treatment. FIGS. 25A and 25B show levels of epinephrine and norepinephrine (left to right, n=3, 3, 8, 8 independent samples per column) (A) and of cytokines (n=6 independent samples) (B) measured 24 hours after anti-CD3 treatment, with or without MTR. FIG. 25C shows survival of BALB/c mice treated with anti-CD3, with or without MTR (n=15 animals); analysed by two-sided log-rank test. FIGS. 25D and 25E show levels of epinephrine, norepinephrine (n=3, 3, 4, 4) (D) and indicated cytokines (n=3, 3, 4, 4) (E) measured 24 hours after anti-CD3 treatment in $Th^{+/+}$ or $Th^{\Delta LysM}$ mice. Data in FIGS. 25A, 25B, 25D, and 25E are presented as mean±s.d. with individual data points shown, analysed by two-tailed t-test.

Figures 26A, 26B, 26C:
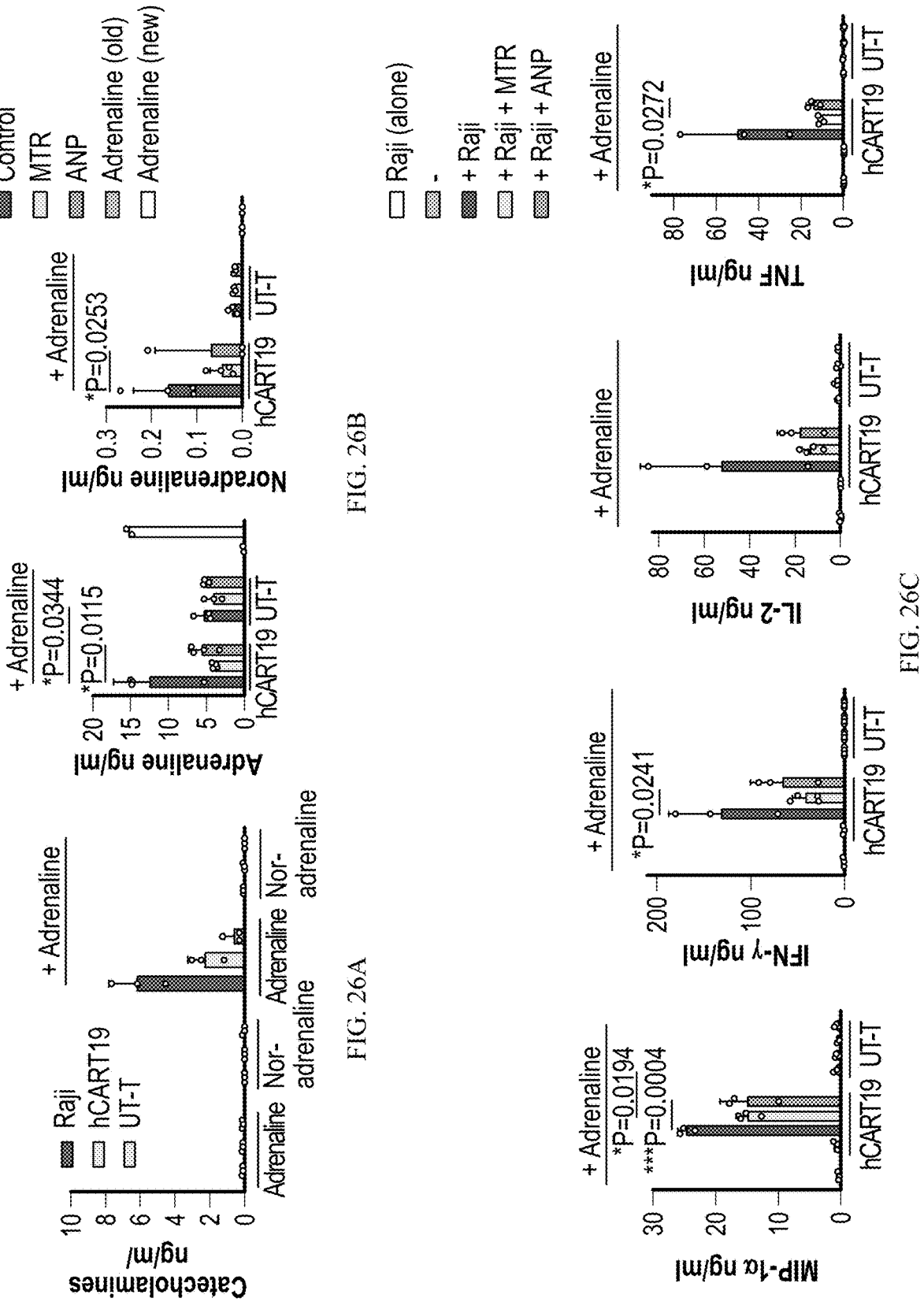
Figure 26D:
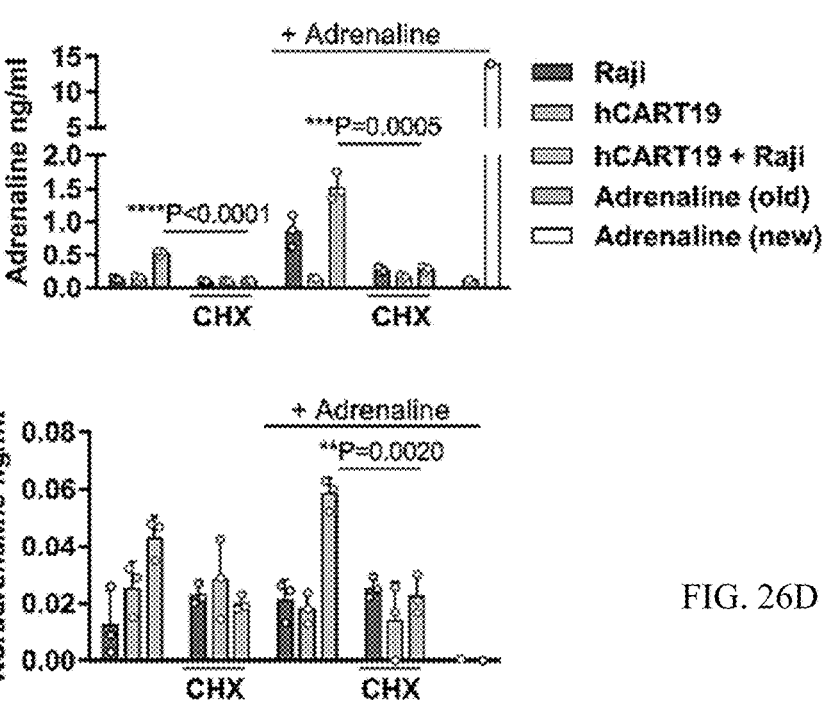
Figure 26E:
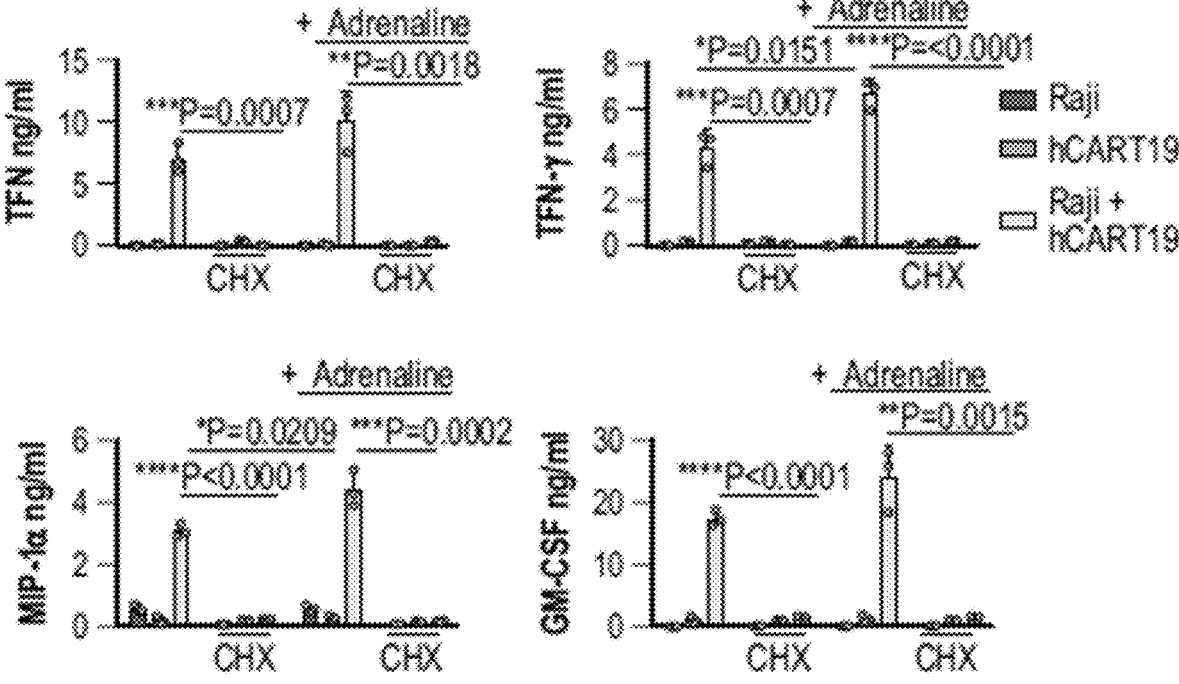

FIGS. 26A-26E show catecholamine and additional cytokine data from the hCART19 in vitro experiments. FIG. 26A shows levels of catecholamines in Raji cells (n=3), hCART19 (n=3) and UT-T (n=3 per column) at baseline and when exposed to epinephrine. FIGS. 26B and 26C show co-cultures of hCART19 and Raji with or without MTR or ANP pre-treatment were stimulated with 15 ng ml⁻¹ of epinephrine in vitro. Culture supernatants were collected after 24 hours and analysed for epinephrine (left to right, n=4, 4, 4, 3, 3, 3, 2, 2 per column) and norepinephrine (n=4, 4, 3, 3, 3, 3, 2, 2). Epinephrine (old): epinephrine at 15 ng ml⁻¹ was incubated at 37° C. for 24 hours in the cell-free medium. Epinephrine (new): epinephrine at 15 ng ml⁻¹ was added into the cell-free medium and immediately measured (B). Corresponding cytokine levels of MIP-1α (n=4, 4, 3, 4, 3, 3, 3, 3, 3), IFN-γ (n=4, 4, 3, 4, 3, 4, 4, 4, 4), IL-2 (n=4, 4, 3, 4, 3, 3, 3, 3) and TNF-α (n=4, 4, 3, 4, 3, 3, 3, 3) (C). UT-T served as control. FIGS. 26D and 26E show co-cultures of hCART19 and Raji with or without CHX were stimulated with 15 ng ml⁻¹ of epinephrine in vitro. Levels of catecholamines (n=3, 3, 3, 3, 3, 3, 3, 3, 3, 3, 3, 1, 1) (D) and indicated human cytokines (n=3) (E) were measured after 24 hours. Data are presented as mean±s.d. with individual data points shown, analysed by two-tailed t-test.

Figure 27C:
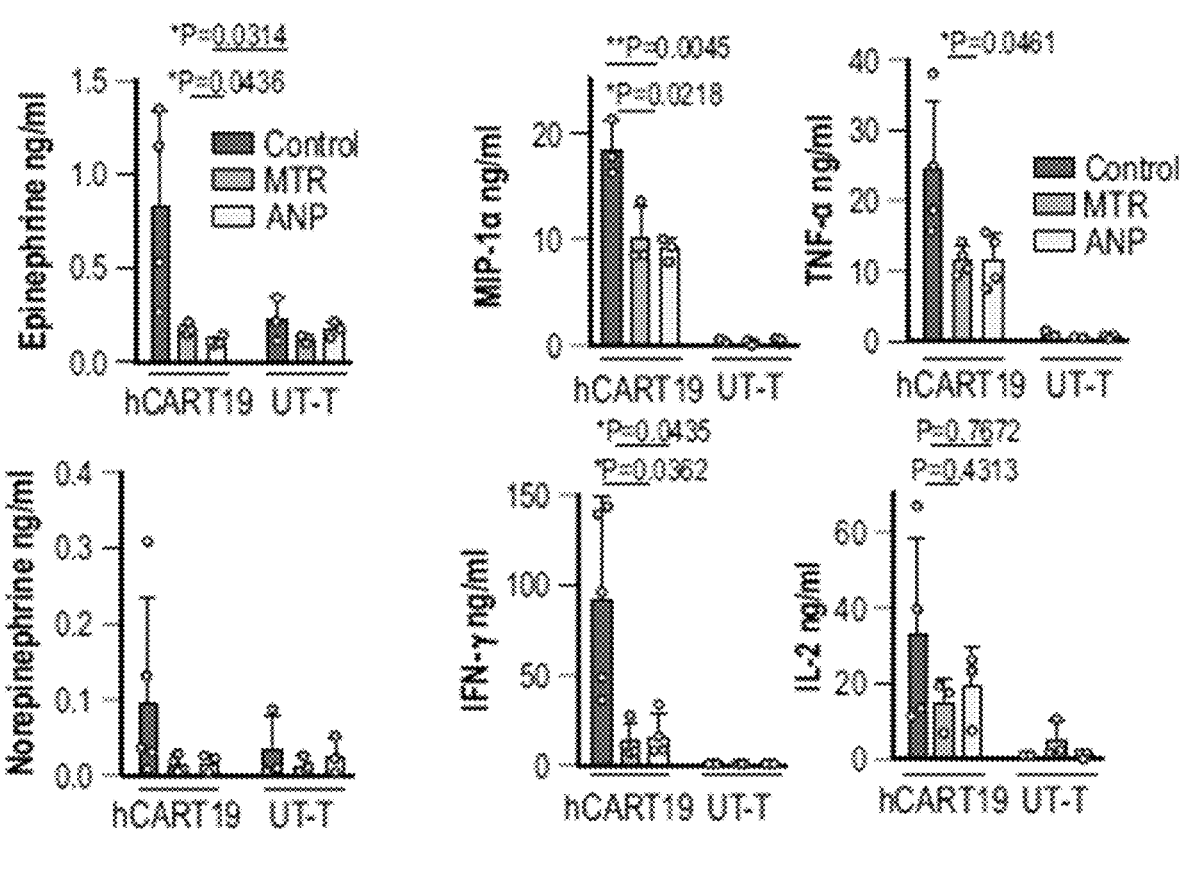
Figure 27C:
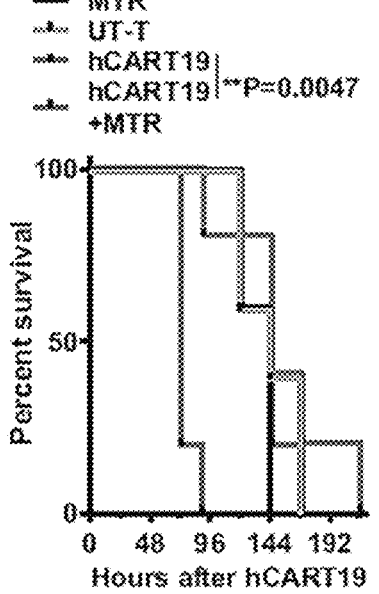
Figures 27D, 27E:
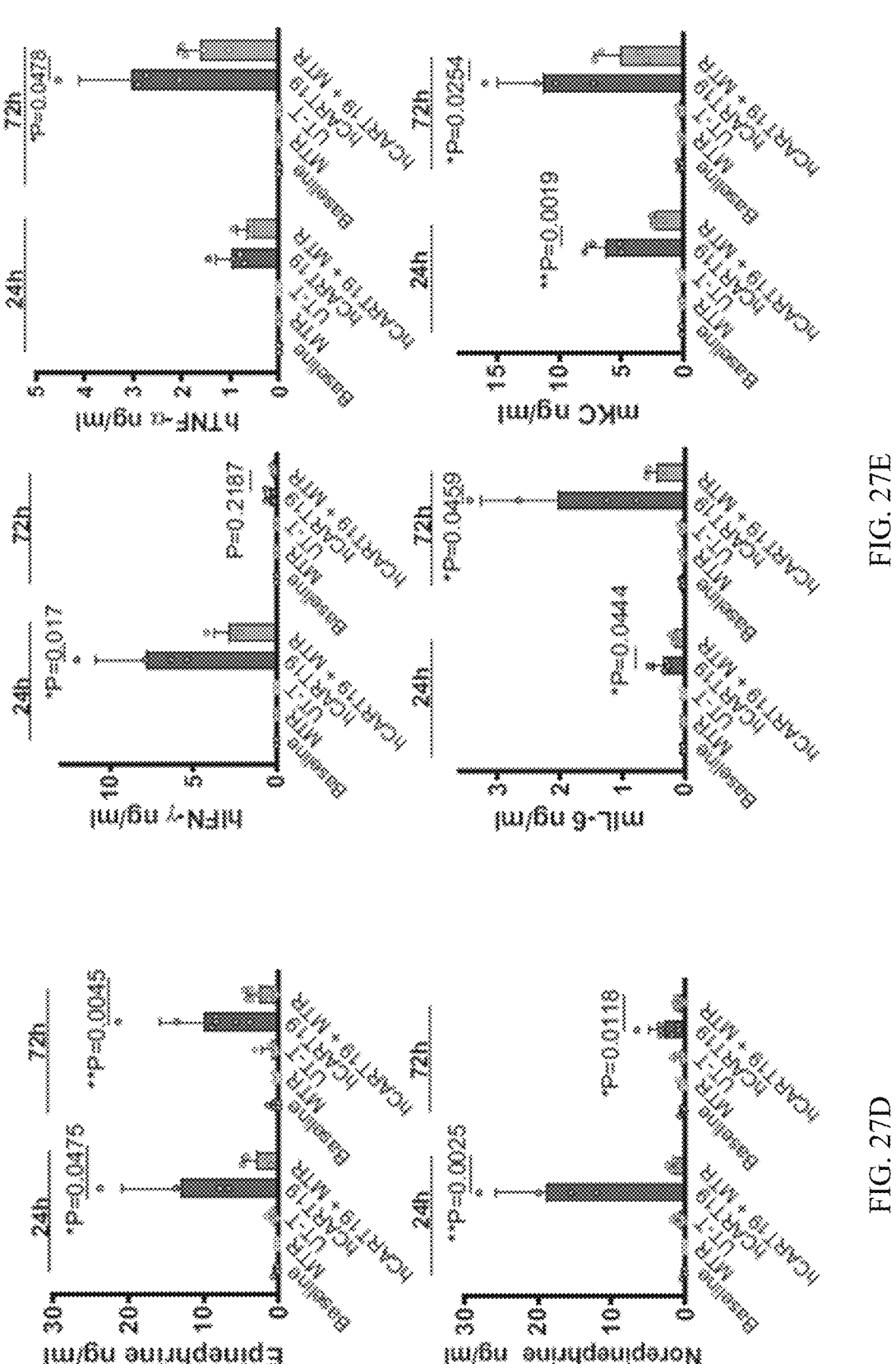

FIGS. 27A-27E show inhibition of catecholamine production reduces cytokine release from activated hCART19. FIGS. 27A and 27B show levels of epinephrine (left to right, n=4, 4, 4, 3, 3, 3 per column) and norepinephrine (n=4, 4, 3, 3, 3, 3) (A) and corresponding cytokines MIP-1α (n=3), TNF-α (n=4, 4, 4, 3, 3, 3), IFN-γ (n=4, 4, 4, 3, 3, 3) and IL-2 (n=4, 3, 3, 3, 3, 3) (B) in the supernatant 24 hours after incubation of Raji cells with hCART19 or UT-T (ratio 1:5), with or without MTR or ANP. FIG. 27C shows Kaplan Meier curves showing the survival of Raji-bearing NSGS mice with high tumour burden, treated with 1.5×10⁷ hCART19, with or without MTR pre-treatment compared to UT-T, MTR and no treatment (n=5 mice per group). Survival differences were evaluated by two-sided log-rank test. FIG. 27D and FIG. 27E shows levels of circulating epinephrine and norepinephrine (n=3, 3, 5, 4, 4, 5, 4, 5, 7, 8) (D) and of indicated circulating mouse and human cytokines (n=4 samples per group) (E), assessed 24 and 72 hours after administration of hCART19 with or without MTR in comparison to controls. Data in FIGS. 27A, 27B, 27D, and 27E are presented as mean±s.d. with individual data points shown, analysed by two-tailed t-test.

Figures 28A, 28B, 28C:
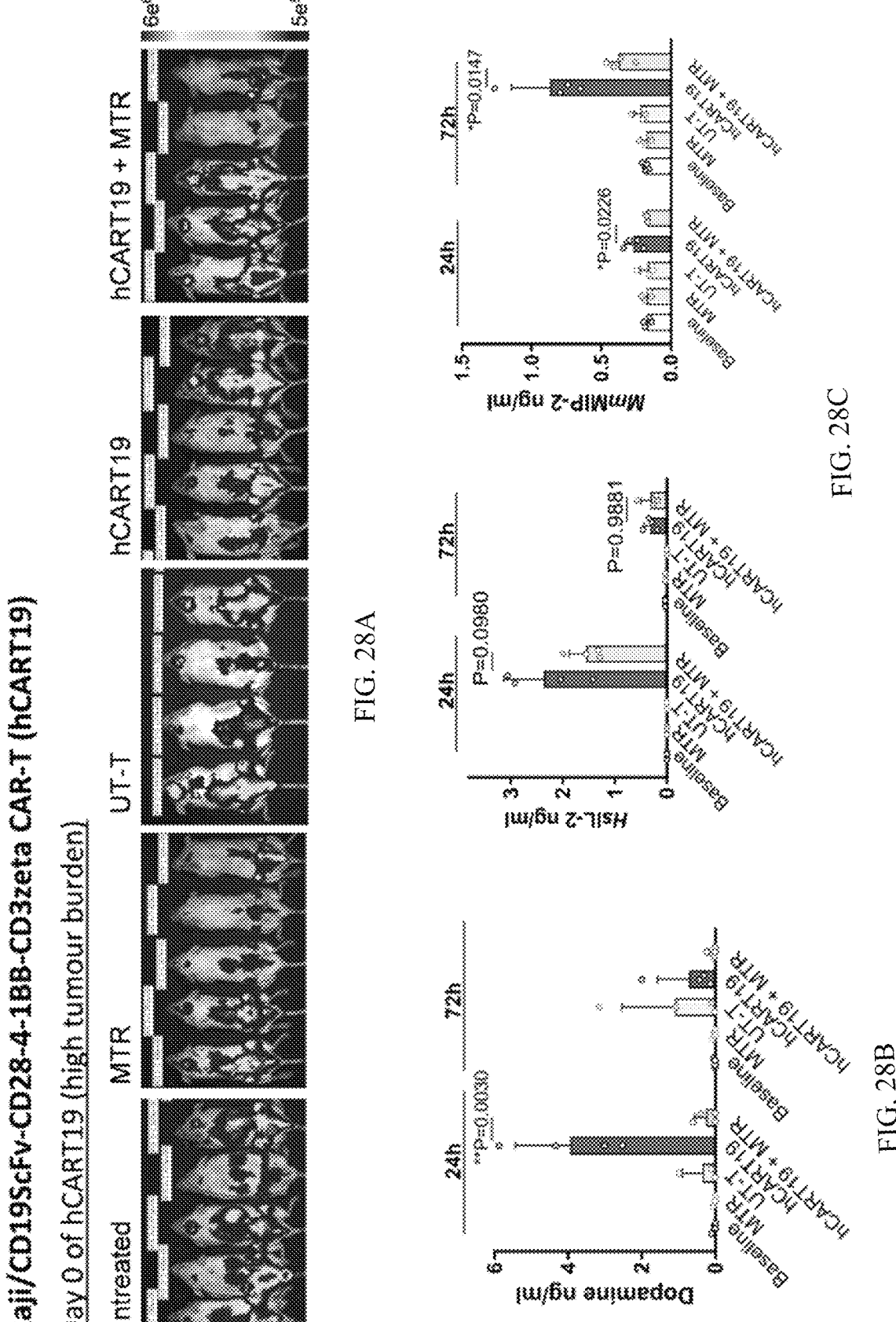
Figure 28D:
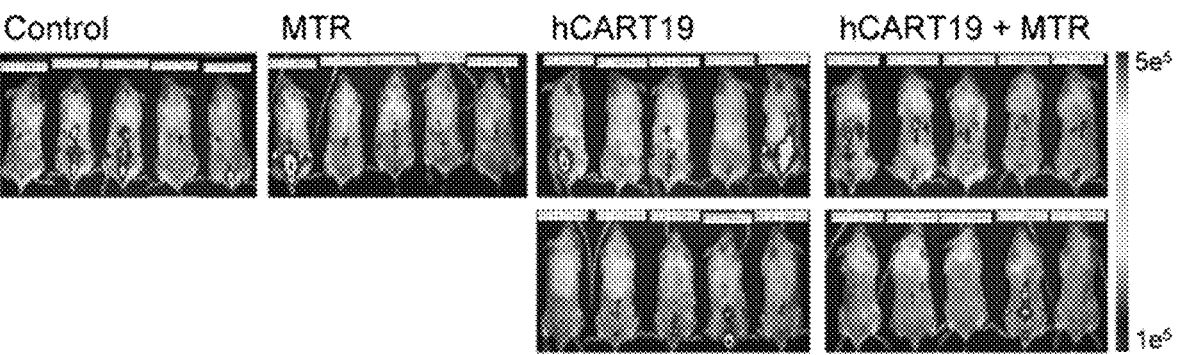
Figure 28D:
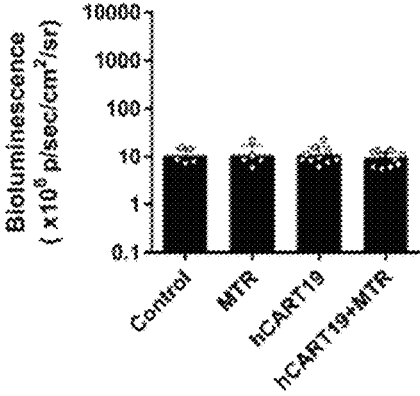
Figure 28G:
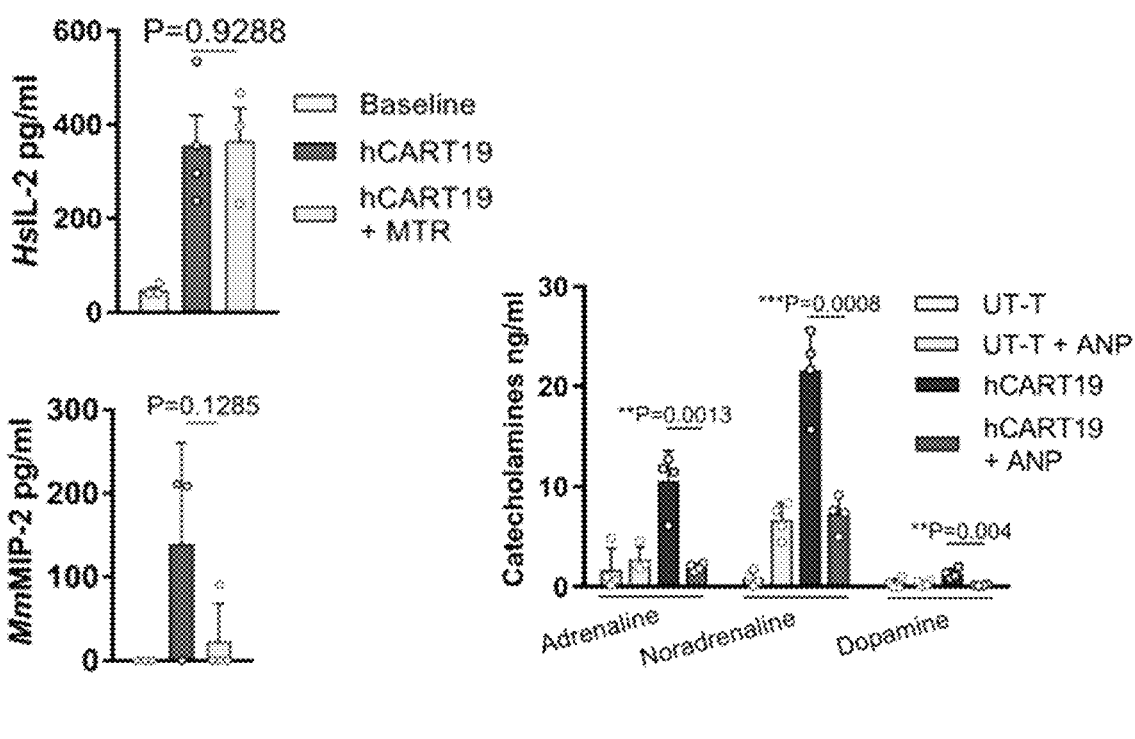
Figure 28G:
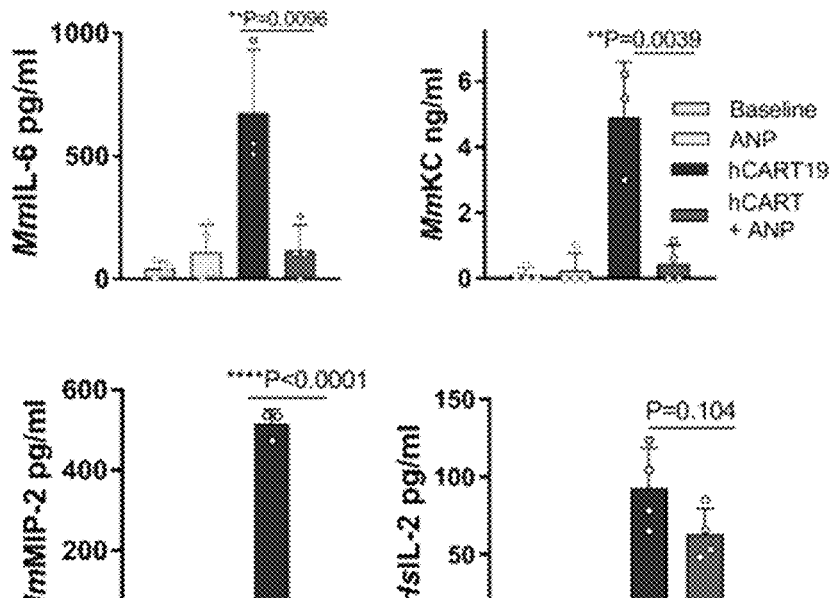
Figure 28H:
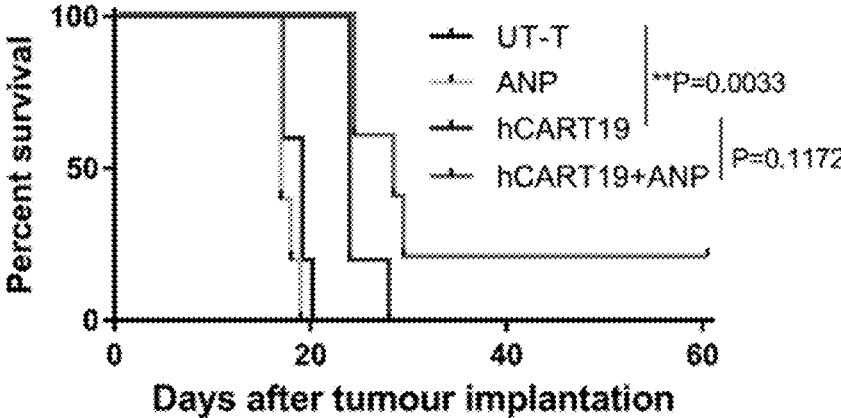
Figure 28I:
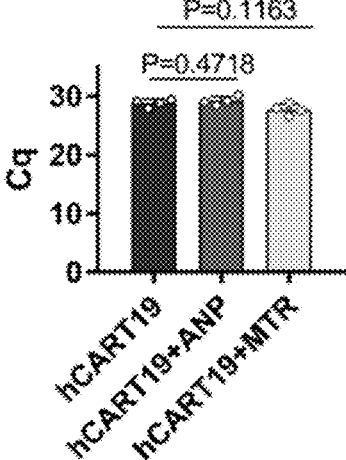

FIGS. 28A-28I show that MTR and ANP prevent cytokine release in Raji/hCART19 mouse model. FIG. 28A shows representative bioluminescent images (BLI) of Raji-bearing NSGS mice with high tumour burden. At day 0, the tumour engraftment was quantified by BLI and mice were randomly assigned to the respective treatment groups (n=5 mice per group). FIGS. 28B and 28C show levels of dopamine (left to right, n=3, 3, 3, 4, 4, 4, 3, 4, 4, 4 per column) (B) and indicated cytokines (n=4) (C) measured in mice (with high tumour burden) 24 and 72 hours after hCART19 and UT-T administration. FIG. 28D shows representative BLI of Raji-bearing NSGS mice with low tumour burden. At day 0, mice were randomly assigned based on tumour burden to receive hCART19, with or without MTR (n=10 mice per group) or UT-T, with or without MTR (n=5 mice per group). FIG. 28E shows levels of human hIL-2 (n=4, 4, 3) and mMIP-2 (n=3, 3, 4) assessed 72 hours after hCART19 injection in mice with low tumour burden. FIGS. 28F and 28G show NSGS mice that were injected with hCART19 4 days after Raji implantation and treated with ANP delivered via subcutaneously implanted osmotic pumps. Levels of circulating catecholamines (n=4 per column) (F) and mIL-6, mKC and mMIP-2 (n=4, 4, 3, 4) as well as hIL-2 (n=4) (G) were assessed 24 hours after hCART19 administration. FIG. 28H shows survival of Raji cell-bearing NSGS mice treated with hCART19 and ANP (n=5 per group); analysed by two-sided log-rank test. FIG. 28I shows level of circulating hCART19 10 days after treatment, determined by $C_q$ by qPCR and analysed in triplicates (n=4 per group). Data in FIGS. 28B, 28C, and 28E-28I are presented as mean±s.d. with individual data points shown, analysed by two-tailed t-test.

Figure 29A:
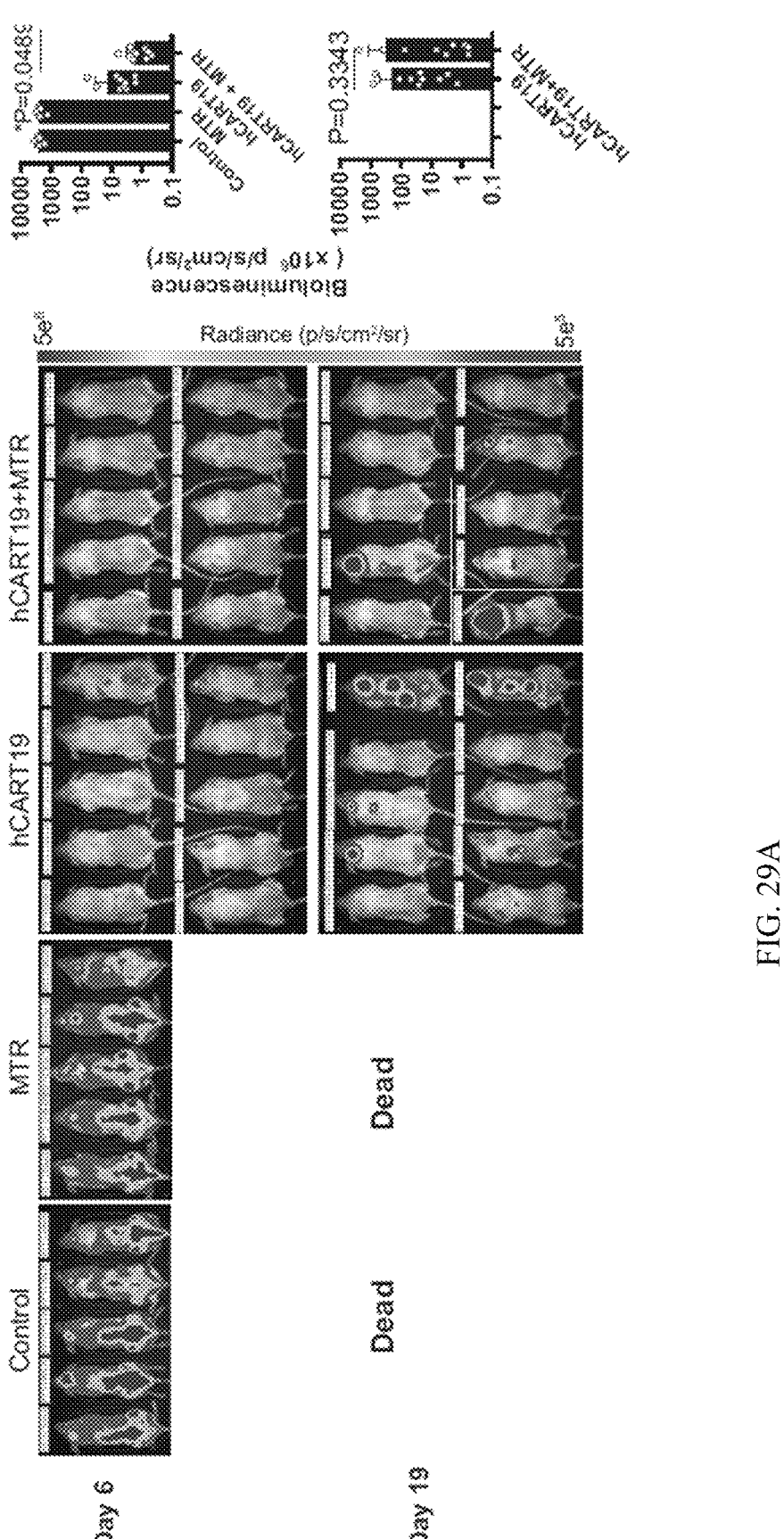
Figure 29B:
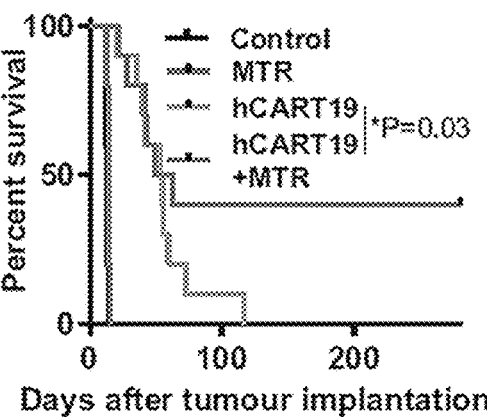
Figure 29C:
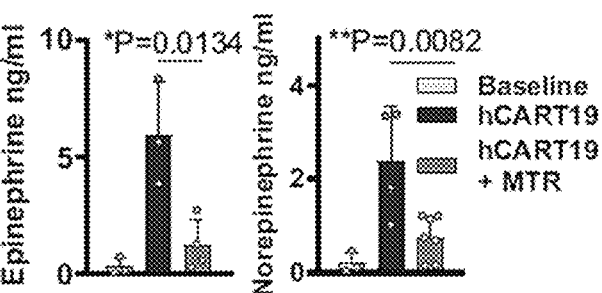
Figure 29D:
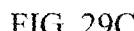
Figure 29D:
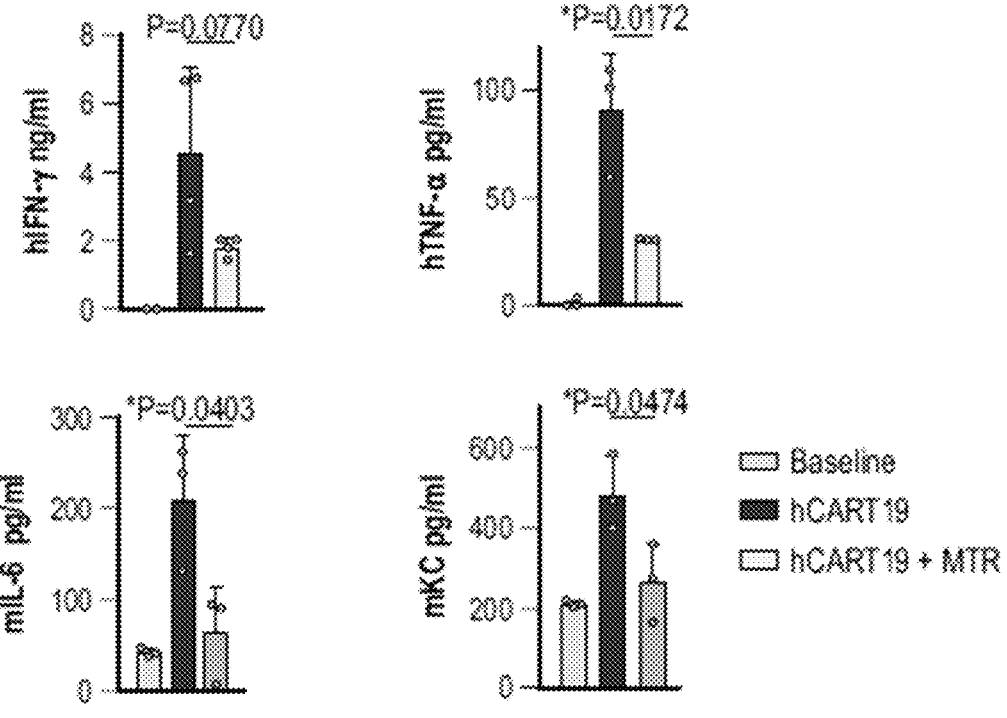

FIGS. 29A-29D show inhibition of catecholamine synthesis with metyrosine does not impair the therapeutic response of hCART19. FIG. 29A shows serial bioluminescence imaging (BLI) of Raji-bearing NSGS mice (low tumor burden) at day 6 and 19 after treatment with 1.5×10⁷ hCART19, with or without MTR (n=10 mice per group) compared to control (UT-T), with or without MTR (n=5 mice per group). BLI counts were used to quantify the tumour burden during the treatment course (right). Statistical differences were evaluated by one-tailed t-test. FIG. 29B shows Corresponding Kaplan-Meier curve of Raji-bearing NSGS mice with low tumour burden, treated with 1.5×10⁷ hCART19, with or without MTR pre-treatment (n=10 mice per group) in comparison to control (UT-T), with or without MTR (n=5 mice per group). Survival differences were analysed by weighted log-rank test. FIGS. 29C and 29D show Levels of plasma epinephrine (n=3, 3, 4 per column) and norepinephrine (n=3, 4, 7) (C) and human hIFN-γ (n=4), hTNF-α (n=4, 3, 3), and mouse cytokines mIL-6 (n=3) and KC (n=3) (D), assessed 72 hours after hCART19 treatment. Data are presented as mean±s.d. with individual data points shown, analysed by two-tailed t-test.

Figures 30A, 30B:
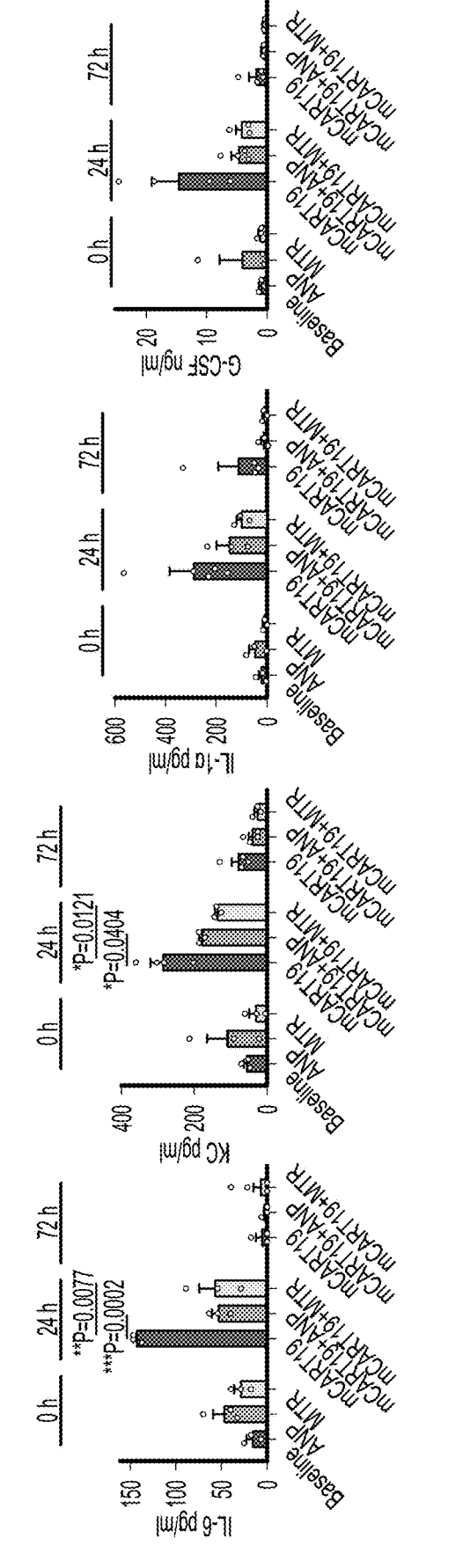
Figure 30C:
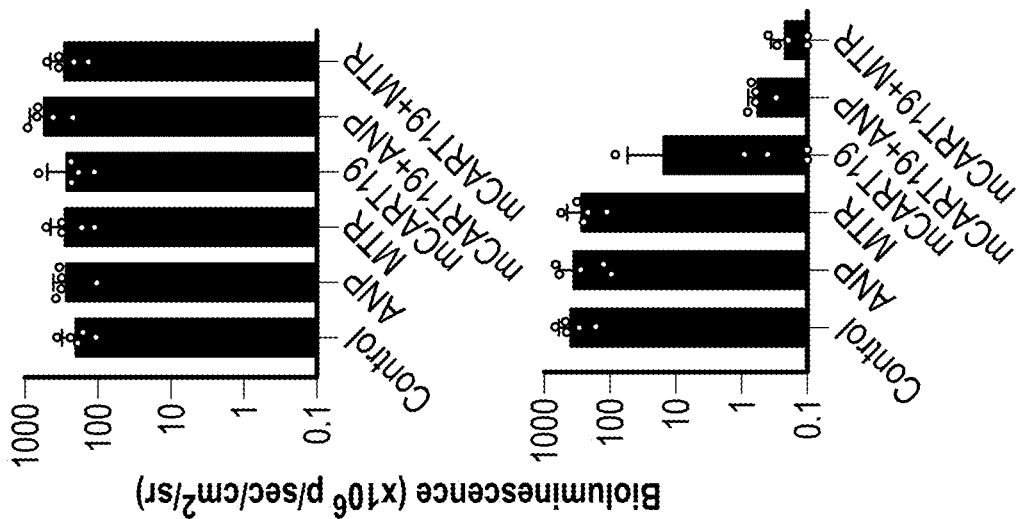
Figure 30D:
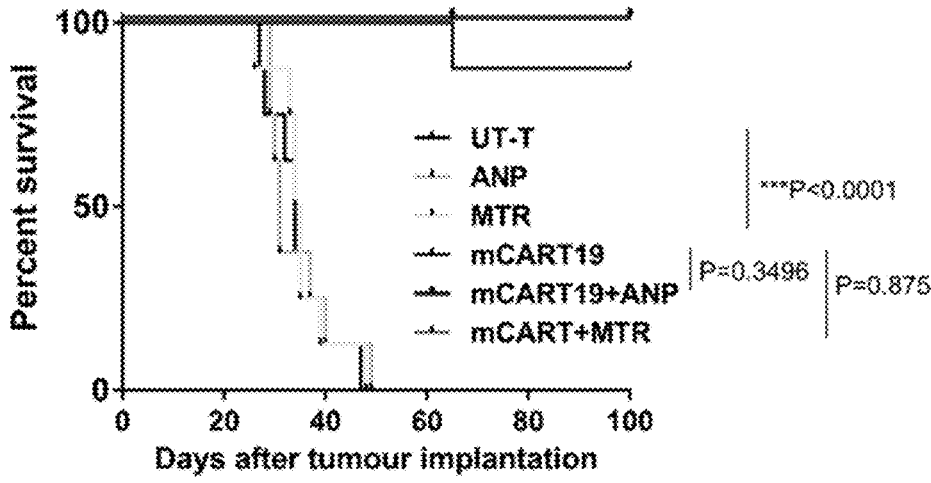

FIGS. 30A-30D show metyrosine and ANP prevent cytokine release in syngeneic Eμ-ALL model without compromising antitumor efficacy. FIG. 30A and FIG. 30B show circulating catecholamines (left to right, n=3, 4, 3, 4, 4, 4, 3, 4, 3, 4, 4, 4 per column/graph) (A) and murine cytokines IL-6 (n=3 per column), KC (n=3, 3, 3, 4, 3, 3, 4, 4, 3 per column), IL-1a (n=3, 3, 3, 3, 3, 4, 3, 3 per column) and GCSF (n=3, 3, 3, 4, 4, 3, 4, 3, 3 per column) (B), assessed at 24 and 72 hours after mCART19 injection. Data are presented as means±s.d. with individual data points shown, analysed by two-tailed t-test. FIG. 30C shows BLI performed before and 10 days after mCART19 cell injection, with or without ANP and MTR pre-treatment (n=5 animals per group). Quantification of BLI radiance was used as a surrogate measurement of tumour burden during the treatment course (right). FIG. 30D shows percentage survival of Ep-ALL-mice after mCART19 cell transfer (n=8 mice per group). Survival differences were analysed by two-sided log-rank test.

DETAILED DESCRIPTION

This document provides methods and materials for treating and/or preventing CRS. For example, this document provides methods and materials for using one or more catecholamine inhibitors to treat a mammal having CRS. For example, this document provides methods and materials for using one or more catecholamine inhibitors to prevent CRS in a mammal at risk of developing CRS. As used herein, a "catecholamine inhibitor" can be any agent that can disrupt a catecholamine response loop (see, e.g., FIG. 15). For example, a catecholamine inhibitor can be an agent capable of suppressing catecholamine synthesis. For example, a catecholamine inhibitor can be an agent capable of blocking an adrenergic receptor. Examples of agents that can be used to disrupt the catecholamine synthesis loop include, without limitation, natriuretic peptides, tyrosine hydroxylase inhibitors (e.g., metyrosine), agents that accelerate catecholamine degradation, agents that block catecholamine release, agents that block adrenergic receptors (e.g., prazosin), and any other agents that interrupt this catecholamine response loop by unknown mechanisms.

In some cases, one or more catecholamine inhibitors described herein (e.g., natriuretic peptides, tyrosine hydroxylase inhibitors, and/or agents that blocks adrenergic receptors (e.g., an α1 adrenergic receptor)) can be used to reduce and/or eliminate cytokine and/or chemokine release. A cytokine and/or chemokine can be a pro-inflammatory cytokine. Examples of cytokines and chemokines include, without limitation, tumor necrosis factor-alpha (TNF-α), interleukin 1 beta (IL-1β), interleukin 6 (IL-6), interleukin 10 (IL-10), interleukin 1 receptor antagonist (IL-1RA), interferon gamma (IFNγ), CXCL1 (KC), macrophage inflammatory protein 2 (MIP-2), macrophage inflammatory protein 1 beta (MIP-1β), and granulocyte-colony stimulating factor (G-CSF). For example, the methods and materials provided herein can be used to reduce and/or eliminate production of IL-6, IFNγ, TNF-α, KC, MIP-2, and MIP-1β.

In some cases, one or more catecholamine inhibitors described herein (e.g., natriuretic peptides, tyrosine hydroxylase inhibitors, and/or agents that blocks adrenergic receptors (e.g., an α1 adrenergic receptor)) can be used to reduce and/or eliminate cytokine and/or chemokine release from any appropriate type of cell. A cell can be an in vivo cell. A cell can be an in vitro cell. Examples of cell types include, without limitation, myeloid cells (e.g., activated myeloid cells), granulocytes, monocytes, T cells (e.g., activated T cells), and macrophages.

In some cases, one or more catecholamine inhibitors described herein (e.g., natriuretic peptides, tyrosine hydroxylase inhibitors, and/or agents that blocks adrenergic receptors (e.g., an α1 adrenergic receptor)) can be used to reduce and/or eliminate catecholamine synthesis. Examples of catecholamines include, without limitation, epinephrine (EPI), norepinephrine (NE), and L-Dopamine (DOP). For example, the methods and materials provided herein can be used to inhibit EPI synthesis.

When treating and/or preventing CRS as described herein, the CRS can be any appropriate type of CRS. In some cases, CRS can be associated with an infection. Examples of CRS-associated infections include, without limitation, bacterial infections (e.g., gram-positive bacterial infections and gram-negative bacterial infections), polymicrobial infections, viral infections (e.g., Ebola infections, avian influenza infections, and smallpox infections. In some cases, CRS can be associated with administration of an immunotherapy. Immunotherapy can be a cancer immunotherapy. Examples of immunotherapies include, without limitation, antibody therapies (e.g., orthoclone OKT3, muromonab-CD3, rituximab, alemtuzumab, ipilimumab, nivolumab, ofatumumab, CP-870,893, LO-CD2a/BTI-322, or TGN1412), chimeric antigen receptor therapies (CAR-T; e.g., tisagenlecleucel or axicabtagene ciloleucel), bi-specific T-cell engagers (BiTEs), cellular immunotherapies (e.g., adoptive T-cell therapy or dendritic cell therapy), cytokine therapies (e.g., interferon therapy and interleukin therapy), and microorganism therapies (e.g., bacterial therapy or viral therapy). In cases where CRS is associated with an immunotherapy, and the immunotherapy is CAR-T, the CAR-T can target any of a variety of antigens (e.g., CD19, CD20, CD22, CD30, CEA, EGFR, EGP-2, EGP-40, erb-B2 (also referred to as Her2/neu), FBP, fetal acetylcholine receptor, GD2, GD3, IL-13R-a2, KDR, k-light chain, LeY, MAGE-A1, MUC1, NKG2D ligands, oncofetal antigen (h5T4), PSCA, PSMA, TAG-72, and VEGF-R2). In cases where CRS is associated with an immunotherapy, and the immunotherapy is CAR-T, the CAR-T can be as described elsewhere (see, e.g., Ruella et al., 2016 Curr Hematol Malig Rep., 11:368-84). In cases where CRS is associated with microorganism therapy, the microorganism therapy can use live microorganisms, attenuated microorganisms, inactivated microorganisms, or any combination thereof. In some cases, CRS can be associated with a treatment (e.g., an immunotherapeutic agent) for an autoimmune disease. Examples of autoimmune diseases include, without limitation, rheumatoid arthritis (RA), juvenile idiopathic arthritis (JIA), ankylosing spondylitis, psoriasis, systemic lupus erythematosus (SLE), celiac disease, type 1 diabetes, autoimmune encephalomyelitis, multiple sclerosis, central nervous system (CNS) autoimmune demyelinating diseases, chronic inflammatory demyelinating polyneuropathy (CIDP), transverse myelitis, polymyositis, dermatomyositis, inflammatory bowel disease (e.g. Crohn's disease and ulcerative colitis), autoimmune hemolytic anemia, autoimmune cardiomyopathy, autoimmune thyroiditis, Graves' disease, Sjogren's syndrome, Goodpasture syndrome, autoimmune pancreatitis, Addison's disease, alopecia, myasthenia gravis, sarcoidosis, scleroderma, pemphigus vulgaris, mixed connective tissue disease, bullous pemphigoid, and vitiligo. In some cases, CRS can be associated with transplant rejection (e.g., organ rejection, allograft rejection, host-versus-graft disease, and graft-versus-host disease (GVHD)).

In cases where CRS is associated with transplant rejection, the methods and materials provided herein can be used to treat and/or prevent transplant rejection. For example, one or more catecholamine inhibitors described herein (e.g., natriuretic peptides, tyrosine hydroxylase inhibitors, and/or agents that blocks adrenergic receptors (e.g., an α1 adrenergic receptor)) can be used to treat and/or prevent transplant rejection. When treating and/or preventing transplant rejection as described herein, the transplant can be any appropriate transplant (e.g., organ (e.g., heart, lung, kidney, and liver) transplants, tissue (e.g., skin, cornea, and blood vessels) transplants, and cell (e.g., bone marrow and blood) transplants). A transplant can include an allograft. A transplant can include a xenograft. Transplant rejection can be chronic or acute. Examples of types of transplant rejection include, without limitation, organ rejection, allograft rejection, host-versus-graft disease, and GVHD. For example, the methods and materials provided herein can be used to treat and/or prevent GVHD.

Any type of mammal having CRS or at risk for developing CRS can be treated as described herein. Examples of mammals that can be treated with one or more catecholamine inhibitors described herein (e.g., natriuretic peptides, tyrosine hydroxylase inhibitors and/or agents that blocks adrenergic receptors (e.g., an α1 adrenergic receptor)) include, without limitation, humans, non-human primates (e.g., monkeys), dogs, cats, horses, cows, pigs, sheep, rabbits, mice, and rats. For example, humans having CRS or at risk of developing CRS can be treated with one or more catecholamine inhibitors as described herein.

In some cases, the methods provided herein can include identifying a mammal as having CRS. Any appropriate method can be used to identify a mammal having CRS. For example, detection of elevated levels of cytokines (e.g., IL-6, IFNγ, TNF-α, KC, MIP-2, and/or MIP-1β) can be used to identify a human or other mammal having CRS.

In some cases, the methods provided herein also can include assessing a mammal for risk of developing CRS. Any appropriate method can be used to identify a mammal for risk of developing CRS. For example, detection of elevated levels of catecholamines (e.g., EPI, NE, and DPO) can be used to identify a human or other mammal for risk of developing CRS. In some cases, increased levels of EPI (e.g., in a mammal's serum) can indicate that a mammal is at increased risk of developing CRS. For example, a mammal undergoing or scheduled to undergo immunotherapy can be at risk of developing CRS.

In some cases, a mammal can be identified as being at risk of developing CRS and can be selected for treatment as described herein. For example, a mammal identified as being at risk of developing CRS can be selected for treatment with one or more catecholamine inhibitors described herein (e.g., natriuretic peptides, tyrosine hydroxylase inhibitors, and/or agents that blocks adrenergic receptors (e.g., an α1 adrenergic receptor)).

Once identified as having CRS or as being at risk for developing CRS, a mammal can be administered or instructed to self-administer one or more (e.g., one, two, three, four, five, or more) catecholamine inhibitors described herein (e.g., natriuretic peptides, tyrosine hydroxylase inhibitors, and/or agents that blocks adrenergic receptors (e.g., an α1 adrenergic receptor)). In some cases, a mammal can be identified as being at risk of developing CRS, can be selected for treatment as described herein, and one or more catecholamine inhibitors can be administered to the mammal to treat the mammal.

A catecholamine inhibitor can be any appropriate catecholamine inhibitor. Examples of catecholamine inhibitors include, without limitation, reserpine, tyramine, octopamine, guanethidine, guanadrel, amphetamine, ephedrine, pseudoepherine, phenylpropanolamine, methylphenidate, cocaine, tricyclic antidepressants, phenelzine, ipraniazide, tranylcyproamine, clorgyline-befloxatone, and selegiline.

In some cases, a catecholamine inhibitor can be a natriuretic peptide. A natriuretic peptide can be any appropriate natriuretic peptide. Examples of natriuretic peptides include, without limitation, atrial natriuretic peptide (ANP), brain natriuretic peptide (BNP), C-type natriuretic peptide (CNP), and dendroaspis natriuretic peptide (DNP). For example, a natriuretic peptide can be ANP. ANP can be a human ANP. In some cases, a natriuretic peptide can be administered as a mature natriuretic peptide polypeptide. In some cases, a natriuretic peptide can be administered as a precursor peptide (e.g., prepro-ANP). An exemplary human ANP polypeptide can include the amino acid sequence SLRRSSCFG-GRMDRIGAQSGLGCNSFRY (SEQ ID NO:1). A natriuretic peptide can include a peptide ring (e.g., a 17-amino acid peptide ring) formed by a disulfide bond between two cysteine residues within the natriuretic peptide amino acid sequence (e.g., at cysteine residues positions 7 and 23 of SEQ ID NO:1). A natriuretic peptide can bind to one or more natriuretic peptide receptors. Examples of natriuretic peptide receptors include, without limitation, guanylyl cyclase-A (GC-A; also known as natriuretic peptide receptor-A (NPRA/ANPA) or NPR1), guanylyl cyclase-B (GC-B; also known as natriuretic peptide receptor-B (NPRB/ANPB) or NPR2), and natriuretic peptide clearance receptor (NPRC/ANPC) or NPR3). In some cases, a human ANP polypeptide can have a sequence that deviates from the ANP polypeptide sequence set forth in SEQ ID NO:1, sometimes referred to as a variant sequence, provided the ANP polypeptide maintains its structure (e.g., a peptide ring formed by a disulfide bond between two cysteine residues) and function (e.g., binding to one or more atrial natriuretic peptide receptors. For example, an ANP polypeptide can have at least 80 (e.g., at least 85, at least 90, at least 95, at least 98, or at least 99) percent sequence identity to SEQ ID NO:1 (e.g., while maintaining the cysteine residues positions 7 and 23 of SEQ ID NO:1). For example, an ANP polypeptide can have one or more (e.g., 2, 3, 4, 5, 6, 7, 8, 9, or 10) amino acid modifications (e.g., substitutions) relative to SEQ ID NO:1. In some cases, a natriuretic peptide can be administered as a nucleic acid (e.g., cDNA) encoding a natriuretic peptide polypeptide. An exemplary human ANP nucleic acid (e.g., a coding sequence or a cDNA) can include the nucleic acid sequence TCAT-TAAGAAGATCTTCATGTTTTGGAGGAAGAATGGA-TAGAATAGGAGCTCAA TCAGGATTAGGATGTAATT-CATTCAGATATTAA (SEQ ID NO:2). A human ANP nucleic acid can have a sequence that deviates from the ANP nucleic acid sequence set forth in SEQ ID NO:2, sometimes referred to as a variant sequence, provided the ANP nucleic acid encodes an ANP polypeptide. An ANP nucleic acid can have at least 80 (e.g., at least 85, at least 90, at least 95, at least 98, or at least 99) percent sequence identity to SEQ ID NO:2. An ANP nucleic acid can have one or more (e.g., 2, 3, 4, 5, 6, 7, 8, 9, or 10) nucleotide modifications (e.g., substitutions) relative to SEQ ID NO:2.

In some cases, a catecholamine inhibitor can be a tyrosine hydroxylase inhibitor. A tyrosine hydroxylase inhibitor can be any appropriate tyrosine hydroxylase inhibitor. A tyrosine hydroxylase inhibitor can be an inhibitor of tyrosine hydroxylase polypeptide expression or an inhibitor of tyrosine hydroxylase polypeptide activity. Examples of compounds that reduce tyrosine hydroxylase polypeptide activity include, without limitation, metyrosine (also known as methyltyrosine and/or metirosine (MTR); e.g., α-MTR), alpha-methyl-p-tyrosine (AMPT), aquayamycin, bulbocapnine, 2-hydroxyestradiol, 2-hydroxyestrone, 3-iodotyrosine, and oudenone. Examples of compounds that reduce tyrosine hydroxylase polypeptide expression include, without limitation, nucleic acid molecules designed to induce RNA interference (e.g., a siRNA molecule or a shRNA molecule), antisense molecules, and miRNAs. For example, a tyrosine hydroxylase inhibitor can be MTR.

In some cases, a catecholamine inhibitor can accelerate catecholamine degradation. Examples of agents that can accelerate catecholamine degradation include, without limitation, monoamine oxidases (MAOs; e.g., MAO-A and MAO-B), MAO activators (e.g., glucocorticoids), catechol-O-methyltransferases (COMTs), and COMT activators. Additional examples of agents that can accelerate catecholamine degradation can be as described elsewhere (see, e.g., Camell et al., 2017 Nature, 550:119-123).

In some cases, a catecholamine inhibitor can block the release of catecholamines (e.g., from cells that produce catecholamines). Examples of agents that can block catecholamine release include, without limitation, gabapentin (see, e.g., Todd et al., 2012 Anesthesiology. 116:1013-1024).

In some cases, a catecholamine inhibitor can block adrenergic receptors (e.g., adrenoceptors). An adrenergic receptor can be any appropriate type of adrenergic receptor (e.g., an alpha (α) 1, α2, beta (β) 1, or β2 adrenergic receptor). Examples of agents that can block adrenergic receptors include, without limitation, alpha-1 blockers (e.g., acepromazine, alfuzosin, doxazosin, phenoxybenzamine, phentolamine, prazosin, tamsulosin, terazosin, and trazodone), alpha-2 blockers (e.g., phentolamine, yohimbine, idazoxan, atipamezole, and trazodone), and beta blockers (e.g., propranolol, atenolol, metoprolol, bisoprolol, timolol, nebivolol, vortioxetine, butoxamine, ICI-118,551, and SR 59230A). In some cases, a catecholamine inhibitor can block an α1 adrenergic receptor. Additional examples of agents that can block adrenergic receptors can be as described elsewhere (see, e.g., Sigola et al., 2000 Immunology, 100: 359-63).

In some cases, a catecholamine inhibitor can include both a natriuretic peptide (e.g., ANP) and a tyrosine hydroxylase inhibitor (e.g., MTR). For example, a catecholamine inhibitor can include ANP and MTR. In some cases, a catecholamine inhibitor can include both a natriuretic peptide (e.g., ANP) and an agent that blocks an adrenergic receptor (e.g., an α1 adrenergic receptor, e.g., prazosin). For example, a catecholamine inhibitor can include ANP and prazosin. In some cases, a catecholamine inhibitor can include both a tyrosine hydroxylase inhibitor (e.g., MTR) and an agent that blocks an adrenergic receptor (e.g., an α1 adrenergic receptor, e.g., prazosin). For example, a catecholamine inhibitor can include MTR and prazosin. In some cases, a catecholamine inhibitor can include a natriuretic peptide (e.g., ANP), a tyrosine hydroxylase inhibitor (e.g., MTR), and an agent that blocks an adrenergic receptor (e.g., an α1 adrenergic receptor, e.g., prazosin). For example, a catecholamine inhibitor can include ANP, MTR, and prazosin.

One or more catecholamine inhibitors described herein (e.g., natriuretic peptides, tyrosine hydroxylase inhibitors, and/or agents that blocks adrenergic receptors (e.g., an α1 adrenergic receptor)) can be formulated into a composition (e.g., a pharmaceutically acceptable composition) for administration to a mammal having CRS or as being at risk for developing CRS. For example, a therapeutically effective amount of one or more catecholamine inhibitors described herein can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules.

A composition (e.g., a pharmaceutically acceptable composition) including one or more catecholamine inhibitors described herein (e.g., natriuretic peptides, tyrosine hydroxylase inhibitors, and/or agents that blocks adrenergic receptors (e.g., an α1 adrenergic receptor)) can be administered locally or systemically. A composition containing one or more catecholamine inhibitors described herein can be designed for oral, parenteral (including subcutaneous, intramuscular, intravenous, and intradermal), or inhaled administration. For example, a composition containing one or more catecholamine inhibitors described herein can be administered systemically by an oral administration to or inhalation by a mammal (e.g., a human). When being administered orally, a composition containing one or more catecholamine inhibitors described herein can be in the form of a pill, tablet, or capsule.

One or more catecholamine inhibitors described herein (e.g., natriuretic peptides, tyrosine hydroxylase inhibitors, and/or agents that blocks adrenergic receptors (e.g., an α1 adrenergic receptor)) can be administered to a mammal having CRS or as being at risk for developing CRS as a combination therapy with one or more additional agents/therapies used to treat CRS. For example, a combination therapy can include administering to the mammal (e.g., a human) one or more catecholamine inhibitors described herein together with one or more CRS treatments such antibiotics (e.g., metronidazole and dexamethasone), antihistamines (e.g., chlorphenamine), corticosteroids (e.g., hydrocortisone), fever reducers (e.g., acetaminophen), hydration, and/or correcting overhydration (e.g., by dialysis or with furosemide (e.g., intravenous furosemide)). In cases where one or more therapeutic agents described herein are used in combination with one or more additional agents/therapies used to treat CRS, the one or more additional agents/therapies used to treat CRS can be administered at the same time or independently. For example, the composition including one or more therapeutic agents can be administered first, and the one or more additional agents/therapies used to treat CRS administered second, or vice versa.

The invention will be further described in the following examples, which do not limit the scope of the invention described in the claims.

EXAMPLES

Example 1: Preventing Mortality from Therapy-Induced Cytokine Release Syndrome

Materials and Methods

Mice

All animal works were performed in accordance to the protocol of Johns Hopkins Animal Care and Use Committee (ACUC). For subcutaneous CT26 tumor implantation, LPS and CLP experiments, female C57BL/6 and BALB/C mice of 6-8 weeks were purchased from Harlan Laboratories. For anti-mCD3 treatment, female BALB/C mice of 5-6 months old were purchased form Harlan laboratories. For the CART19 treatment, NSG-SGM3 (NSGS) mice (Stock no. 013062) were purchased from The Jackson Laboratory.

Chemicals and Reagents

For immunofluorescent staining, Alexa Fluor 594 goat anti-mouse and 488 goat anti-rabbit IgG were purchased from Invitrogen. Anti-mCD3 (145-2C11) and anti-Ly6G (8C5) antibodies were purchased from Bio X Cell. α-methyl-D,L-p-tyrosine methyl ester hydrochloride (Santa Cruz Biotechnology, SC-219470) is a soluble from of α-methyl-tyrosine (metyrosine) that is converted to α-methyl-tyrosine in vivo (see, e.g., Corrodi et al., 1966 *Psychopharmacologia,* 10:116). LPS from *Escherichia coli* 0111:B4 (L2630), (−)-epinephrine (E4250) and human ANP (A1663) were purchased from Sigma.

Strain Engineering of *C. novyi*-NT

The site-specific knock-in of hANP in *C. novyi*-NT employed the TargeTron Gene Knockout System (Sigma), which is based on the retrohoming mechanism of group II introns (see, e.g., Kuehne et al., 2012 *Bioengineered,* 3:247). The sequence of the human ANP cDNA was optimized for *Clostridium* codon usage as TCATTAAGAAGATCTT-CATGTTTTGGAGGAAGAATGGATAGAATAGGAGCT-CAA TCAGGATTAGGATGTAATTCATTCAGATATTAA (SEQ ID NO:2) coding for 28 AA (SLRRSSCFGGRMDRI-GAQSGLGCNSFRY; SEQ ID NO:1). The synthesized sequence was cloned into the shuttle vector pMTL8325. The construct included the *C. novyi* PLC signal peptide sequence under the control of the *C. novyi* flagellin promoter. Subsequently, the MluI fragment of the construct was subcloned into the vector pAK001 (pMTL8325-pJIR750ai Reverse-pFla-153s-MCS-pThio-G1-ErmB) targeting the knock-in in the 153s site of *C. novyi*-NT genome. The *E. coli* CA434 strain containing the targeting construct was conjugated with *C. novyi*-NT and selected with polymyxin B/erythromycin (Sigma) under anaerobic condition. Colonies were selected and re-plated three times on non-selection plates and again on the erythromycin plate. Clones were tested first by PCR using EBS Universal and 153S-F primers. Positive clones were further tested by PCR with primers targeting the backbone of the vector to confirm the insert was integrated in *C. novyi* genome and with primers covering externally both sides of 153S to confirm the correct insertion. The propagation and sporulation of *C. novyi*-NT strains followed procedures described elsewhere (Bettegowda et al., 2006 *Nature Biotechnology,* 24:1573-80).

ANP Measurement and cGMP Assay

ANP concentrations in the supernatant of ANP-*C. novyi*-NT culture and in mouse plasma were measured by an Elisa kit from Ray Biotech (EIAR-ANP-1) that recognizes both human and mouse ANP. ANP in the supernatant of ANP-*C. novyi*-NT culture were shown biological activities as described elsewhere (Lofton et al., 1990 *Biochem. Biophys. Res. Comm.,* 172:793-9). Briefly, bacterial supernatants were applied to cultured bovine aortic endothelial cells (BAOEC, Cell Applications Inc.) for 3 minutes. cGMP concentrations were then measured in BAOEC lysates by the Direct cGMP Elisa Kit from Enzo following the manufacture's instruction.

Subcutaneous Tumor Models and *C. novyi* Therapy

The colon cancer cell line CT26 was injected subcutaneously into the right flank of six to eight week old female Balb/C mice as described elsewhere (Qiao et al., 2011 *Oncotarget,* 2:59-68). Tumor sizes were measured with a caliper and calculated as ½*L*W*H as described elsewhere (Tomayko et al., 1989 *Can. Chemother. Pharmacol.,* 24:148-54). When tumors reached 600-900 mm$^3$ after about two weeks, $12\times10^6$ spores of *C. novyi*-NT or ANP-*C. novyi*-NT at $3\times10^6/\mu l$ were injected intratumorally into 4 central parts of the tumor with a 32 G Hamilton syringe needle. The bacteria typical germinated in the tumors within 24 hours, turning them necrotic. Hydration of the mice was supported by daily subcutaneous injections of 500 Id saline. Human ANP (Sigma) was dissolved in saline, loaded in mini-osmotic pumps (ALZET) with a release rate of 12 µg/day and implanted subcutaneously in the back of mice 12 hours before the spore injection. Pumps loaded with saline served as controls. Metyrosine was dissolved in PBS and injected IP at 60 mg/kg/day for three days before the *C. novyi* injection to deplete catecholamines in storage. Two hours after the spore injection, 60 mg/kg of metyrosine was injected intraperitoneally (IP). For each of the next three days, IP injections of metyrosine at 30 mg/kg were administered. Control groups were injected with PBS at the same time points.

Peritoneal Macrophage Experiments

Isolation of elicited macrophages from mouse peritoneum followed previously described procedures with minor modifications (Zhang et al., "The isolation and characterization of murine macrophages," *Curr Protoc Immunol* Chapter 14, Unit 14.1 (November, 2008)). Four days prior to the harvest, 1 ml of 3% Brewer's thioglycollate medium (BD) was injected IP in female 2-3 months old BALB/c mice. Mice were euthanized by cervical dislocation and the skin of the belly was cut open without penetrating the muscle layer. Using a syringe with a 22 G needle, 5 ml of cold PBS containing 5 mM EDTA was injected carefully into the peritoneal cavity. After massaging gently for 1-2 minutes, a 1-ml syringe without needle was used to extract the peritoneal contents containing residential macrophages. Cells were centrifuged at 400 g for 10 minutes at 4° C., resuspended in DMEM/F12 medium supplemented with 1% FBS and antibiotics and distributed in 48-well plates at a concentration of $0.5\times10^6$ cells/well. After incubation at 37° C. for 2 hours, cells were rinsed three times with 0.5 ml media and then 250 µl of media was added to each well. Ten minutes before the addition of LPS or epinephrine, metyrosine at 2 mM or ANP at 5 µg/ml was added to the cells. For stimulation, the cells were incubated for 24 hours with LPS at 50 µg/ml. An initial solution of 3 mg/ml (−)-epinephrine was made with 0.1 N HCl and subsequently diluted with PBS. To stimulate macrophages, they were exposed to epinephrine at 15 ng/ml for 24 hours at 37° C. After the incubation, supernatants were collected from the wells and mixed with 5 mM EDTA and 4 mM sodium metabisulfite for preservation of catecholamines and stored at −80° C. Control experiments showed that all detectable epinephrine was degraded after incubation in media for 24 hours at 37° C. Thus, any epinephrine identified in the media must have been secreted by cells in the last 24 hours prior to harvesting the media.

LPS Experiments in Mice

LPS from *Escherichia coli* 0111:B4 was formulated as a 10 mg/ml solution in water and stored in −80° C. LPS was injected intraperitoneally at a dose of 3.5 mg/kg. This dose was found to be optimal for demonstrating the protective effects of ANP and metyrosine. Human ANP (Sigma) was dissolved in saline, loaded in mini-osmotic pumps (ALZET) with a release rate of 12 µg/day and implanted subcutaneously in the back of mice 12 hours before the LPS injection. Mice implanted with pumps loaded with saline served as controls. Metyrosine was freshly dissolved in PBS and injected IP at 60 mg/kg/day for three days prior to the LPS treatment. One hour before the LPS injection, metyrosine was injected at 60 mg/kg into the lower abdomen contralateral to the side of LPS injection. The control groups were injected with PBS. For the following 3 days, metyrosine was injected at 30 mg/kg/day IP. Hydration of mice was supported by daily subcutaneous injection of 0.5 ml saline.

CLP Experiments

Cecal ligation and puncture (CLP) was performed as described elsewhere (Rittirsch et al., 2009 *Nature Protocols,* 4:31-6). Briefly, six-to-eight week old female C57BL/6 mice were anesthetized and following abdominal incision, the cecum was ligated at about 14 the distance from the luminal entry to its tip. The ligated cecum was punctured through and through with a 22 G needle at ½ and ¾ the distance from the luminal entry to its tip. A small amount of the cecal content was gently pushed out of the four openings into the peritoneum. Subsequently, the abdominal muscles were sutured and the skin was closed with two staples. Five hundred microliters of saline were immediately injected subcutaneously to the mice. For the groups treated with antibiotics, imipenem (Sigma) was injected subcutaneously at 25 mg/kg starting from 20 hours after CLP, with a schedule of twice a day on day one and once a day thereafter for 10 days. Human ANP (Sigma) was dissolved in saline, loaded in mini-osmotic pumps (ALZET) with a release rate of 12 μg/day and implanted subcutaneously in the back of mice 12 hours before the CLP, with pumps loaded with saline serving as controls. Metyrosine was freshly dissolved in PBS and injected IP at 60 mg/kg/day for three days before the CLP. Twenty minutes before the CLP, metyrosine was injected at 60 mg/kg IP into the right side. The control groups were injected with PBS. For the following 4 days, metyrosine was injected at 30 mg/kg/day IP into the right side. Hydration of mice was supported by daily subcutaneous injection of 0.5 ml saline.

Anti-CD3 Treatment

Five to six-month old Female BALB/c mice were used because we observed that young mice treated with anti-CD3 antibodies underwent severe weight loss but did not consistently die, even at very high doses of the anti-CD3 antibody. Metyrosine was freshly dissolved in PBS and injected IP at 60 mg/kg/day for three days prior to injection of anti-CD3 antibodies. Various doses of anti-CD3 antibody were tested, and it was found that 125 μg/mouse resulted in the death of about half the mice; this was the dose chosen for further experiments. Thirty minutes before the IP injection of the anti-mouse CD3 antibody (BioXcell, 145-2C11), metyrosine was IP injected at 60 mg/kg into the contralateral side. A single additional dose of 30 mg/kg metyrosine was injected IP on the following day. Control groups were injected with PBS at the same times.

In Vitro Assays of Raji and Anti-CD19 CAR-T Cells

Raji, a human Burkitt's lymphoma cell line, was purchased from Sigma. Human CD19scFv-CD28-4-1BB-CD3ζ CAR-T cells (PM-CAR1003) were purchased from Promab Biotechnologies and maintained less than 7 days in AIM-V medium (GIBCO) supplemented with 300 IU/ml of hIL2 (Peprotech), 5% FBS and antibiotics (Car-T medium). In a 48 well plate, Raji cells were plated at $1 \times 10^5$/well and anti-CD19 CART cells were plated at $5 \times 10^5$/well in 275 μl of CAR-T medium. A solution of 3 mg/ml (−)-epinephrine was made in 0.1 N HCl and subsequently diluted in PBS for use at a final concentration of 15 ng/ml. Five minutes before the Raji and CART cells with or without epinephrine were mixed, metyrosine at 2 mM or human ANP at 5 μg/ml was added and then the cells were incubated for 24 hours at 37°

C. After incubation, the cells were pelleted by centrifugation at 700 g and 4° C. for 5 minutes and the supernatants were collected and mixed with 5 mM EDTA and 4 mM sodium metabisulfite for preservation of catecholamines, then stored at −80° C. until analysis.

Treatment of Tumor-Bearing Mice with Anti-CD19 CAR-T Cells

Six to eight-week old female NSG-SGM3 mice (NOD.Cg-Prkdcscid Il2rgtm1Wjl Tg(CMVIL3,CSF2, KITLG)1Eav/MloySzJ, Stock #013062) were purchased from the Jackson Laboratory. Raji cells were transfected with a luciferase construct via lentivirus to create Raji-luc cells as described elsewhere (Bai et al., 2015 *Neuro Oncol.,* 17:545). Human CD19scFv-CD28-4-1BB-CD3ζ CART cells (PM-CAR1003, CART19) from Promab Biotechnologies were maintained for less than 7 days in AIM-V medium (GIBCO) supplemented with 300 IU/ml of hIL2 (Peprotech), 5% FBS and antibiotics. One day before the injection of Raji cells, mice were irradiated at a dose of 2 Gy in a CIXD Xstahl device. One million Raji-luc cells were injected IV via tail vein on day zero. Six days later, tumor loads were assessed using a Xenogen instrument and $15 \times 10^6$ CART19 cells were injected IV. Metyrosine was injected IP at 60 mg/kg/day for three days before the CART19 injection. On the day of CART19 injection, a fourth dose of 60 mg/kg was given IP and the mice were subsequently injected four more times at daily intervals at 30 mg/kg.

Immunofluorescence and Immunohistochemistry Staining

Immunohistochemical (IHC) staining of paraffin-embedded mouse organs by the rat anti-Ly6G (8C5) antibody was performed as described elsewhere (see, e.g., Bai et al., *Neuro-oncology* 2015, 17:545-54), with the exception that rabbit anti-rat IgG biotin (312-066-045, Jackson ImmunoResearch) and Streptavidin peroxidase (Biogenex) were used as secondaries and staining reagents, respectively.

Measurement of Catecholamines and Cytokines in Mouse Plasma

Blood samples were collected into tubes containing 5 mM EDTA and 4 mM sodium metabisulfite after puncturing the facial vein or (terminally) by cardiac puncture. Subsequently, the samples were centrifuged and the plasmas were stored at −80° C. prior to analysis. Catecholamines (dopamine, norepinephrine and epinephrine) were measured using the 3-CAT Research ELISA kit from Labor Diagnostika Nord GmbH/Rocky Mountain Diagnostics. Cytokines were measured using Luminex assays based on Millipore Mouse and Human Cytokine/Chemokine panels.

Bilateral Adrenalectomy of Mice

Adrenalectomy was performed with 6-8 week-old female BALB/c mice. Mice were anesthetized similarly to the procedure in CLP experiments and a small incision was first made on one side of the back. After cutting through the muscle and exposing the peritoneal cavity, adrenal gland was identified as a small and pink organ located near the anterior pole of the kidney. The whole adrenal gland was carefully removed by a scissor with the help of forceps. The muscle was sutured and the skin was closed by a surgical stapler. Same procedure was repeated to the contralateral adrenal gland. Mice were given buprenorphine IP at 0.05 mg/kg immediately and the following day for pain reduction and 0.5 ml saline subcutaneously every day. Mice were allowed to recover for three days before the next procedure.

Results

Experiments described herein employed the anaerobic spore-forming bacterial strain *Clostridium novyi* (*C. novyi*)-NT to treat cancer (Staedtke et al., *Genes and Diseases* 2016, 3:144-52). These bacteria are strict anaerobes, and when spores are injected into animals or humans, bacteria germinate exclusively in hypoxic tumor tissues and can destroy them (Roberts et al., *Science Transl. Med.* 2014, 6:249ra111). However, when high doses of spores are injected into very large tumors, a massive infection occurs and the animals die within a few days from the consequences of cytokine-related toxicity.

To mitigate dose-limiting toxicity, mice were pre-treated, prior to injection of spores, with a variety of agents known to downregulate the inflammatory immune response, which has been highly effective in similar conditions (Grupp et al., *New Engl. J Med.* 2013, 368:1509-18; Riedemann et al., *J. Immunol.* 2003, 170:503-7; Qiu et al., *Critical Care Med.* 2013, 41:2419-29; Weber et al., *Science* 2015, 347:1260-5; Annane et al., *JAMA* 2002, 288:862-71). Blocking antibodies to the receptors for the pro-inflammatory cytokines IL-6R or IL-3, and antibodies to circulating TNF-$\alpha$, had no effect on survival (FIG. 1). Similarly, the anti-inflammatory agent dexamethasone did not protect animals from sepsis, even when used at very high doses.

The bacteria were engineered to remove bacterial components responsible for eliciting the overwhelming host immune response. All of these strains proved to germinate in tumors but none could eradicate tumors while sparing the mice.

Figure 1A:
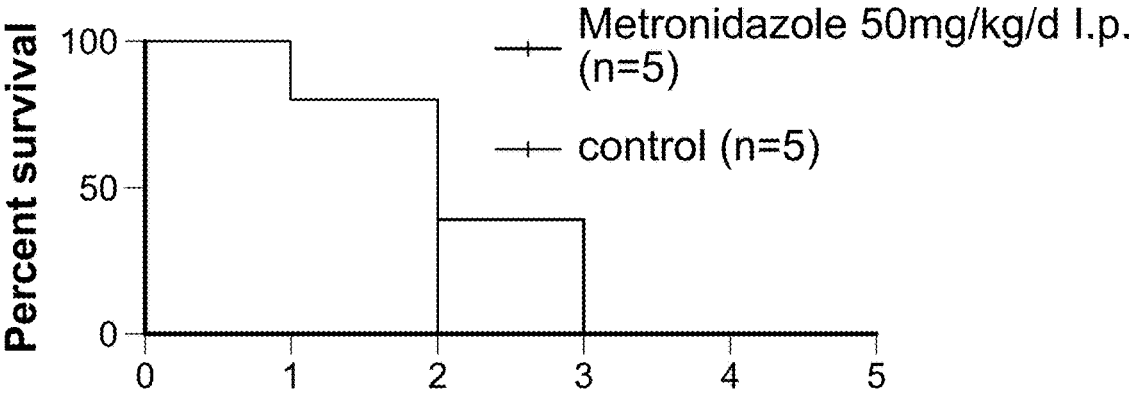
FIGS. 1A-1E show failure of therapeutic interventions in *C. novyi*-NT therapy-induced toxicity. Mice bearing large subcutaneous CT26 tumors (600-900 $mm^3$) were injected with 12 million parental *C. novyi*-NT spores intra-tumorally along with the indicated agents. Shown are the Kaplan-Meier survival curves of animals that received the antibiotic metronidazole (Figure A), dexamethasone (Figure B), or antibodies to the receptors for the pro-inflammatory cytokines including anti-IL-6R (Figure C), anti-mIL-3 (Figure D) and anti-TNF-α (Figure E) antibodies.
Figure 1B:
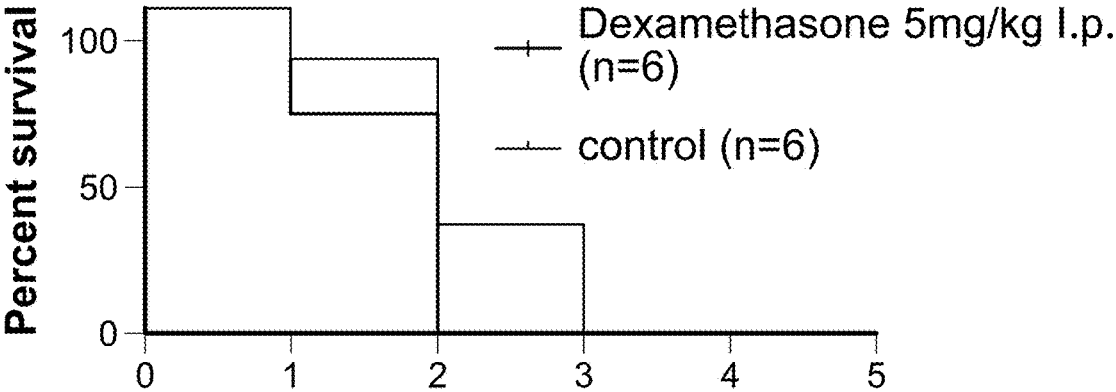
Figure 1C:
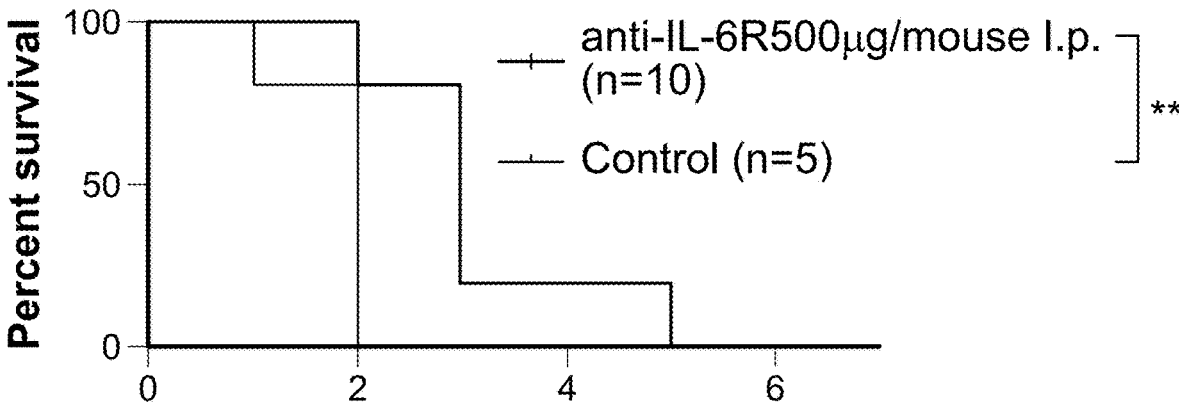
Figure 1D:
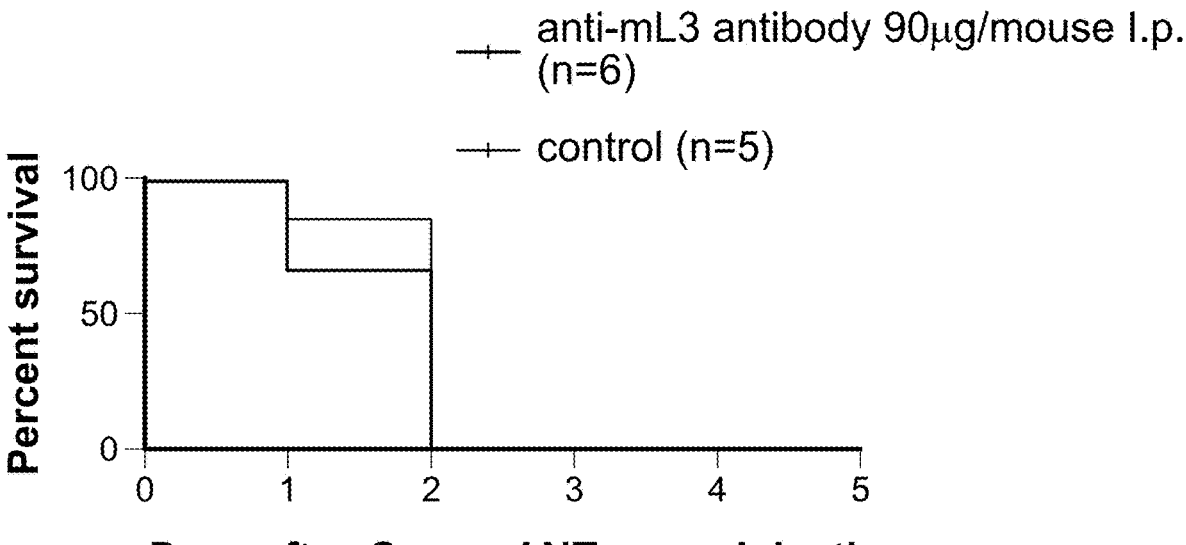
Figure 1E:
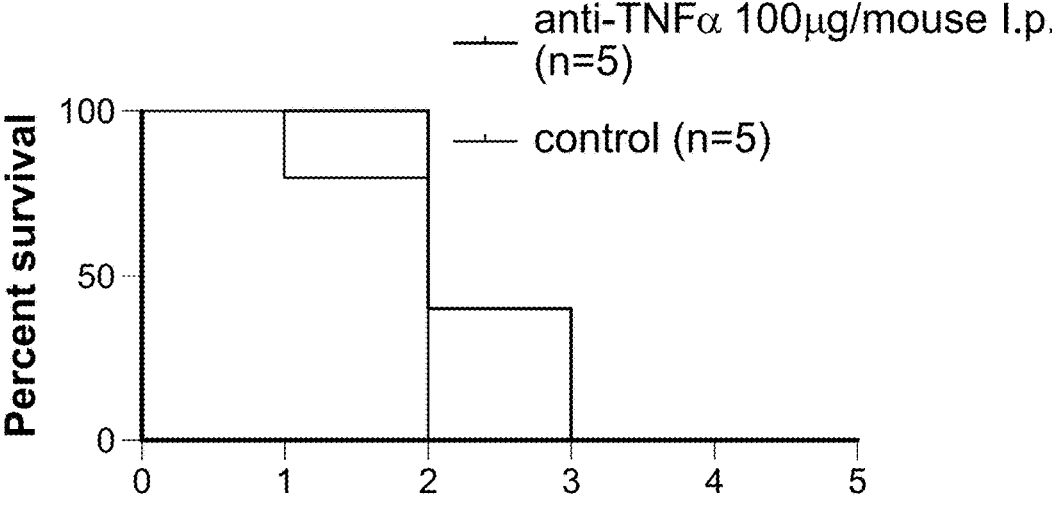
Figures 2A, 2B, 2C:
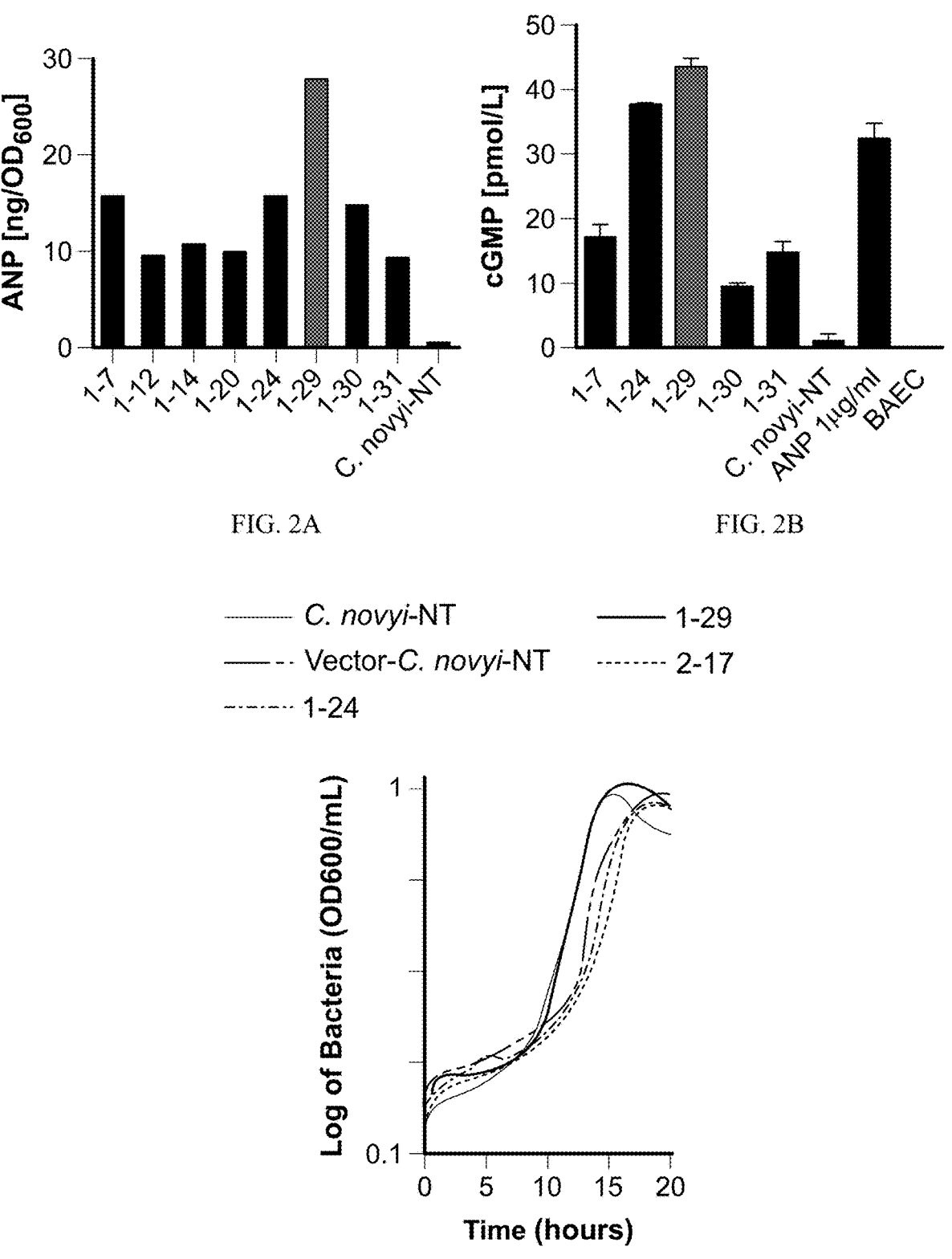
FIGS. 2A-2E show ANP-*C. novyi*-NT.

The bacteria were then engineered to secrete atrial natriuretic peptide (ANP). To see if ANP could protect mice from massive bacterial infections such as those caused by *C. novyi*-NT, *C. novyi*-NT were engineered to express and secrete ANP. A gene cassette encoding the ANP of 28-amino acids (AA) fused with a signal peptide at the N-terminus was optimized for *C. novyi* codon usage. This gene cassette was stably integrated into the *C. novyi*-NT genome using a method that combined the group II Intron targeting and bacterial conjugation (see Methods). Selected *C. novyi*-NT clones were characterized for ANP expression (FIG. 2A), biologic activity (FIG. 2B) and growth patterns in vitro (FIG. 2C). The clone with the highest expression of ANP, called ANP-*C. novyi*-NT, was selected for further studies.

Figure 2D:
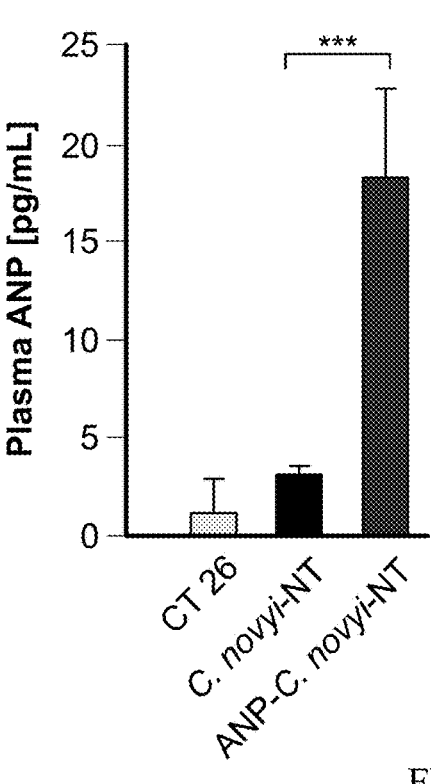
Figure 3A:
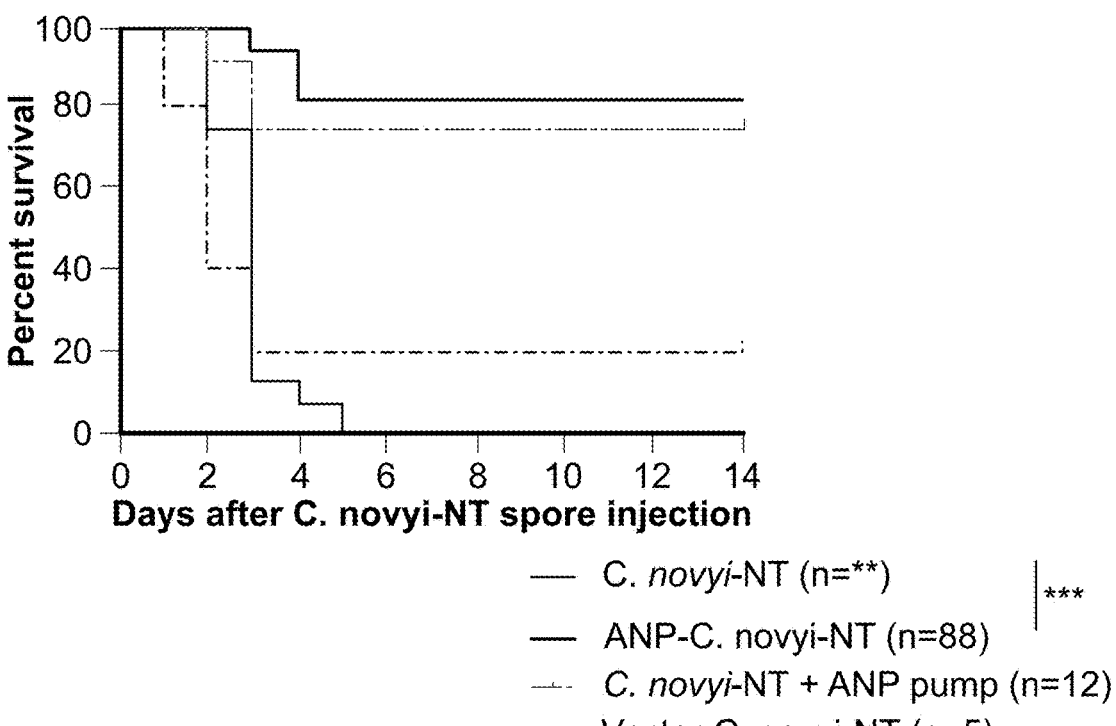
FIGS. 3A-3C show that ANP reduces mortality from the cytokine release syndrome.
Figure 3A:
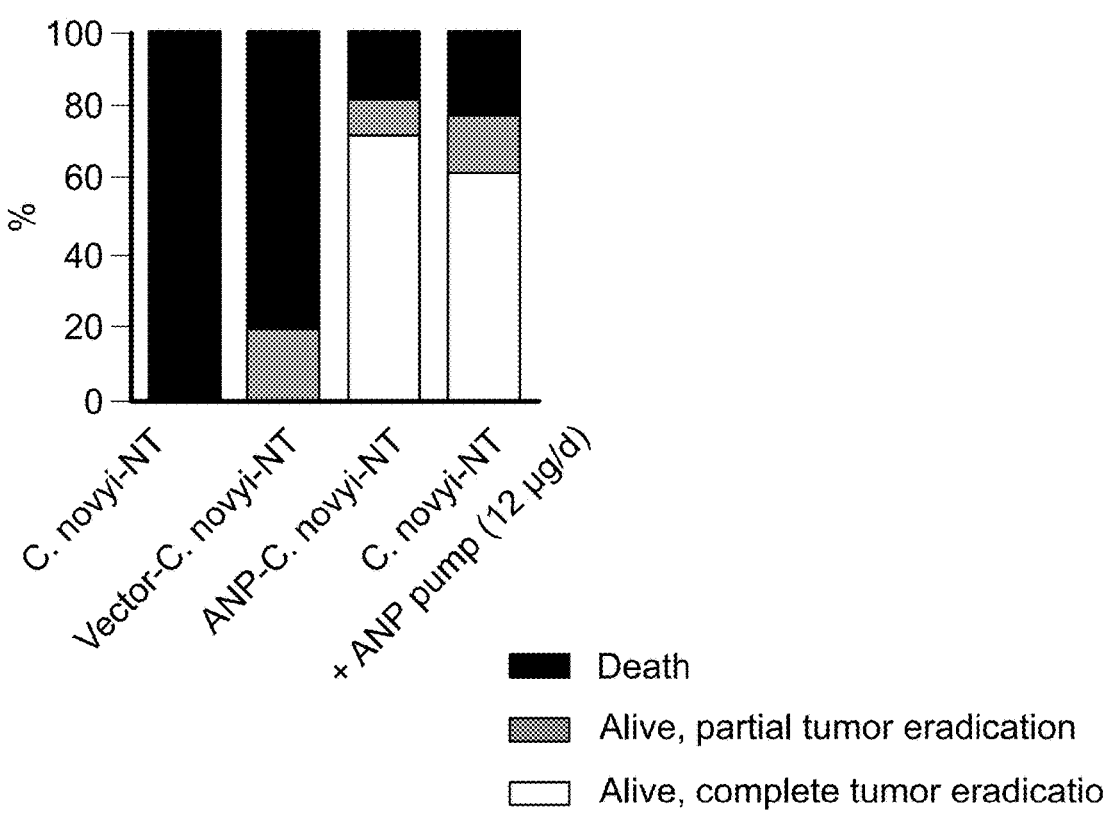
Figure 3B:
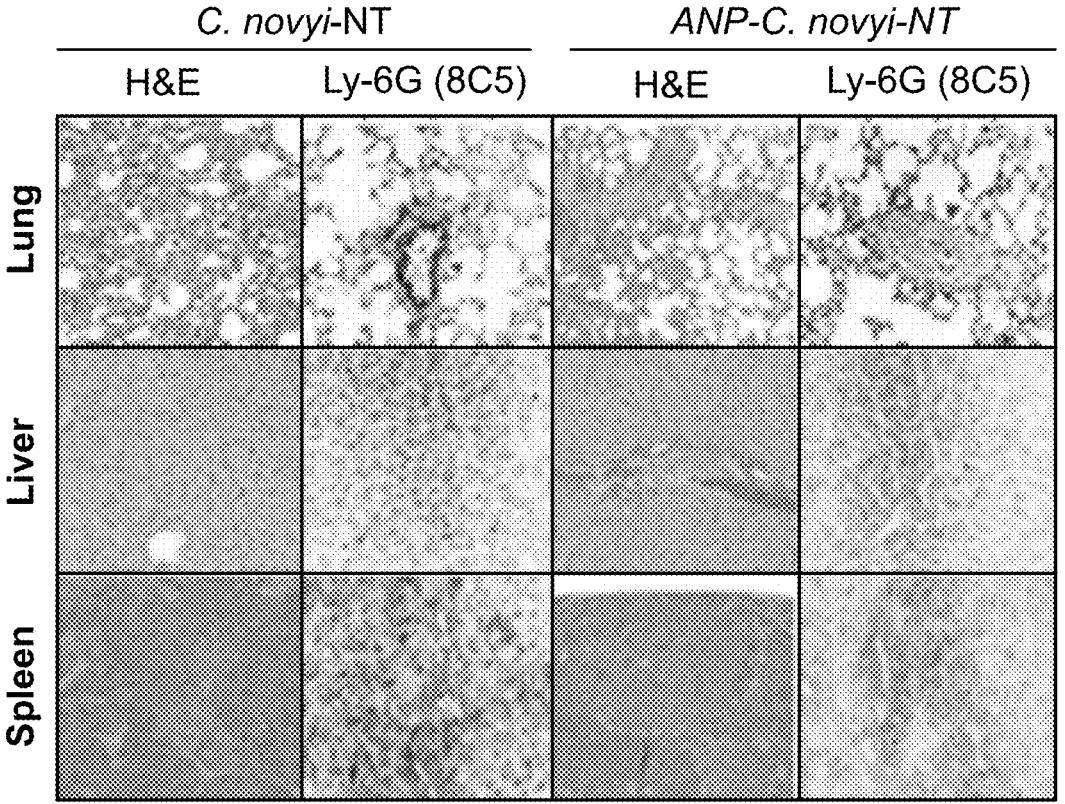

A single dose of ANP-*C. novyi*-NT spores injected into subcutaneously implanted CT26 colorectal tumors resulted in robust germination and cures, just as with the parental *C. novyi*-NT strain (FIG. 3A). Plasma ANP levels in mice injected with the ANP-*C. novyi*-NT strain were increased five times over that of mice injected with the parental *C. novyi*-NT strain (FIG. 2D). Strikingly, ~80% of the animals receiving the ANP-*C. novyi*-NT strain survived while none of the mice treated with the parental *C. novyi*-NT strain alone survived for longer than 5 days (FIG. 3A, upper panel). Moreover, 87% of the surviving mice treated with ANP-*C. novyi*-NT strain had complete tumor regressions and long-term cures (FIG. 3A lower panel).

Figure 2E:
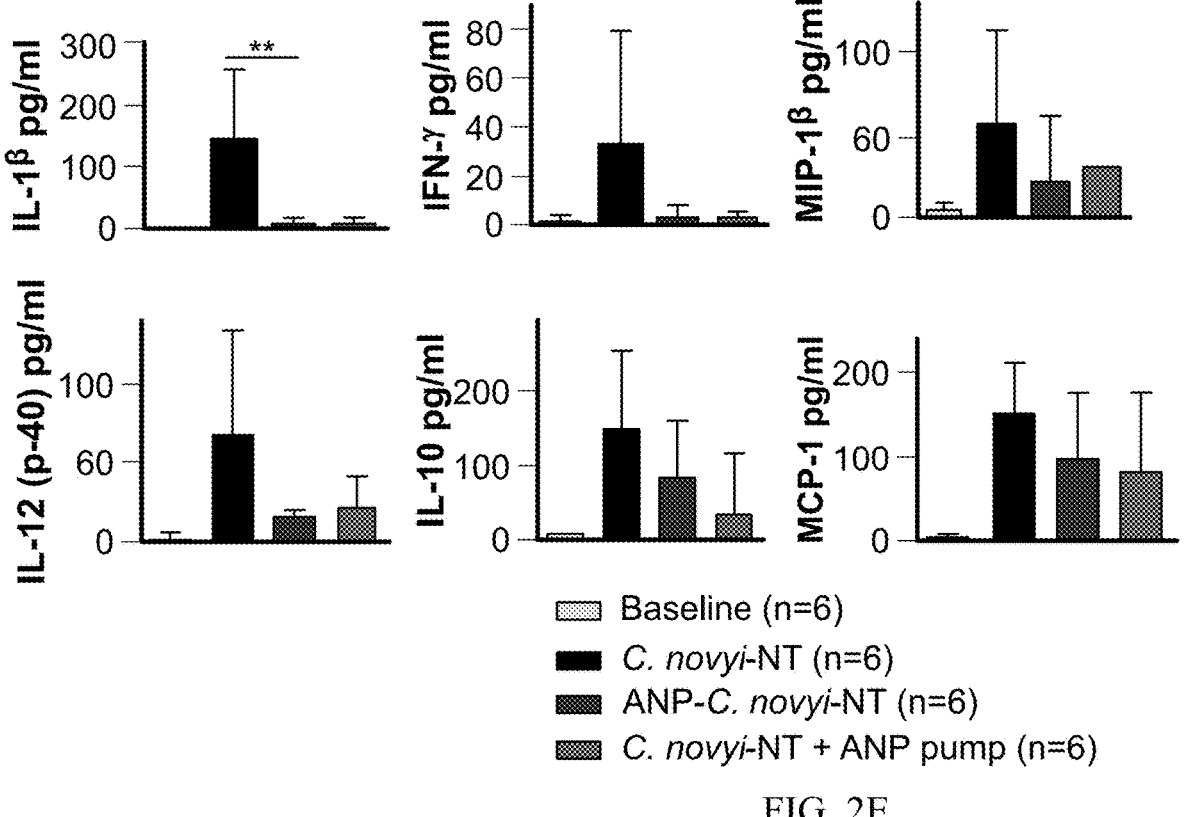
Figure 3C:
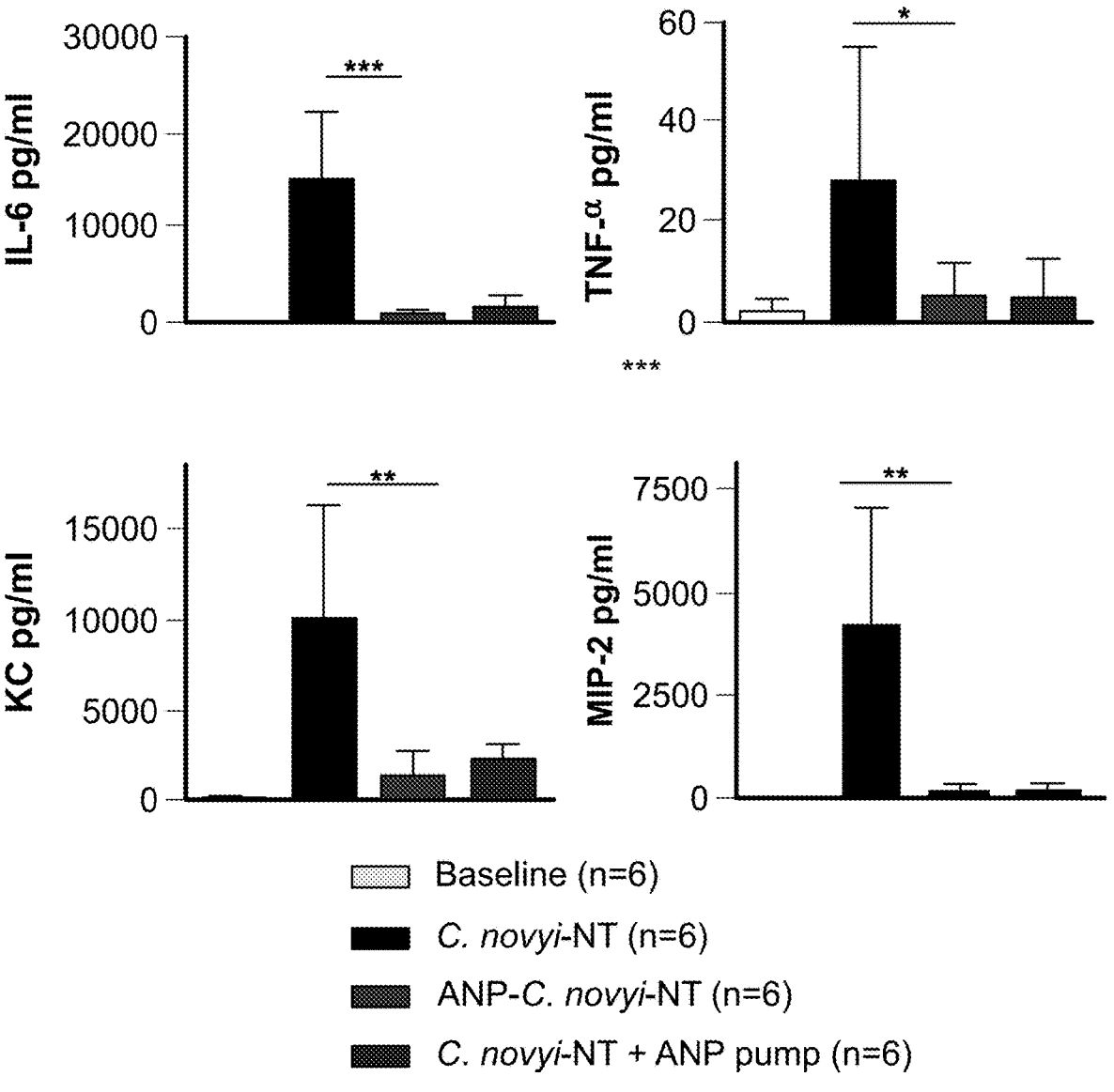

There was a noticeable reduction of tissue damage and leukocyte infiltration in the lungs, liver, and spleen of mice treated with ANP-*C. novyi*-NT (FIG. 1). Likewise, mice injected with the ANP-*C. novyi*-NT strain had significantly less inflammatory cytokines and chemokines in their circulation than those treated with the parental strain. In particular, there were drastic reductions in cytokines and chemokines released from activated T cells (IL-6, TNF-$\alpha$) and monocytes/macrophages (IL-1$\beta$, IL-6, MIP-2, TNF-$\alpha$), as well as chemoattractants (KC), cytokines involved in tissue damage (IL-6, KC), and to a lesser degree in IFN-$\gamma$, MIP-1$\beta$, IL-10 and MCP-1 (FIG. 3C and FIG. 2E). Systemically delivered ANP also resulted in major reductions of pro-inflammatory cytokines in the circulation, similar to what was observed with ANP-*C. novyi*-NT (FIG. 3C and FIG. 2E).

Figure 4:
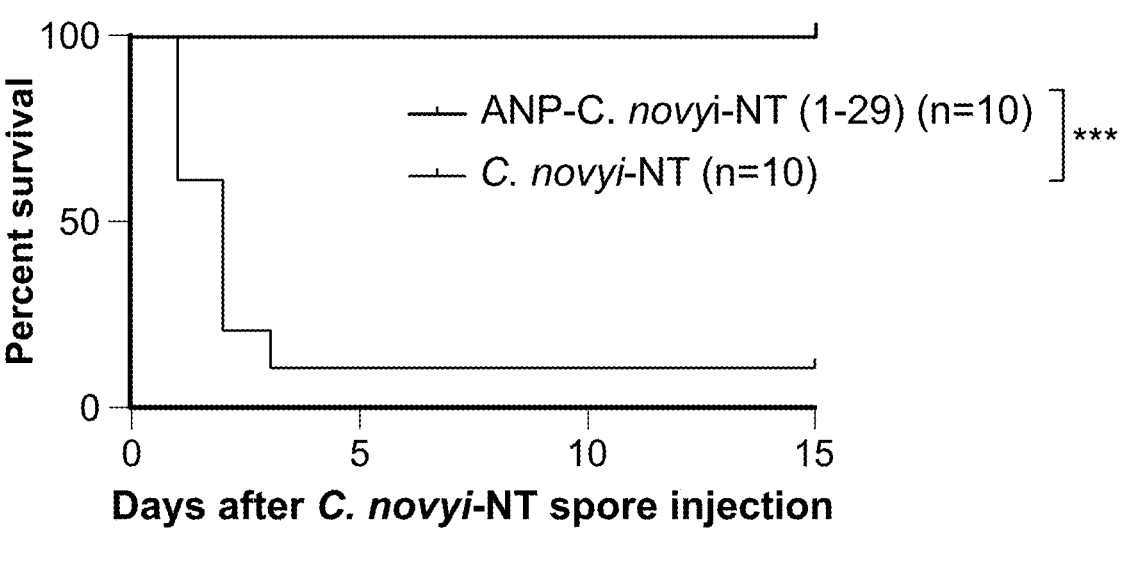
FIG. 4 shows that ANP-*C. novyi*-NT reduces therapy-induced mortality. GL-261 glioblastoma cells were subcutaneously implanted into C57BL/6 mice. Once the tumor reached 600-900 $mm^3$, 12 million *C. novyi*-NT or ANP-*C. novyi*-NT spores were directly injected into the tumor and the mice were monitored for survival. Kaplan-Meier survival curves of *C. novyi*-NT and ANP-*C. novyi*-NT treated animals are shown.

This study was repeated in a different tumor type in another strain of mice. Using subcutaneous implants of the glioblastoma cell line GL-261 in C56Bl/6 mice, 100% of mice treated with ANP-*C. novyi*-NT survived and had substantial tumor reductions, while nearly all of the mice treated with the parental strain of *C. novyi*-NT died within 72 hours of infection (FIG. 4).

To determine whether protection from the CRS was due to the expression of ANP rather than to some other unknown change in the engineered strain, mice were pre-treated with ANP released from an osmotic pump that was implanted 12 hours prior to injection with parental *C. novyi*-NT spores. The ANP delivered by this pump proved efficacious, with ~75% of the mice surviving (FIG. 3A, upper panel). Of those that survived, all animals showed significant therapeutic responses: in 80%, the tumor was completely eradicated and in the other 20%, a robust but not curative response was observed (FIG. 3A, lower panel).

Figure 5A:
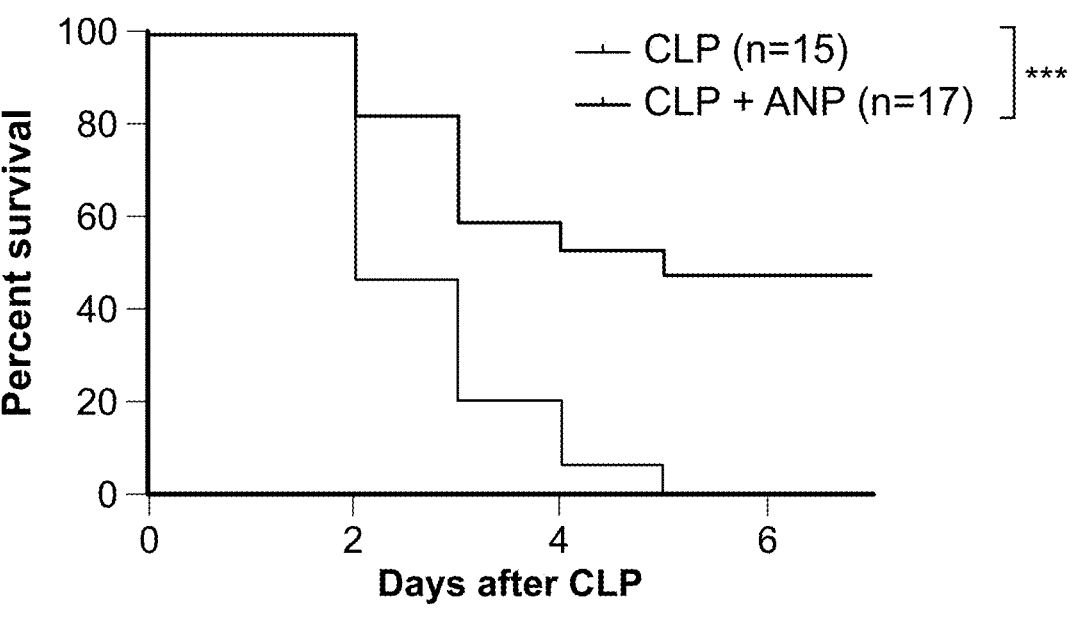
FIGS. 5A-5C show that ANP prevents death from septic shock induced by CLP.
Figure 5B:
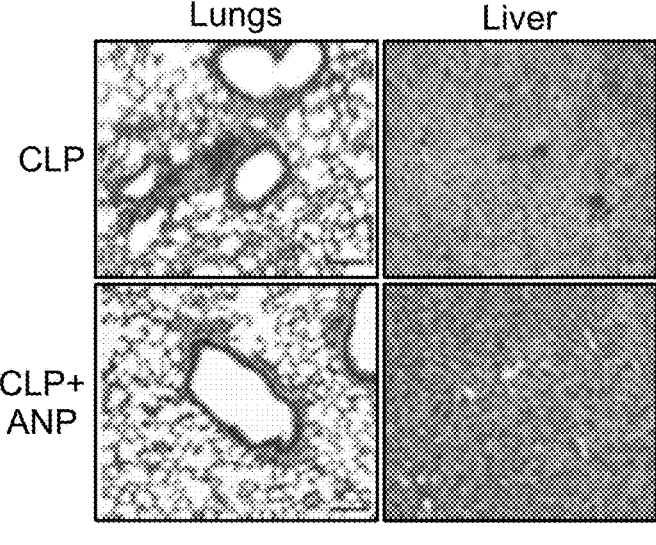
Figure 5C:
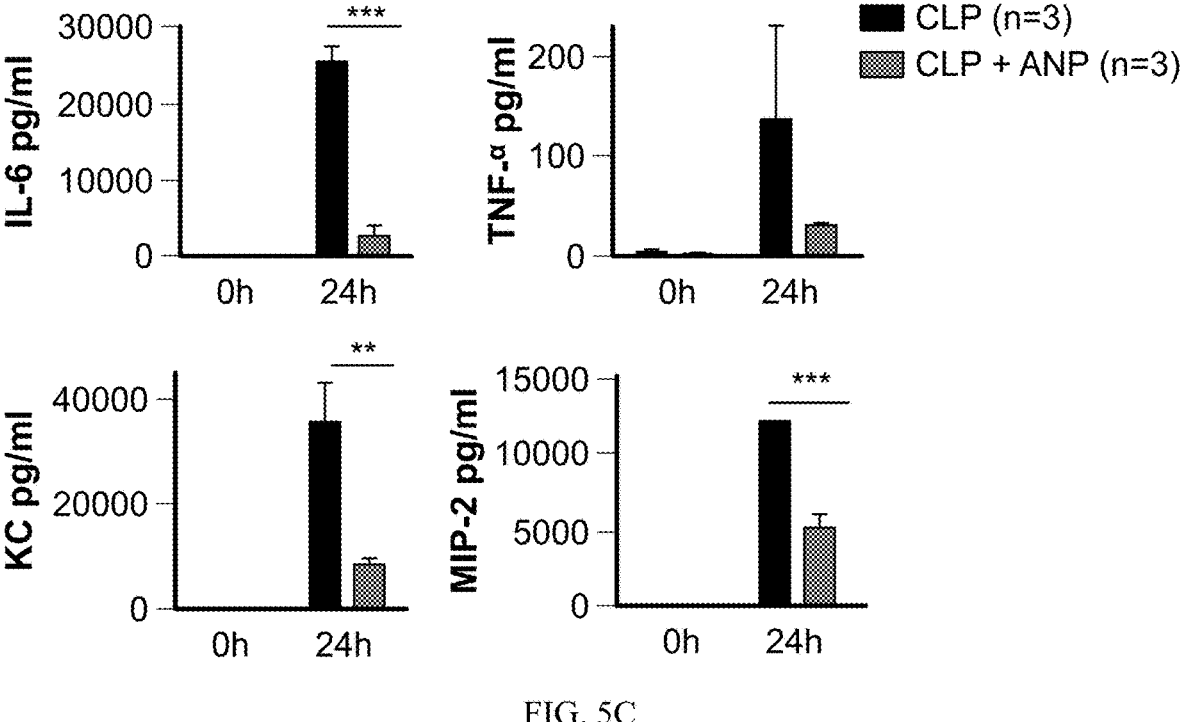
Figure 6A:
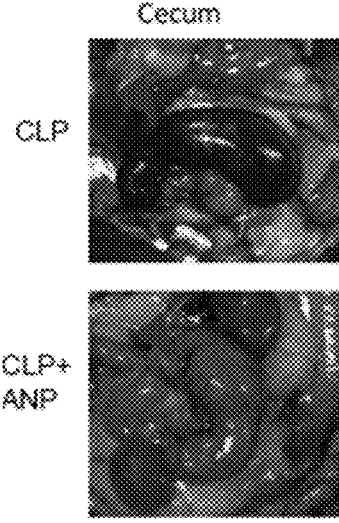
FIGS. 6A-6B show that ANP prevents death from septic shock induced by CLP FIG. 6A contains macroscopic images of the intestines taken 24 hours after CLP demonstrating the cecal inflammation and necrosis (arrows).
Figure 6B:
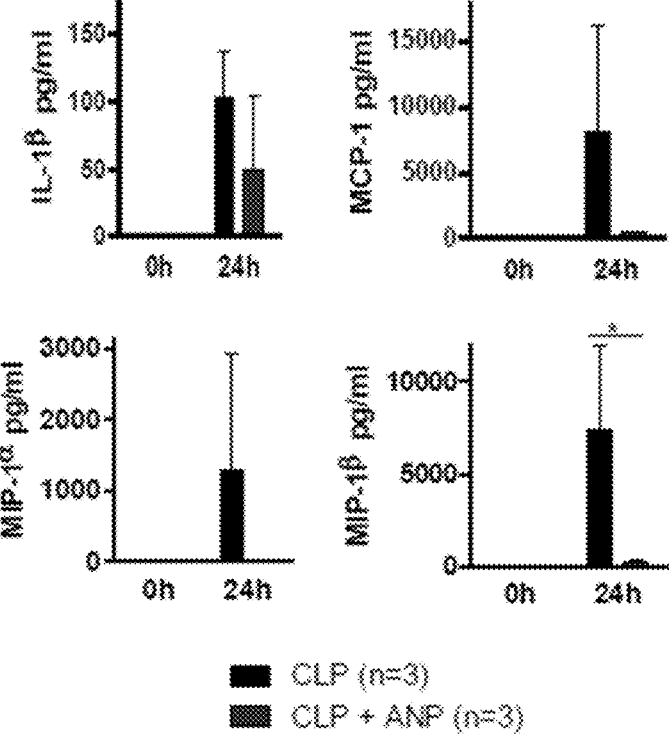

*C. novyi*-NT is a gram positive bacterium and it is known that sepsis resulting from gram-positive bacteria is different than that resulting from gram-negative bacteria with regards to host-immune interaction and cytokine release (Surbatovic et al., 2015 *Sci. Rep.*, 5:11355). Genetically-engineered gram-negative bacteria are also being used in experimental therapies for cancer (Zheng et al., 2017 *Sci. Transl. Med.*, 9; Forbes, 2010 *Nat. Rev. Cancer*, 10:785-94; and Hoffman, 2016 *Methods Molecular Biology*, 1409:177). To determine whether ANP could protect mice from infection with bacteria in general, its effects were evaluated when administered prior to cecal ligation and puncture (CLP), a particularly challenging sepsis model. This puncture releases large numbers of enteric bacteria, including many species of gram-negative bacteria, into the peritoneum, causing polymicrobial peritoneal sepsis. ANP was administered as described above, using an osmotic pump that was implanted subcutaneously 12 hours before CLP. ANP significantly reduced the mortality from the polymicrobial peritoneal sepsis—almost half of the animals survived the acute phase, while all animals died in the control arm (FIG. 5A). Treatment with ANP after, rather than before, CLP did not rescue the mice. Thus, ANP represents a method to prevent toxicity from cytokine release. In the ANP pre-treated mice, pathologic examination revealed less peritoneal inflammation, pulmonary septal thickening, and hepatic inflammation compared to control animals (FIG. 5B and FIG. 6A). The levels of pro-inflammatory cytokines present in the circulation after ANP pretreatment was greatly reduced compared to control animals following the CLP procedure. This reduction was particularly pronounced for cytokines IL-6, KC, MIP-2 and MIP-1$\beta$, and MCP-1 (FIG. 5C and FIG. 6B).

Figure 7:
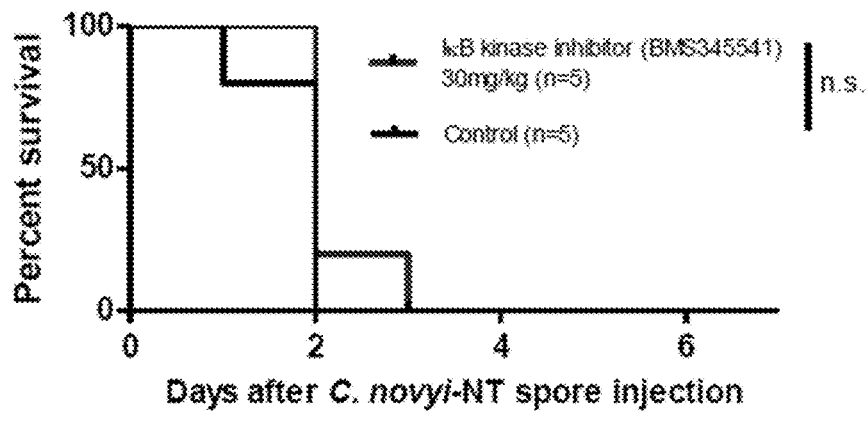
FIG. 7 shows that IκB kinase inhibition did not improve survival in *C. novyi*-NT therapy-induced sepsis. Kaplan-Meier survival curves of mice treated with IκB kinase inhibitor BMS345541 while undergoing *C. novyi*-NT therapy.

To investigate the mechanism underlying the protective effects of ANP, BMS-345541, a highly selective inhibitor of I$\kappa$B kinase that has been shown to reduce cytokine levels in other model systems (Burke et al., 2003 *J. Biol. Chem.*, 278:1450), was administered to mice bearing large CT26 tumors prior to intratumoral injection with the parental strain of *C. novyi*-NT. However, unlike the case with ANP, there was no improvement in survival after pre-treatment with BMS-345541 (FIG. 7). This result suggested that ANP inhibits the hyperinflammation resulting from *C. novyi*-NT infection through means in addition to, or other than, those involving the NF-$\kappa$B pathway.

Figures 8A, 8B:
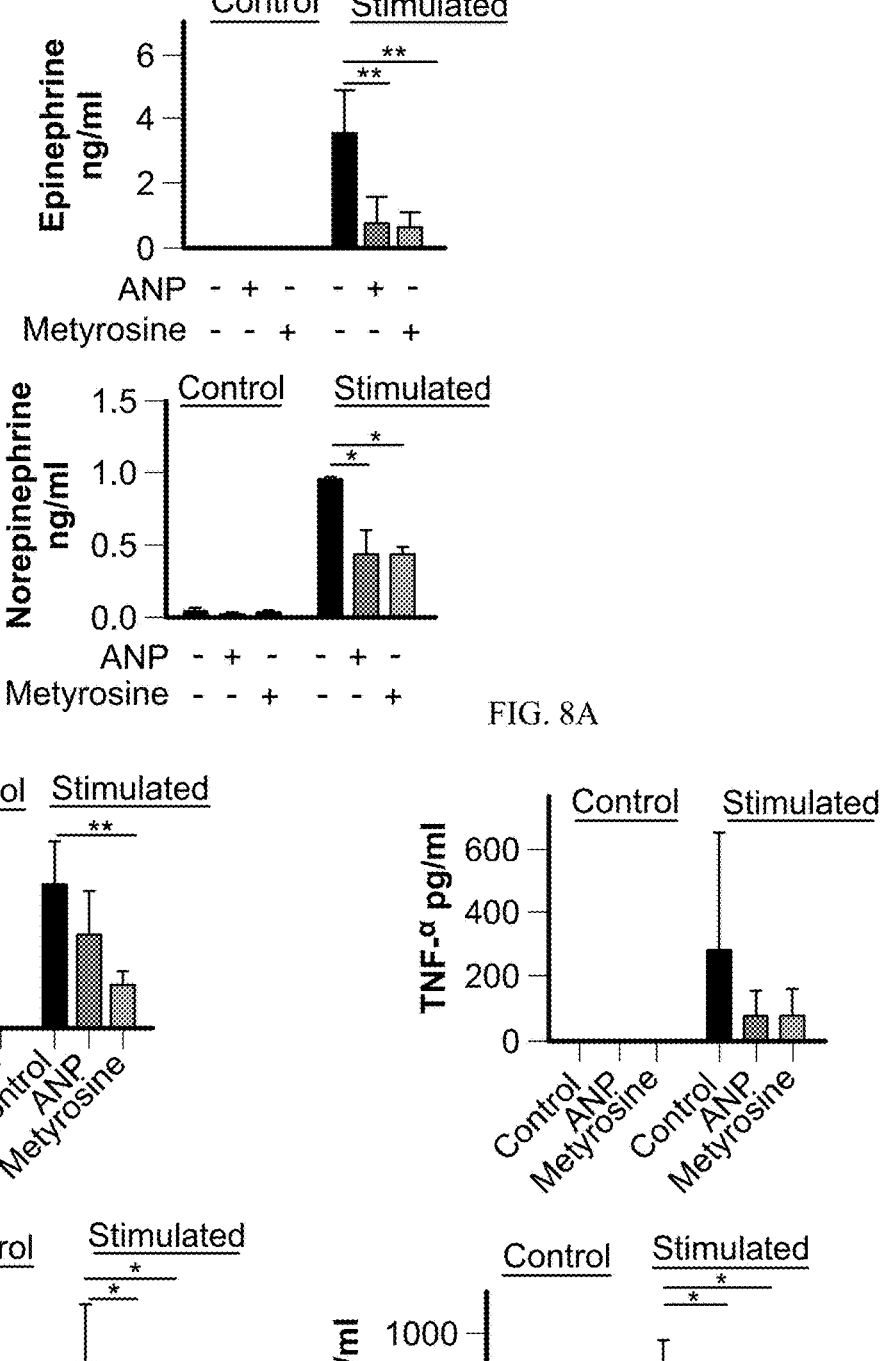
FIGS. 8A-8D. Effects of the inhibition of catecholamine synthesis.
Figures 8C, 8D:
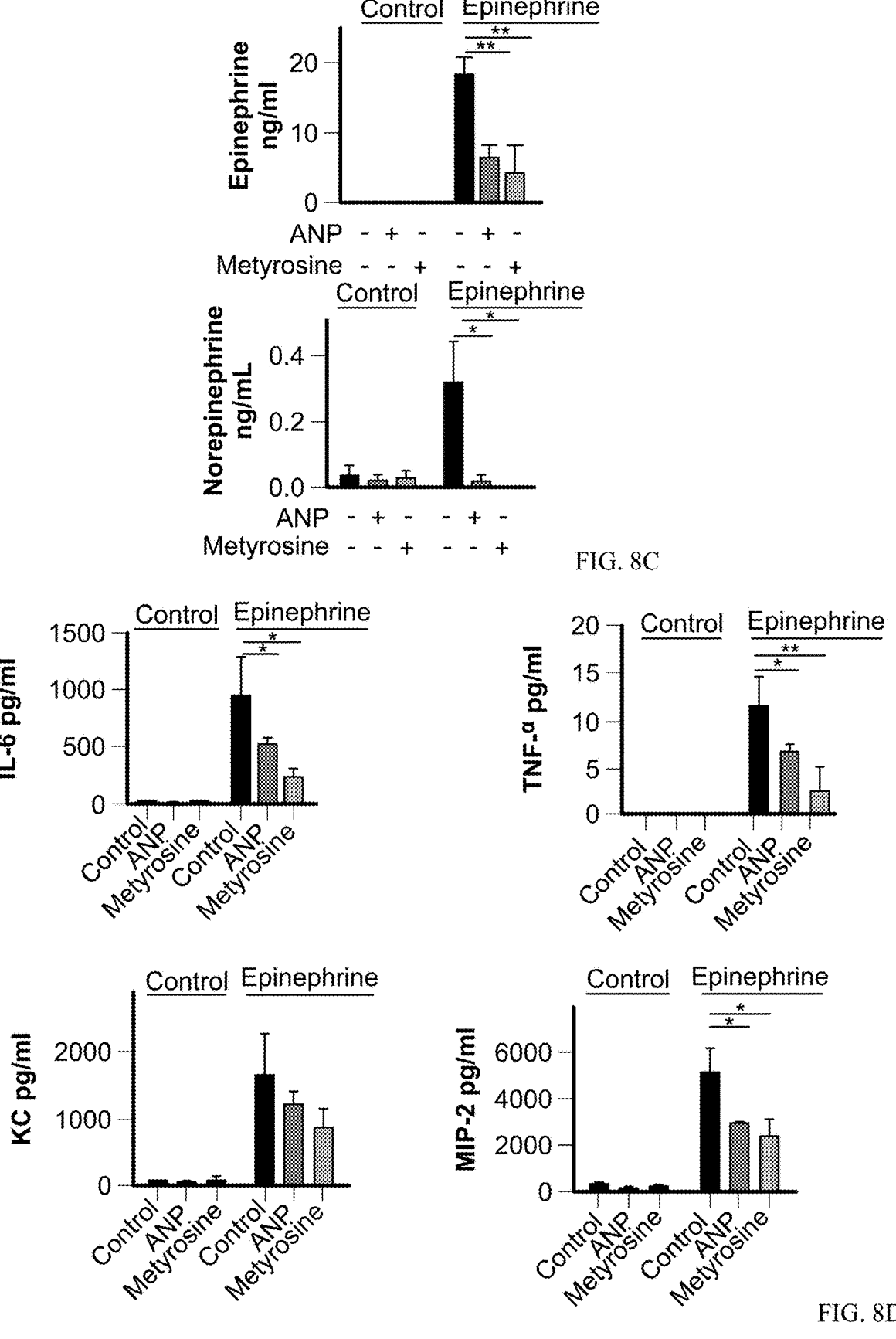
Figure 9A:
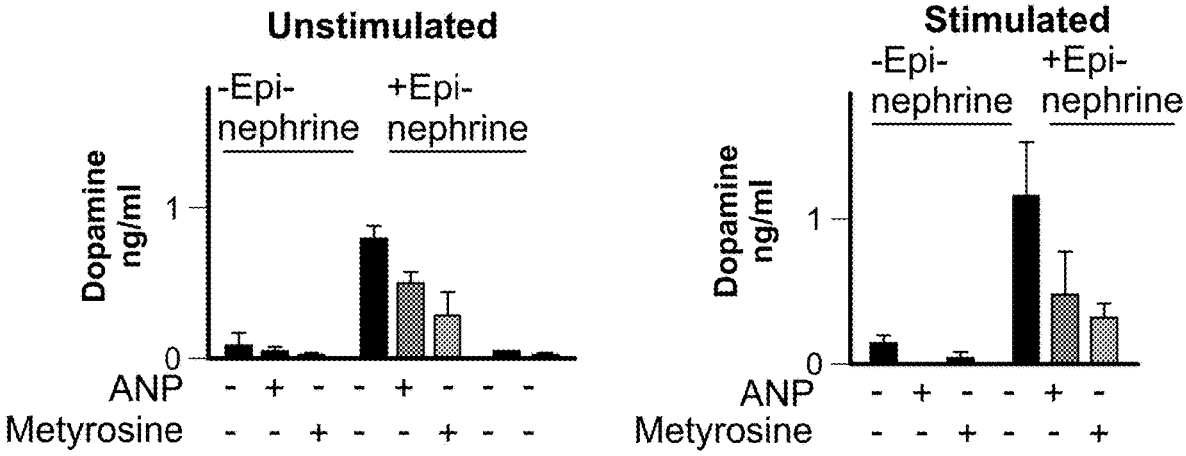
FIGS. 9A-9D shows dopamine levels in the experimental models.

To investigate a potential relationship between atecholamines and the protective effects of ANP, it was first determined whether ANP could inhibit the production of catecholamines in isolated macrophages. ANP was found to reduce the production of all three major catecholamines (epinephrine, norepinephrine and dopamine) in mouse peritoneal macrophages exposed to inflammatory stimuli (FIG. 8A and FIG. 9A). It was also found that epinephrine itself can stimulate catecholamine production in macrophages in an autocrine manner and ANP pre-treatment inhibited this production (FIG. 8C and FIG. 9A).

If the protective effects of ANP were due to its ability to interfere with catecholamine production, then inhibition of catecholamine synthesis should mimic the effects of ANP. Pre-treatment with α-methyltyrosine (metyrosine), a specific inhibitor of catecholamine synthesis, greatly reduced the catecholamines produced by mouse macrophages exposed to LPS, a potent inflammatory stimulus (FIG. 8A). Cytokine release by macrophages was similarly inhibited by metyrosine in vitro (FIG. 8B). Next, mouse peritoneal macrophages were exposed to physiologic levels of epinephrine or epinephrine plus LPS to demonstrate the inflammatory response of the autocrine induction of catecholamines and cytokines, and suppression was similarly inhibited (FIGS. 8C and 8D; FIG. 10; FIG. 9A; and FIG. 11A).

Figure 9B:
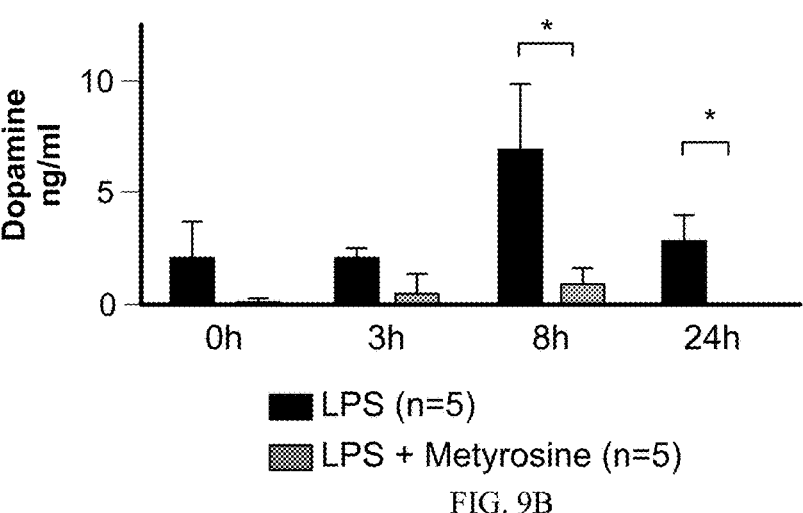
Figure 10A:
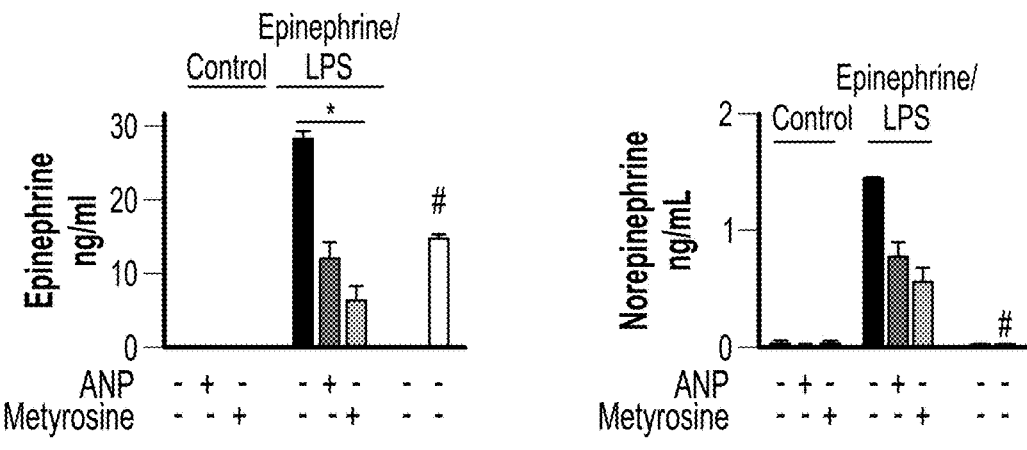
FIGS. 10A-10E shows that exogenous epinephrine exaggerates the inflammatory response, which can be inhibited by ANP and catecholamine synthesis inhibitor metyrosine.
Figure 10B:
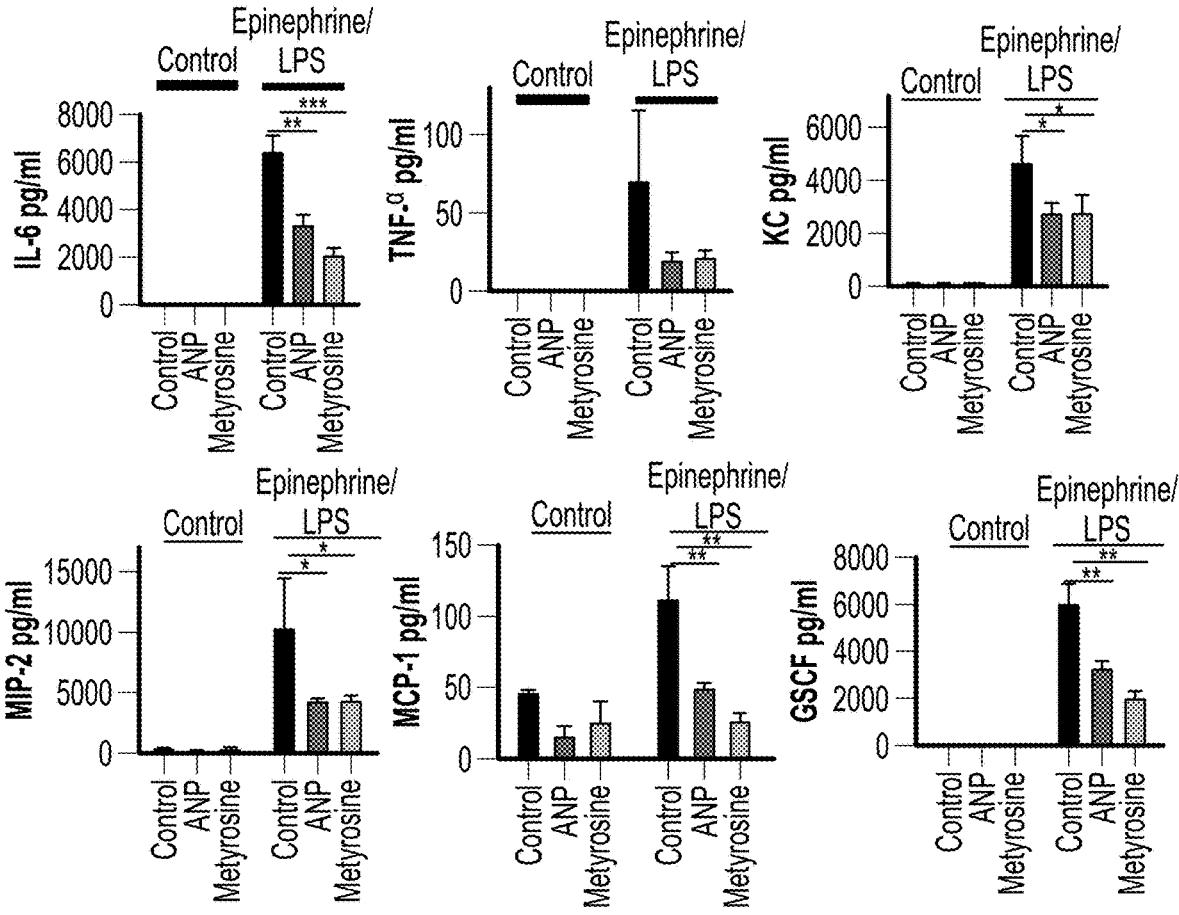
Figure 10C:
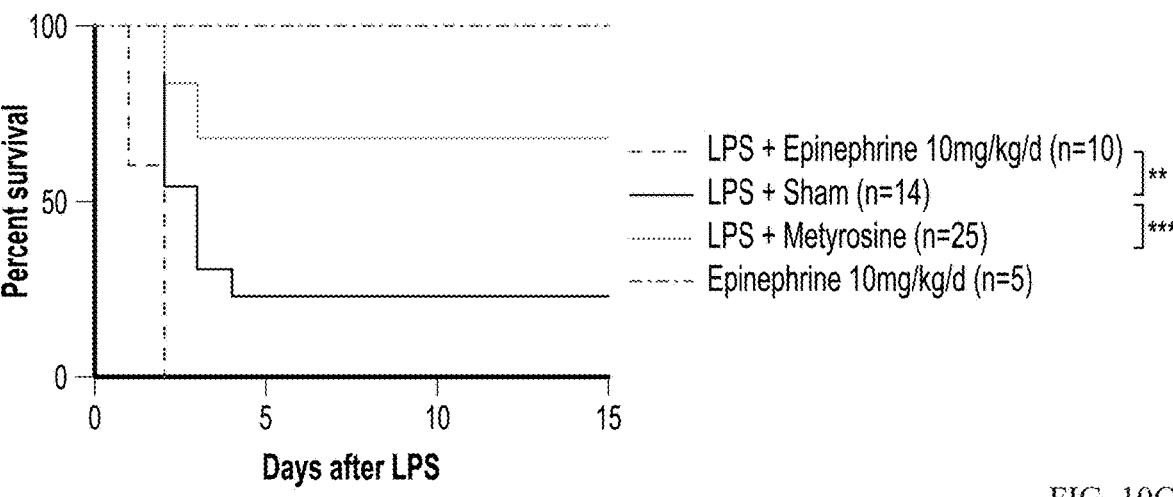
Figure 10D:
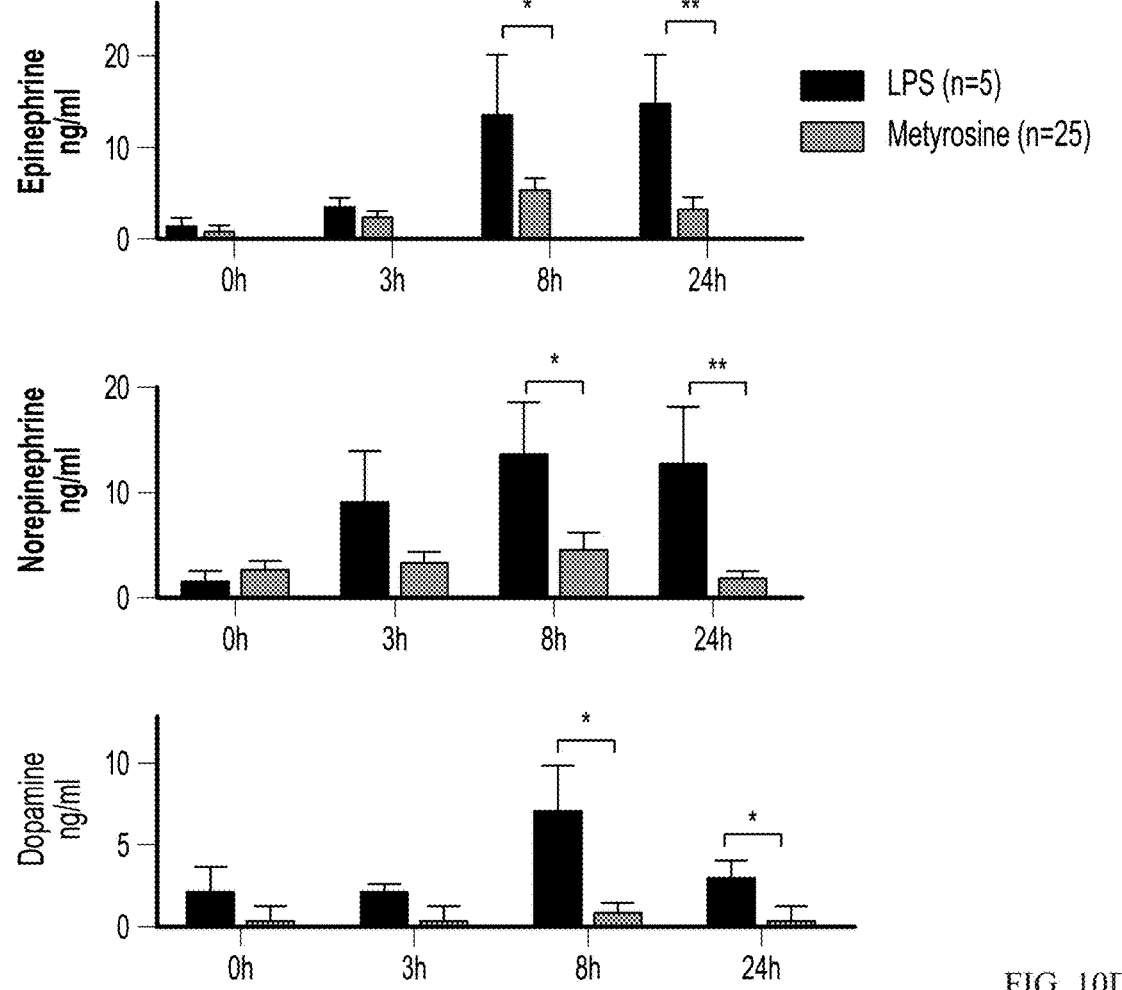
Figure 10E:
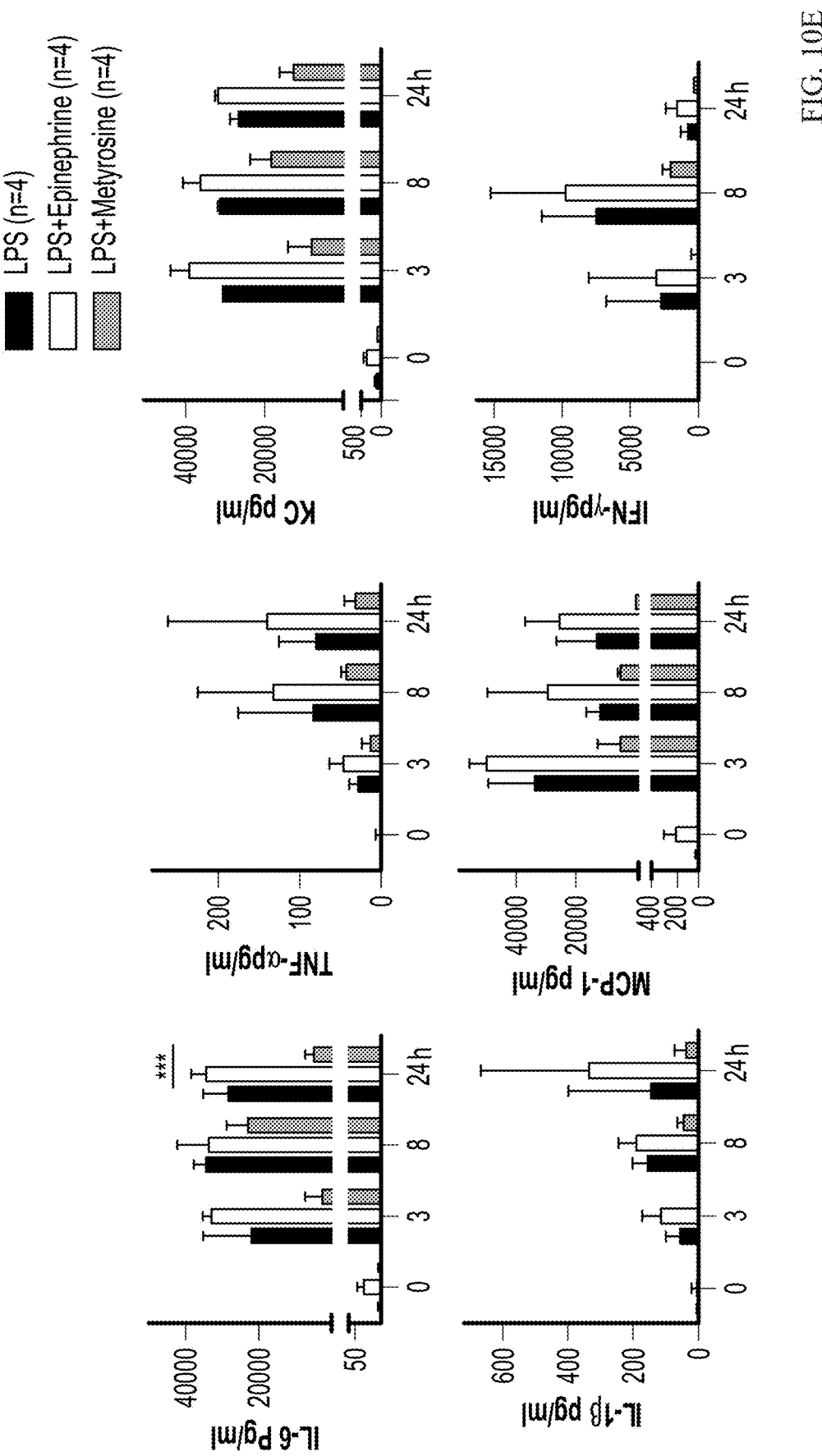

Metyrosine was found to have similar effects in vivo. When mice were pre-treated with metyrosine and then administered the same inflammatory stimulant, ~70% of the mice survived, whereas only 23% survived without metyrosine pre-treatment (FIG. 10C). Both the levels of catecholamines and the levels of inflammatory cytokines were substantially reduced in the mice pre-treated with metyrosine (FIGS. 10D and 10E; FIG. 9B).

Figure 9C:
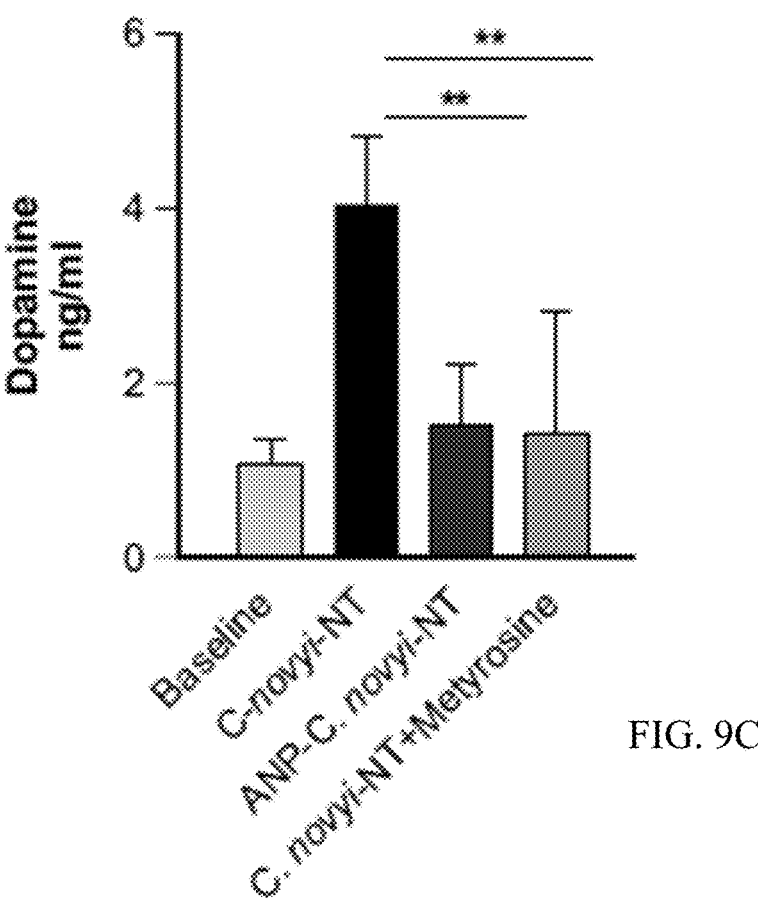
Figure 9D:
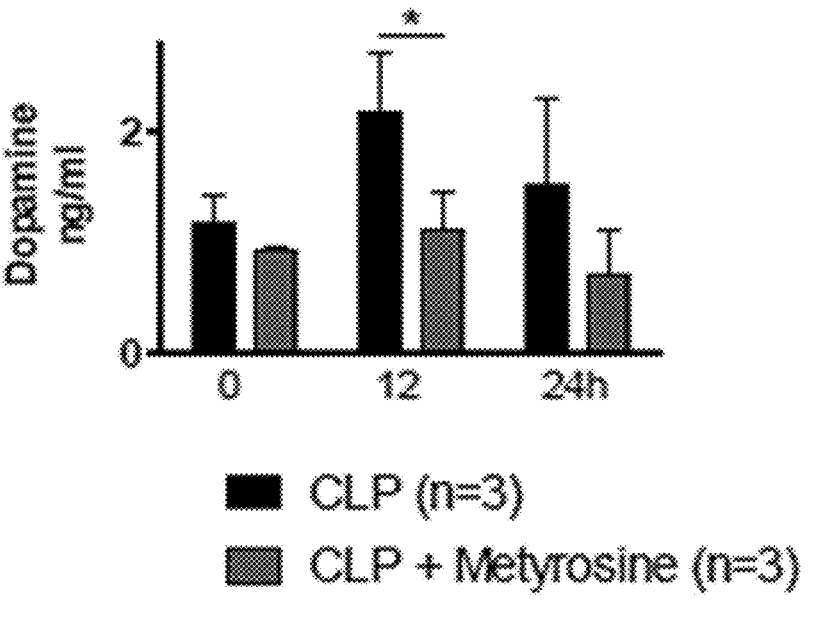
Figures 12A, 12B:
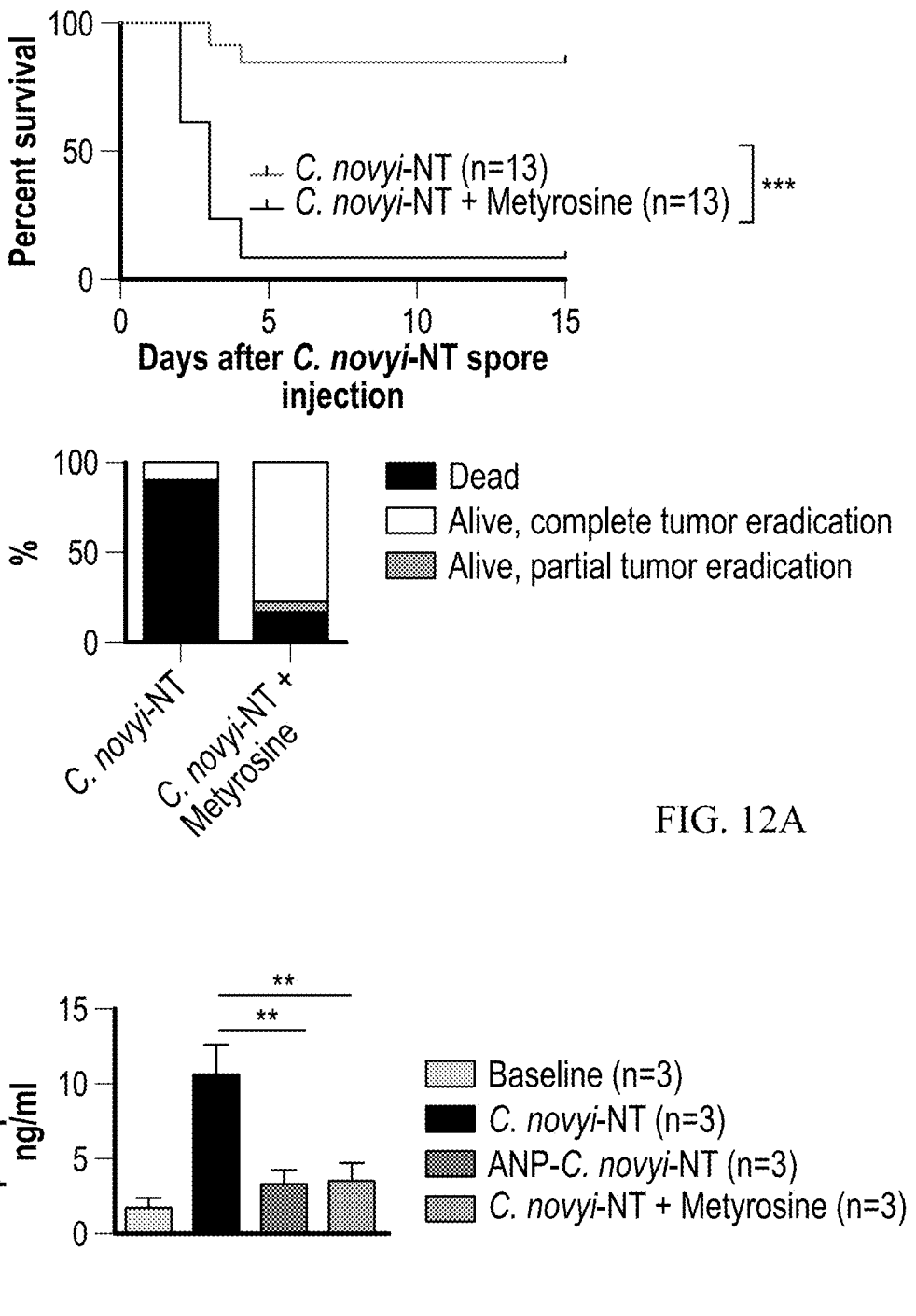
FIGS. 12A-12F show suppression of catecholamines with metyrosine reduces toxicity from bacteria-generated sepsis.
Figures 12C, 12D:
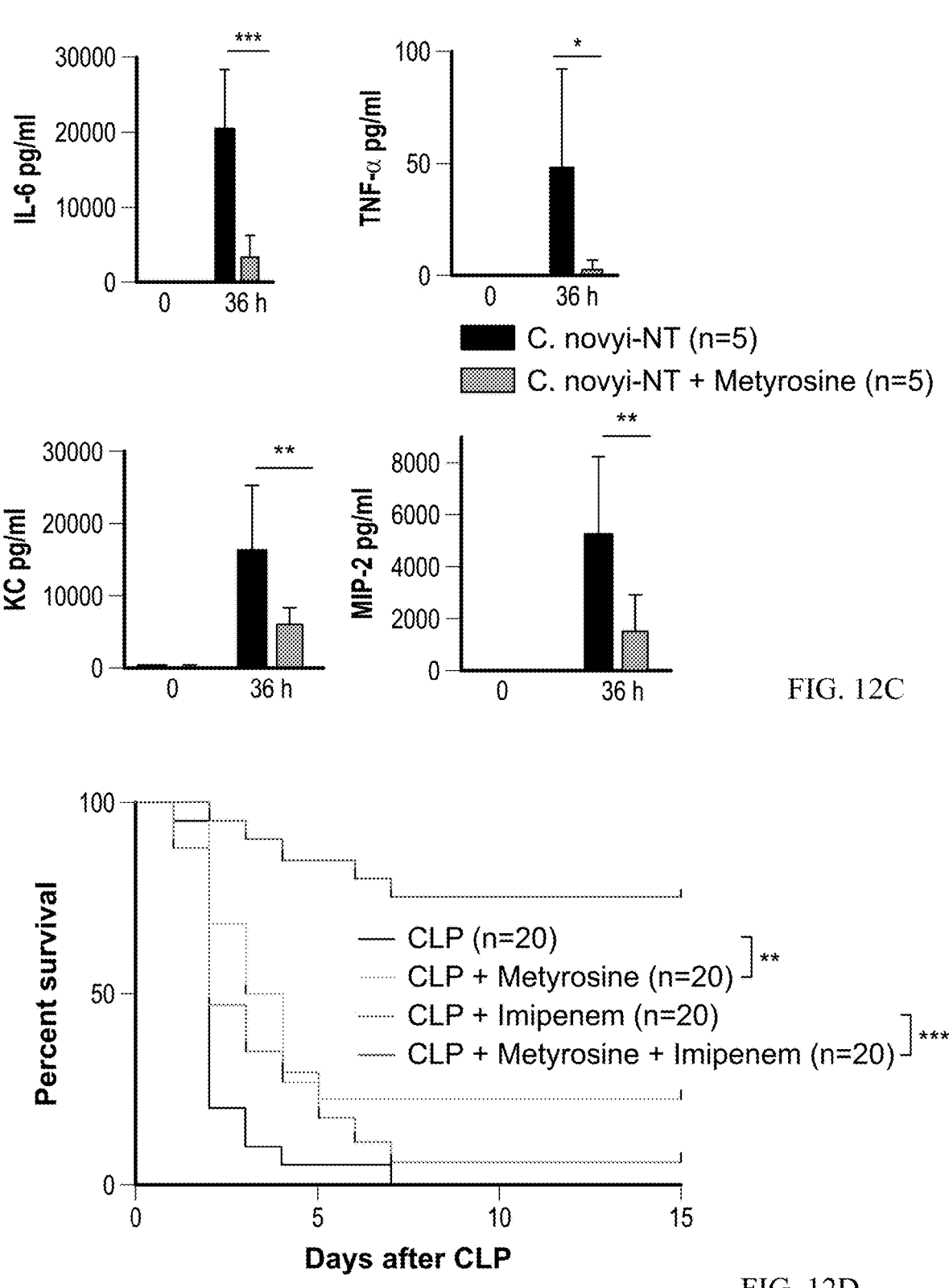
Figures 12E, 12F:
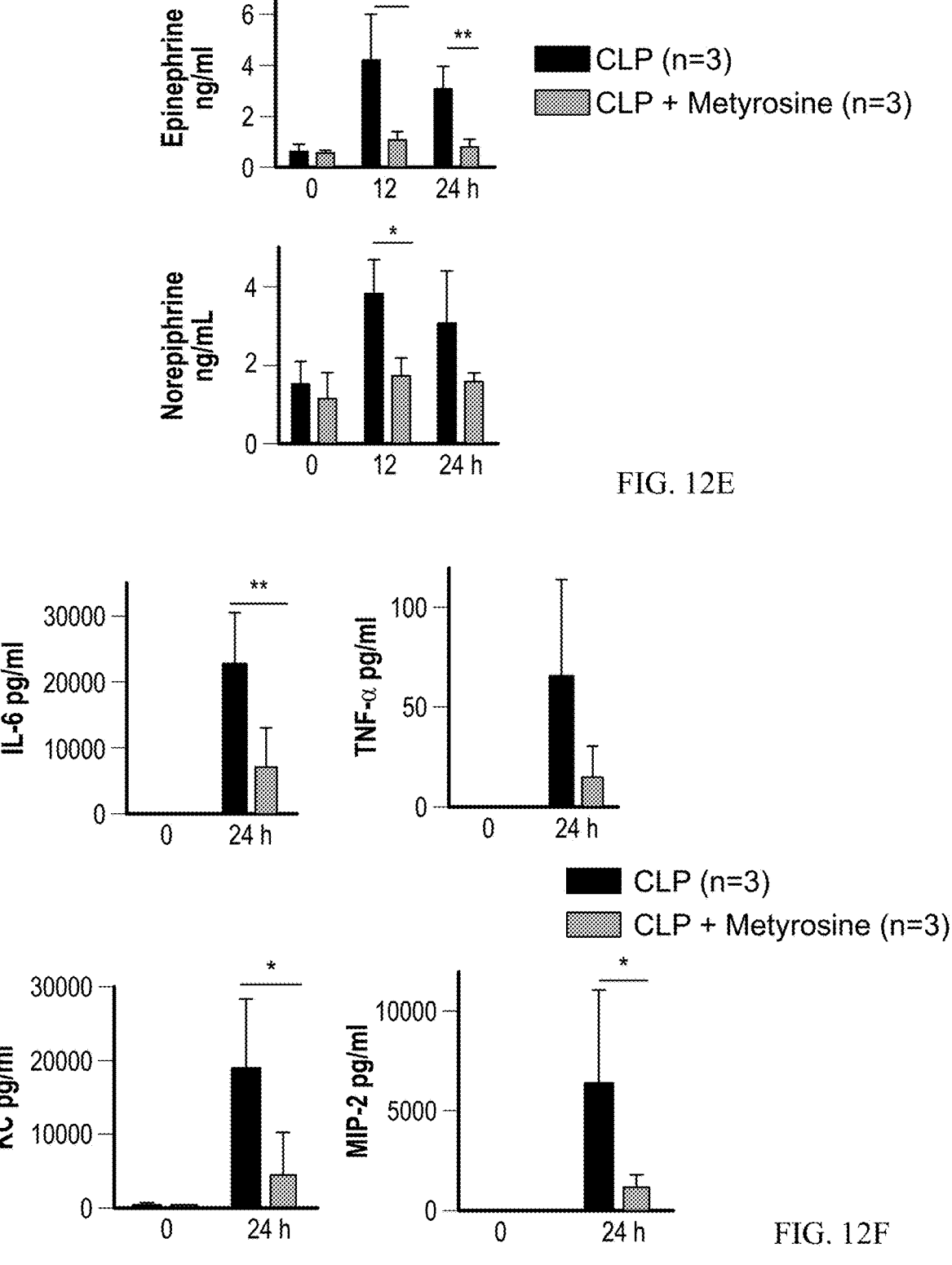

To document the generality of the effects of metyrosine, mice were treated with metyrosine prior to the induction of CRS by infection with parental C. novyi-NT. 85% of the mice pre-treated with metyrosine survived while only 7% of the mice in the control arm survived (FIG. 12A). As expected, catecholamines and cytokines were substantially reduced in animals pre-treated with metyrosine (FIGS. 12B and 12C; FIG. 9C). Pre-treatment with metyrosine could also protect a subset (20%) of mice from polymicrobial peritonitis (FIG. 12D), though less effectively than ANP (FIG. 5A). However, when mice were pre-treated with metyrosine as well as with the β-lactam antibiotic imipenem at 20 hours after CLP, >⅔ of the mice survived CLP, while 88% of mice treated with the antibiotic alone died. This experiment highlights the fact that death from overwhelming bacterial infections is due to two factors: the bacteria themselves and the host reaction to the infection (i.e. CRS). To formally demonstrate that the detrimental host response was diminished by metyrosine pre-treatment, the levels of circulating cytokines were measured as described above. Multiple cytokines characteristic of sepsis or inflammation were substantially reduced by metyrosine after infection with C. novyi-NT or induction of polymicrobial peritonitis by CLP (FIGS. 12C and 12F). The effects of metyrosine on circulating catecholamines were also documented (FIGS. 12B and 12E; FIGS. 9C and 9D).

Figure 13C:
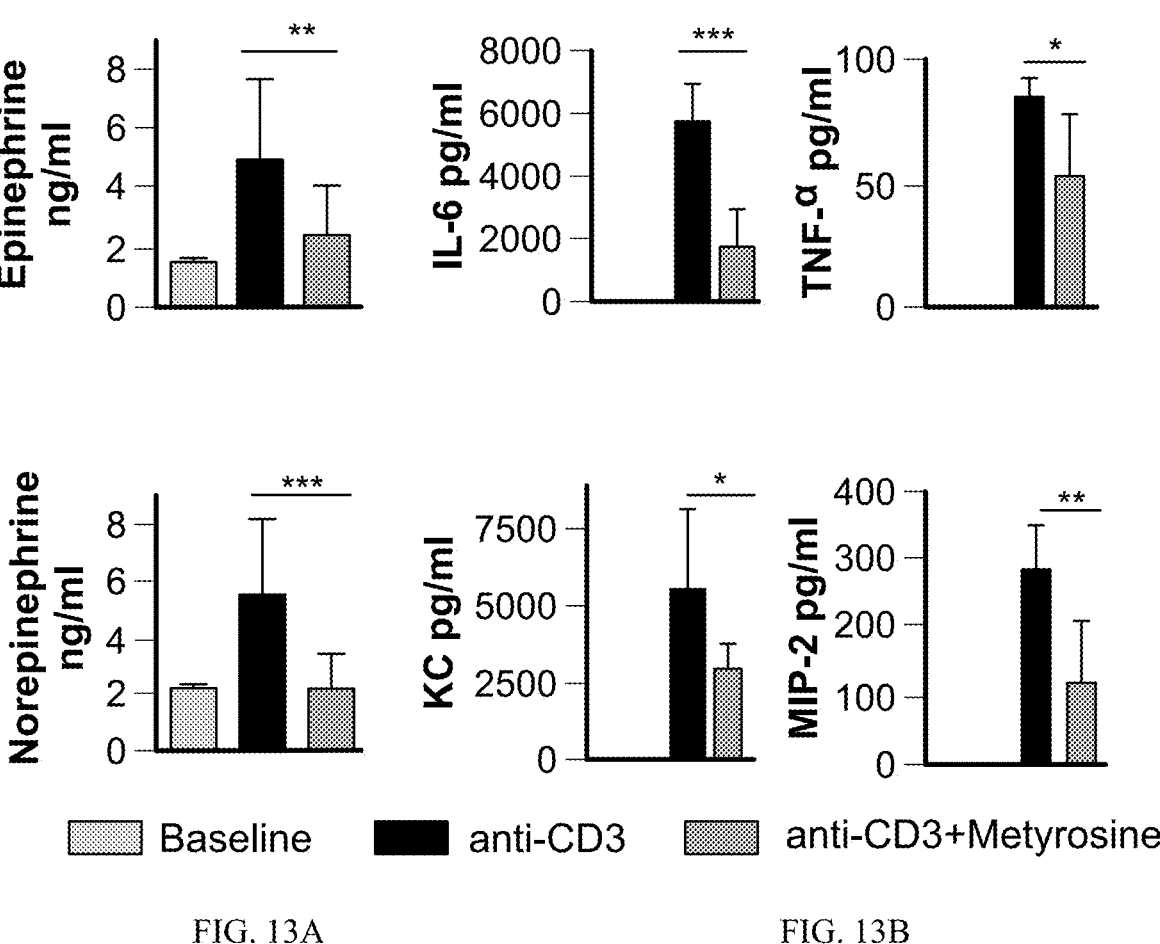
Figure 13C:
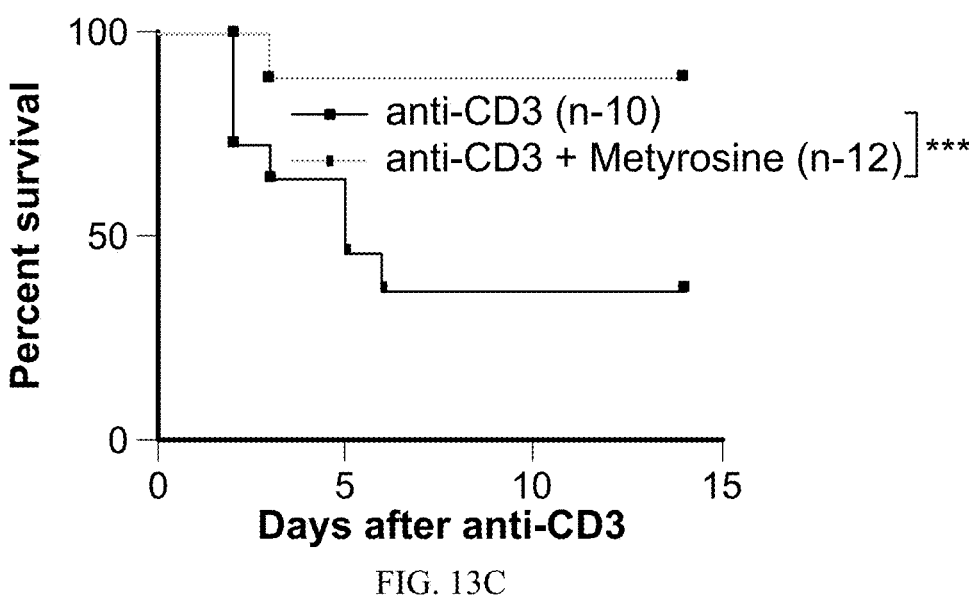
Figure 14A:
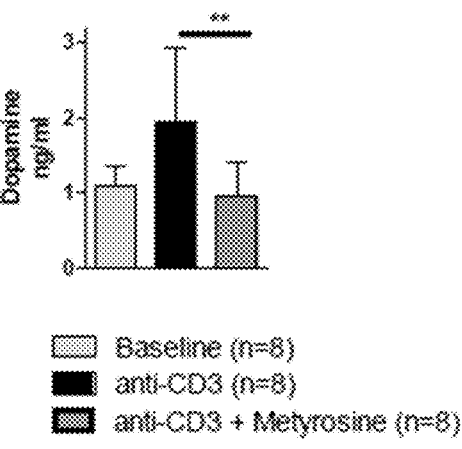
FIGS. 14A-14B show dopamine and additional cytokine data from the anti-CD3 experiments.
Figure 14B:
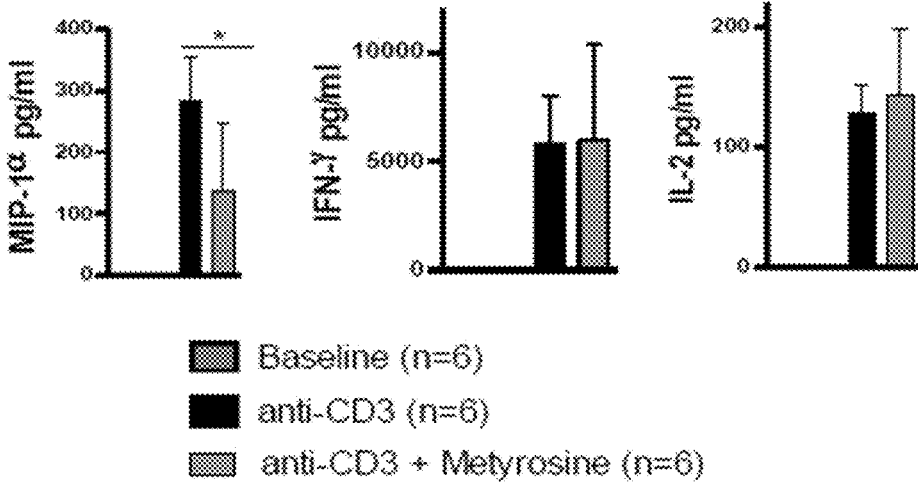

CRS is also observed after the administration of therapeutics not involving bacteria. For example, immunotherapeutic agents targeting CD3 molecules on the surface of T-cells is a promising treatment for autoimmune diseases and for the prevention of allograft rejection. However, the clinical implementation of such therapies (OKT3) has been hampered by CRS resulting from generalized T-cell activation (Chatenoud et al., 1990 Transplantation, 49:697; and Guglielmi et al., 2016 Expert Opin. Biolog. Ther., 16:841). To determine whether CRS unrelated to bacteria were accompanied by an increase in catecholamines, catecholamine levels were measured in mice at 24 and 48 hours after injection of an anti-CD3 antibody. The levels of epinephrine, norepinephrine and dopamine all increased substantially at both time points (FIG. 13A and FIG. 14A). Inflammatory cytokines also increased similar to that observed after infection with C. novyi-NT or induction of polymicrobial sepsis (FIGS. 12B and 12E). When mice were treated with metyrosine prior to administering anti-CD3 antibodies, the levels of circulating catecholamines were reduced to near normal levels. This decrease was associated with major reductions of the pro-inflammatory cytokines IL-6, TNF-α and KC among others (FIG. 13B and FIG. 14B). Most importantly, pre-treatment with metyrosine significantly impacted the survival of the mice: the majority of those treated only with anti-CD3 antibodies died, while eleven of the twelve mice pre-treated with metyrosine survived (FIG. 13C).

Figures 11A, 11B:
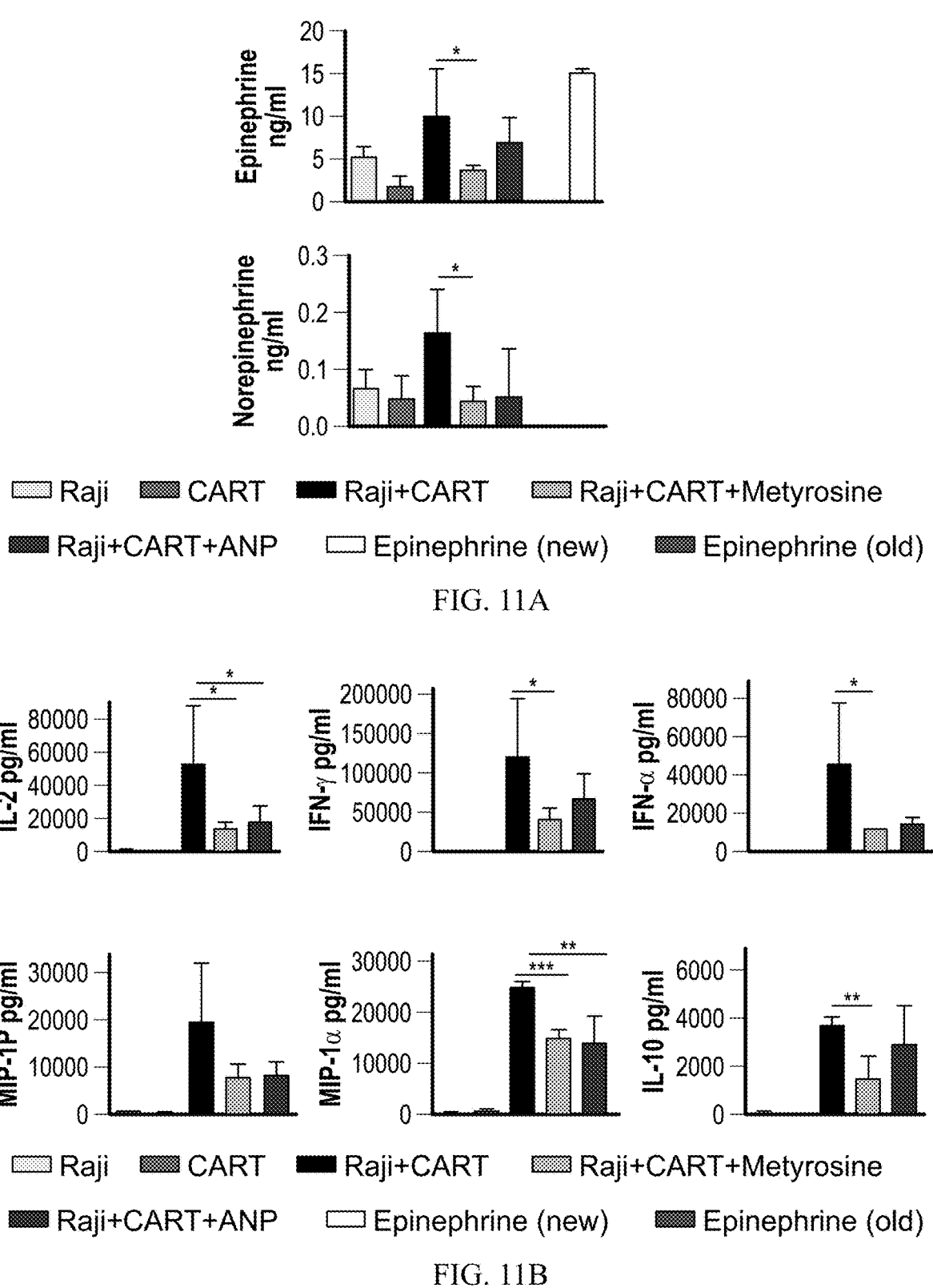
FIGS. 11A-11C show catecholamine and additional cytokine data from the CART19 experiments.
Figure 11C:
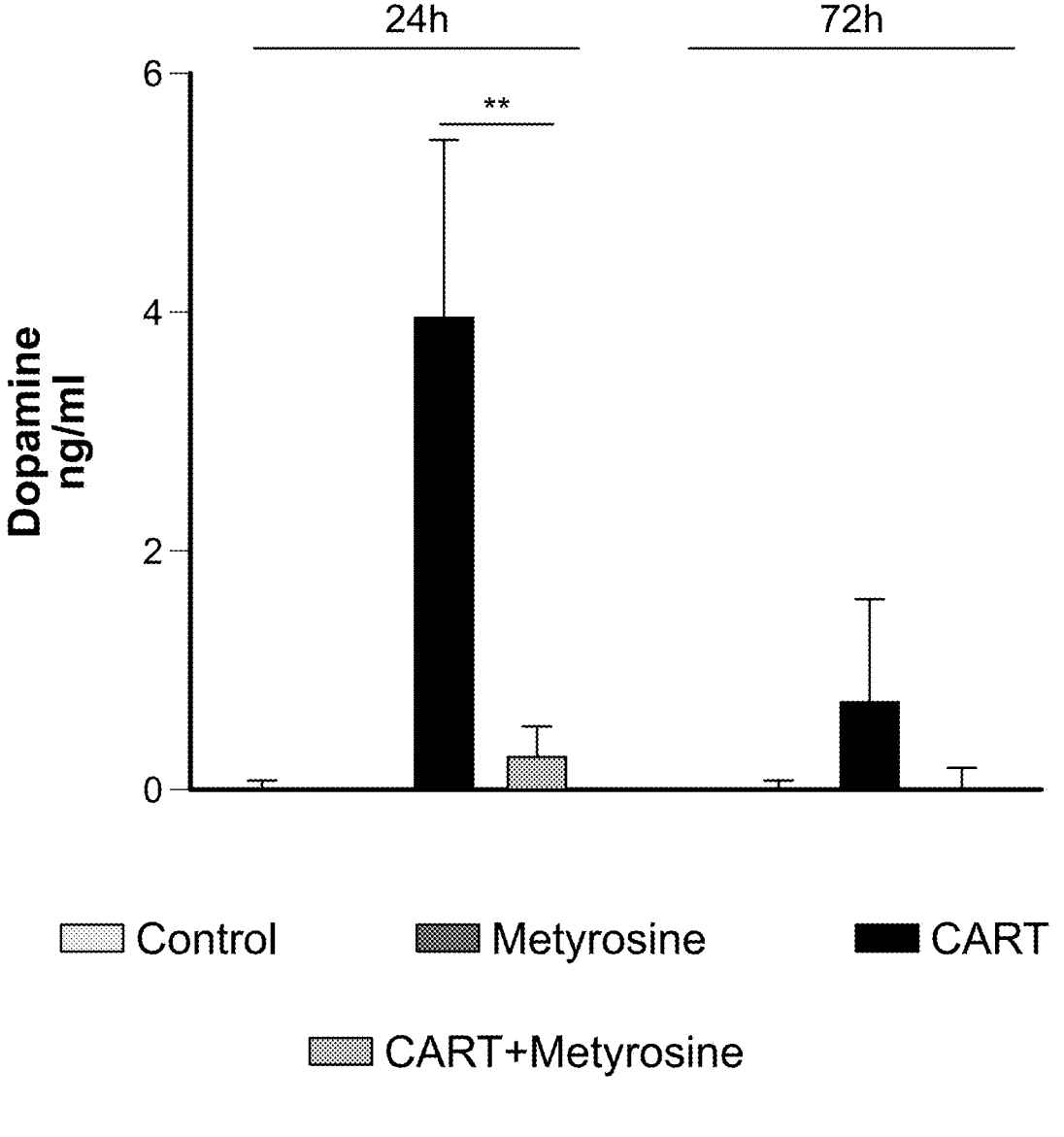
Figures 13D, 13E:
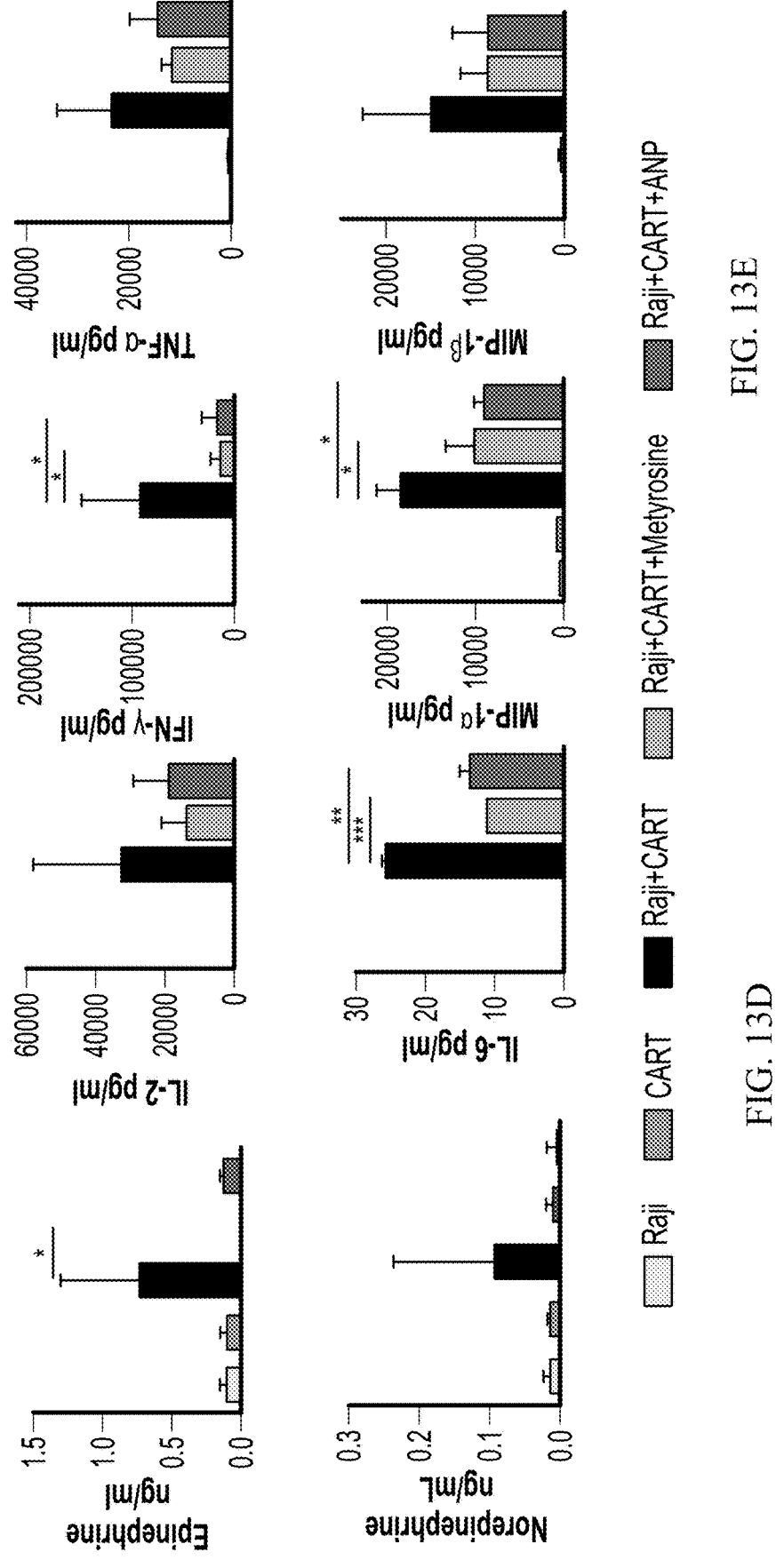
Figures 13F, 13G:
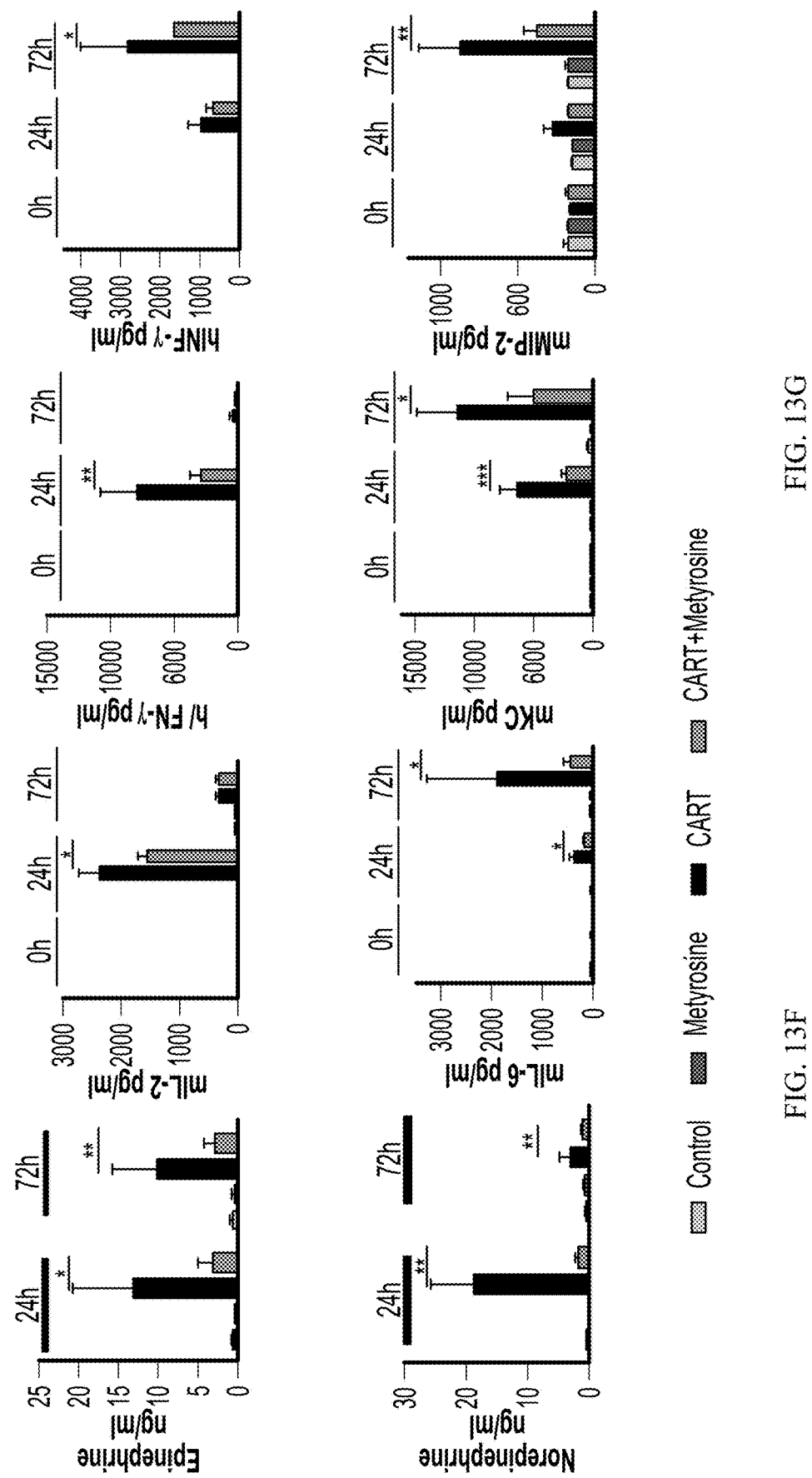

T-cell-mediated immunotherapies for cancer have recently been shown to achieve complete and durable tumor remissions in a subset of cancer patients. B cell malignancies are the most common tumor types to be effectively treated by such therapies; CD19-directed chimeric antigen receptor-modified T-cells (CARTs) have generated response rates of up to 95% in advanced cancers (Johnson et al., 2017 Cell Res., 27:38). Yet, the excessive and rapid tumor clearance as well as on-target, off-tumor activation of the engineered T-cells have been associated with dose-limiting toxicities and occasionally even lethal CRS (Teachey et al., 2016 Can. Disc., 6:664-79; Fitzgerald et al., 2017 Crit. Care Med., 45:e124-e31; Grupp et al., 2013 New Eng. J. Med., 368: 1509-18; Lee et al., 2014 Blood, 124:188-95; and Maude et al., 2014 New Eng. J. Med., 371:1507-17). To investigate whether CD19-directed CART (CART19) can generate and release significant catecholamines during tumor cell killing, the Burkitt's lymphoma-derived Raji cells were incubated with CART19. Levels of epinephrine and norepinephrine as well as various cytokines in culture supernatants increased substantially at 24 hours after exposure to CART19 (FIGS. 13D and 13E). The surge in catecholamines and cytokines was even more impressive when exogenous epinephrine was added to the cells (FIGS. 11A and 11B). Blockade of catecholamine synthesis with ANP and metyrosine significantly decreased the production of catecholamines and subsequent inflammatory responses as defined by cytokine production (FIGS. 13D and 13E; FIGS. 11A and 11B). To investigate the effect of catecholamine suppression on CRS in vivo, human Raji cells engrafted in the NSG™-SGM3 (NSGS) mice were allowed to grow for 6 days to establish a significant tumor burden before treatment with CART19. Blood obtained at 24 and 72 hours revealed peak levels of catecholamines and systemic release of various human and mouse cytokines, including IL-6, IFN-γ, TNF-α, KC, and MIP-2, which were significantly reduced when the mice had been pre-treated with metyrosine (FIGS. 13F and 13G; FIG. 11C).

Figure 15:
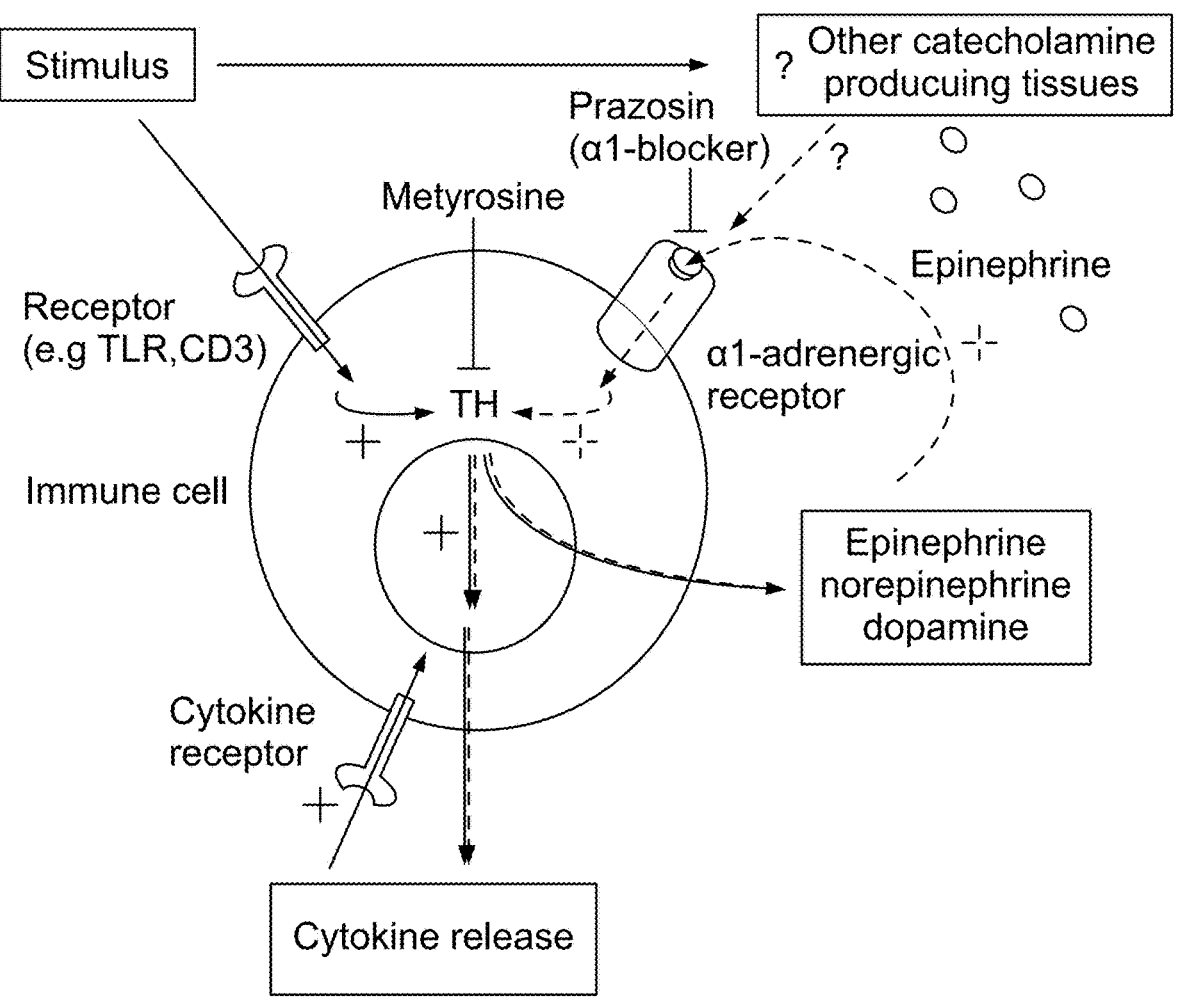
FIG. 15 contains a schematic showing how inhibition of the catecholamine pathway may reduce CRS. TLR, toll-like receptor.

A model explaining the reduced biotherapeutic toxicity resulting from pre-treatment with metyrosine is depicted in FIG. 15. Briefly, the data described herein suggest that catecholamines drive CRS via a self-amplifying feed-forward loop in immune cells such as macrophages and T-cells. Catecholamines secreted by immune cells and catecholamine-producing organs bind to the adrenergic receptors on the immune cells, stimulating more catecholamine and cytokine release, recruiting other inflammatory cells to the sites of inflammation, and eventually leading to organ system failure and death. Most importantly, this self-amplifying feed-forward loop has a central node—tyrosine hydroxylase—which, as demonstrated herein, can be exploited to interrupt the feed-forward loop, thereby modulating the inflammatory response.

Example 2: Reducing Mortality from Therapy-Induced Cytokine 1 Release Syndrome Via Disruption of a Self-Amplifying Catecholamine Synthesis Loop

Materials and Methods

Mice

All animal works were performed in accordance with protocols specified by the Johns Hopkins Animal Care and Use Committee (ACUC). For subcutaneous CT26 tumor implantation, LPS and CLP experiments, female C57BL/6 and BALB/C mice of 6-8 weeks were purchased from Harlan Laboratories. For anti-mCD3 treatment, female BALB/C mice of 5-6 months old were purchased form Harlan laboratories. For the CART19 treatment, NSG-SGM3 (NSGS) mice (Stock no. 013062) were purchased from the Jackson Laboratory.

LysMcre-Conditional TH Knockout Mice

LysMcre mice were purchased from Jackson 596 Laboratory (stock no. 004781), in which a nuclear-localized Cre recombinase was inserted into the first coding exon of the lysozyme 2 gene and expressed in the myeloid cell lineage (monocytes, mature macrophages and granulocytes). TH loxP/loxP (TH fl/fl) mice were as described elsewhere (see, e.g., Jackson et al., 2012 *J Neurosci* 32:9359-9368). By crossing these two strains, LysMcre: TH fl/fl mice (TH$^{\Delta LysM}$) were produced as experimental strain for LPS and anti-CD3 experiments and LysMcre: TH+/+ mice (TH+/+) were used as the Cre transgene control.

Chemicals and Reagents

Anti-mCD3 (145-2C11), anti-Ly6G (8C5) and anti-mIL6 receptor (15A7) antibodies were purchased from BioXcell. Anti-mTNFα antibody (R023) was purchased from Sino Biological and anti-mIL3 antibody (MP2-8F8) was purchased from BD Biosciences. α-methyl-D,L-p-tyrosine methyl ester hydrochloride (Santa Cruz Biotechnology, SC-219470) is a soluble from of α-methyl-tyrosine (metyrosine) that is converted to α-methyl-tyrosine in vivo, whereas the less soluble α-methyl-tyrosine was purchased from Sigma (120693). LPS from *Escherichia coli* 0111:B4 (L2630), (−)-epinephrine (E4250), dopamine (H8502), norepinephrine (A7256), prazosin (P7791), metoprolol (M5391) and human ANP (A1663) were purchased from Sigma. RX 821002 (1324) and ICI 118551 (0821) were purchased from Tocris.

Strain Engineering of *C. novyi*-NT

The site-specific knock-in of human ANP in *C. novyi*-NT employed the TargeTron Gene Knockout System (Sigma), which is based on the retrohoming mechanism of group II introns. The sequence of the human ANP cDNA was optimized for *Clostridium* codon usage as TCATTAAGAA-GATCTTCATGTTTTGGAGGAAGAATGGA-TAGAATAGGAGCTCAA TCAGGATTAGGATGTAATTCATTCAGATATTAA (SEQ ID NO:2) coding for 28 AA (SLRRSSCFGGRMDRI-GAQSGLGCNSFRY; SEQ ID NO:1). The synthesized sequence was cloned into the shuttle vector pMTL8325. The construct included the *C. novyi* PLC signal peptide sequence under the control of the *C. novyi* flagellin promoter. Subsequently, the MluI fragment of the construct was subcloned into the vector pAK001 (pMTL8325-pJIR750ai ReversepFla-153s-MCS-pThio-G1-ErmB) targeting the knock-in in the 153s site of *C. novyi*-NT genome. The *E. coli* CA434 strain containing the targeting construct was conjugated with *C. novyi*-NT and selected with polymyxin B/erythromycin (Sigma) under anaerobic condition. Colonies were selected and re-plated three times on non-selection plates and again on the erythromycin plate. Clones were tested first by PCR using EBS Universal and 153S-F primers. Positive clones were further tested by PCR with primers targeting the backbone of the vector to confirm the insert was integrated in *C. novyi* genome and with primers covering externally both sides of 153S to confirm the correct insertion. The propagation and sporulation of *C. novyi*-NT strains followed procedures described elsewhere (see, e.g., Bettegowda et al. 2006 *Nat Biotechnol* 24:1573-1580).

RNA Extraction and Quantitative PCR of *C. novyi*-NT Strains

RNA of germinated *C. novyi*-NT strains were extracted using RiboPure Bacterial RNA Purification Kit (Ambion) and transcribed with SuperScript IV RT Kit (Invitrogen) as described elsewhere (see, e.g., Bettegowda et al. 2006 *Nat Biotechnol* 24:1573-1580). Real-time PCR was performed using Maxima SYBR Green/ROX qPCR Master Mix (Thermo Fisher), targeting on the NT01CX1854 gene specific for geminating *C. novyi*-NT (see, e.g., Bettegowda et al. 2006 *Nat Biotechnol* 24:1573-1580).

ANP Measurement and cGMP Assay

ANP concentrations in the supernatant of ANP-*C. novyi*-642 NT culture and in mouse plasma were measured with an Elisa kit from Ray Biotech (EIAR-ANP-1) that recognizes both human and mouse ANP. ANP in the supernatant of ANP-*C. novyi*-NT culture were shown to have biological activity (see, e.g., Lofton et al., 1990 *Biochem Biophys Res Commun* 172:793-799). Briefly, bacterial supernatants were applied to cultured bovine aortic endothelial cells (BAOEC, Cell Applications Inc.) for 3 minutes. cGMP concentrations were then measured in BAOEC lysates by the Direct cGMP Elisa Kit from Enzo following the manufacture's instruction.

Subcutaneous Tumor Models and *C. novyi*-NT Therapy

The colon cancer cell line CT26 was injected subcutaneously into the right flank of six to eight weeks old female Balb/C mice as described elsewhere (see, e.g., Qiao et al. 2011 *Oncotarget* 2:59-68). Tumor sizes were measured with a caliper and calculated as ½*L*W*H as described elsewhere (see, e.g., Tomayko et al. 1989 *Cancer Chemother Pharmacol* 24:148-154). When tumors reached 600-900 mm$^3$ after about two weeks, $12\times10^6$ spores of *C. novyi*-NT or ANP-*C. novyi*-NT at $3\times10^6$/μl were injected intratumorally into 4 central parts of the tumor with a 32 G Hamilton syringe needle. The bacteria typical germinated in the tumors within 24 hours, turning them necrotic. Hydration of the mice was supported by daily subcutaneous injections of 500 μl saline. Human ANP (Sigma) was dissolved in saline, loaded in mini-osmotic pumps (ALZET) with a release rate of 12 μg/day and implanted subcutaneously in the back of mice 12 hours before the spore injection. Pumps loaded with saline served as controls. Metyrosine was dissolved in PBS and injected IP at 60 mg/kg/day for three days before the *C. novyi* injection to deplete catecholamines in storage. Two hours after the spore injection, 60 mg/kg of metyrosine was injected intraperitoneally (IP). For each of the next three days, IP injections of metyrosine at 30 mg/kg were administered. Control groups were injected with PBS at the same time points.

Immunohistochemistry

Immunostaining for CD11b was performed on formalin-fixed, paraffin embedded sections on a Ventana Discovery Ultra autostainer (Roche Diagnostics) by Ms. Sujayita Roy of JHU Oncology Tissue Services. Briefly, following dewaxing and rehydration on board, epitope retrieval was performed using Ventana Ultra CC1 buffer (#6414575001, Roche Diagnostics) at 96° C. for 64 minutes. Primary antibody, anti-CD11b (1:8000 dilution; catalog #ab133357, Abcam) was applied at 36° C. for 40 minutes. Primary antibodies were detected using an anti-rabbit HQ detection system (#7017936001 and 7017812001, Roche Diagnostics) followed by Chromomap DAB TIC detection kit (#5266645001, Roche Diagnostics), counterstaining with Mayer's hematoxylin, rehydration and mounting.

In Vitro Macrophage Experiments

Isolation of elicited macrophages from mouse peritoneum followed previously described procedures with minor modifications66. Four days prior to the harvest, 1 ml of 3% Brewer's thioglycollate medium (BD) was injected IP in female 2-3 months old BALB/c mice or 4-6 weeks old conditional TH knockout mice. Mice were euthanized by cervical dislocation and the skin of the belly was cut open without penetrating the muscle layer. Using a syringe with a 25 G needle, 5 ml of cold PBS containing 5 mM EDTA was injected carefully into the peritoneal cavity. After massaging gently for 1-2 minutes, a 1-ml syringe without needle was used to extract the peritoneal contents containing residential macrophages. Cells were centrifuged at 400 g for 10 minutes at 4° C., resuspended in DMEM/F12 medium supplemented with 1% FBS and antibiotics and distributed in 48-well plates at a concentration of $0.5 \times 10^6$ cells/well. After incubation at 37° C. for 2 hours, cells were rinsed three times with 0.5 ml media and then 250 μl of media was added to each well. Ten minutes before the addition of LPS 688 or epinephrine, metyrosine at 2 mM or ANP at 5 μg/ml was added to the cells. For stimulation, the cells were incubated for 24 hours with LPS at 50 μg/ml. An initial solution of 3 mg/ml (−)-epinephrine was made with 0.1 N HCl and subsequently diluted with PBS. To stimulate macrophages, they were exposed to epinephrine at 15 ng/ml for 24 hours at 37° C. After the incubation, supernatants were collected from the wells and mixed with 5 mM EDTA and 4 mM sodium metabisulfite for preservation of catecholamines and stored at −80° C. Control experiments showed that all detectable epinephrine was degraded after incubation in media for 24 hours at 37° C. Thus, any epinephrine identified in the media must have been secreted by cells in the last 24 hours prior to harvesting the media.

Human U937 cells were cultured in RPMI 1640 media with 5% FBS and antibiotics, and were differentiated to M1 macrophage-like cells by incubating with 20 nM phorbol 12-myristate 13-acetate (PMA, Sigma) for 24 hours and further culturing in RPMI 1640 media with 5% FBS and antibiotics for another 72 hours. The experiments with U937 were set up in the same way as described above with peritoneal macrophages. Ten minutes before the addition of LPS or epinephrine, metyrosine at 2 mM or ANP at 5 μg/ml was added to the cells. Cells were incubated for 24 hours with LPS at 1 μg/ml.

LPS Experiments in Mice

LPS from *Escherichia coli* 0111:B4 was formulated as a 10 mg/ml solution in water and stored in −80° C. In Balb/C mice, LPS was injected intraperitoneally at a lethal dose of 3.5 mg/kg. This lethal dose was found to cause 70-90% death rate and be optimal for demonstrating the protective effects of ANP and metyrosine. In experiments with catecholamine pumps, a sublethal dose with 15-35% death rate was optimized in Balb/C mice. In TH+/+ and $TH^{\Delta LysM}$ mice with C57BL/6 background, a lethal dose was optimized at 5 mg/kg. Human ANP (Sigma) was dissolved in saline, loaded in mini-osmotic pumps (ALZET) with a release rate of 12 μg/day and implanted subcutaneously in the back of mice 12 hours before the LPS injection. Mice implanted with pumps loaded with saline served as controls. Metyrosine was freshly dissolved in PBS and injected IP at the indicated doses for three days prior to the LPS treatment. One hour before the LPS injection, metyrosine was injected into the lower abdomen contralateral to the side of LPS injection. The control groups were injected with PBS. For the following 3 days, metyrosine was injected IP at reduced indicated doses. Hydration of mice was supported by daily subcutaneous injection of 0.5 ml saline.

CLP Experiments

CLP was performed as described elsewhere (see, e.g., Rittirsch et al., 2008 *Rev Immunol* 8:776-787). Briefly, 6-8 weeks old female C57BL/6 mice were anesthetized and following abdominal incision, the cecum was ligated at about ¼ the distance from the luminal entry to its tip. The ligated cecum was punctured through and through with a 22 G needle at ½ and ¾ the distance from the luminal entry to its tip. A small amount of the cecal content was gently pushed out of the four openings into the peritoneum. Subsequently, the abdominal muscles were sutured and the skin was closed with two staples. Five hundred microliters of saline were immediately injected subcutaneously to the mice. For the groups treated with antibiotics, imipenem (Sigma) was injected subcutaneously at 25 mg/kg starting from 20 hours after CLP, with a schedule of twice a day on day one and once a day thereafter for 10 days. Metyrosine was freshly dissolved in PBS and injected IP at 60 mg/kg/day for three days before the CLP. Twenty minutes before the CLP, metyrosine was injected at 60 mg/kg IP into the right side. The control groups were injected with PBS. For the following 4 days, metyrosine was injected at 30 mg/kg/day IP into the right side. Hydration of mice was supported by daily subcutaneous injection of 0.5 ml saline.

Anti-CD3 Treatment

For survival experiments, five to six-month old Female BALB/c mice were used because we observed that young mice treated with anti-CD3 antibodies underwent severe weight loss but did not consistently die, even at very high doses of the anti-CD3 antibody. Metyrosine was freshly dissolved in PBS and injected IP at 60 mg/kg/day for three days prior to injection of anti-CD3 antibodies. Various doses of anti-CD3 antibody were tested, and it was found that 125 μg/mouse resulted in the death of about half the mice; this was the dose chosen for further experiments. Thirty minutes before the IP injection of the anti-mouse CD3 antibody (BioXcell, 145-2C11), metyrosine was IP injected at 60 mg/kg into the contralateral side. A single additional dose of 30 mg/kg metyrosine was injected IP on the following day. Control groups were injected with PBS at the same times. For experiments with conditional TH knockout mice, 4-6 week-old LysMcre: TH fl/fl ($TH^{\Delta LysM}$) mice with C57BL/6 background were used and LysMcre: TH+/+ mice of the same age were used as control. In these experiments, 200 μg/mouse anti-mouse CD3 antibody was injected IP.

Human Anti-CD19 CART (hCART19) Cells and Untransduced T Cells

Human CD19scFv-CD28-4-1BB-CD3ζ CAR-T cells (PM-CAR1003) were purchased from Promab Biotechnologies and stored in liquid nitrogen upon delivery. The CAR construct includes a scFv derived from FMC63 anti-CD19 antibody, a hinge region and a transmembrane domain of CD28 in a third-generation CAR cassette. Generation of CAR-encoding lentivirus, isolation, expansion and transduction of human T cells followed procedures described elsewhere (see, e.g., Berahovich et al., 2017 *Front Biosci* 22:1644-1654). Cells were proliferated for two weeks in medium containing 300 IU/ml of hIL2. CART cells were used freshly upon defrosting or maintained less than 7 days in the CART medium consisting of AIM-V medium (GIBCO) supplemented with 5% FBS (Sigma) and penicillin-streptomycin (GIBCO), with the addition of 300 IU/ml of hIL2 (Peprotech).

Untransduced T cells were purchased from ASTARTE Biologics (#1017-37080C17, CD3+) and were used freshly upon defrosting or maintained less than 7 days in CART medium.

In Vitro Assays of hCART19 Cells

Raji, a human Burkitt's lymphoma cell line, was purchased from Sigma. In a 48 well plate, Raji cells were plated at $1 \times 10^5$/well and hCART19 cells or untransduced T cells were plated at $5 \times 10^5$/well in 275 µl of medium. A solution of 3 mg/ml (−)-epinephrine was made in 0.1 N HCl and subsequently diluted in PBS for use at a final concentration of 15 ng/ml. Five minutes before the Raji and CART cells with or without epinephrine were mixed, metyrosine at 2 mM or human ANP at 5 µg/ml was added and then the cells were incubated for 24 hours at 37° C. Control experiments showed that all detectable epinephrine was degraded after incubation in media for 24 hours at 37° C. Thus, any epinephrine identified in the media must have been secreted by cells in the last 24 hours prior to harvesting the media. Cycloheximide (CHX, Sigma) was added at 10 µg/ml to Raji and CART cells 30 minutes before they were mixed. After incubation, the cells were pelleted by centrifugation at 700 g and 4° C. for 5 minutes and the supernatants were collected and mixed with 5 mM EDTA and 4 mM sodium metabisulfite for preservation of catecholamines, then stored at −80° C. until analysis.

Treatment of Raji Tumor-Bearing Mice with hCART19 Cells

Six to eight weeks old female NSG-SGM3 (NSGS) mice (NOD.Cg-Prkdcscid Il2rgtm1WjlTg (CMV-IL3, CSF2, KITLG) 1Eav/MloySzJ, Stock #013062) were purchased from the Jackson Laboratory. Raji cells were transfected with a luciferase construct via lentivirus to create Raji-luc cells. NSGS is a triple transgenic strain expressing human IL3, GM-CSF and SCF combine the features of the highly immunodeficient NOD scid gamma (NSG) mouse. One day before the injection of Raji cells, mice were irradiated at a dose of 2 Gy in a CIXD Xstahl device. In high tumor burden experiments in FIG. 5, $10^6$ Raji-luc cells were injected IV via tail vein. Six days later, tumor loads were assessed using a Xenogen instrument and $15 \times 10^6$ hCART19 cells or untransduced T-cells were injected IV. In low tumor burden experiments in FIG. 6, $2 \times 10^5$ Raji-luc cells were injected IV via tail vein. Four days later, tumor loads were assessed using a Xenogen instrument and $15 \times 10^6$ hCART19 cells were injected IV. Metyrosine was injected IP at 60 mg/kg/day for three days before the hCART19 injection. On the day of CART19 injection, a fourth dose of 60 mg/kg was given IP and the mice were subsequently injected four more times at daily intervals at 30 mg/kg.

Mouse Anti-CD19 CART Cells (mCART19) and Untransduced T Cells

Mouse CD19scFv-CD28-CD3ζ CAR (m1928z) construct with GFP in SFG retroviral vector was as described elsewhere (see, e.g., Davila et al., 2013 *PLoS One* 8:e61338).

The isolation, activation, and transduction of mouse T cells followed the procedure described elsewhere (see, e.g., Davila et al., 2013 *PLoS One* 8:e61338; and Lee et al., 2009 *Methods Mol Biol* 506:83-96). Briefly, the spleens were harvested from female C57BL/6 mice and T cells were enriched from splenocytes by passage over a nylon wool column (Polysciences, Warrington, PA). Mouse T cells were then activated with CD3/803 CD28 Dynabeads (Thermo Fisher) following the manufacturer's instructions and cultured in the presence of hIL2 at 30 IU/mL (R & D Systems). Retrovirus was produced by transfecting Phoenix-Eco packaging cells (ATCC) and spinoculations were done twice with retroviral supernatant. mCART19 cells were expanded for 10-14 days as described elsewhere (see, e.g., Lee et al., 2009 *Methods Mol Biol* 506:83-96). Untransduced T cells were produced following the same procedure without viral transduction.

Treating B Cell Acute Lymphoblastic Leukemia (B-ALL) with mCART19 in Immunocompetent Mice The Eµ-ALL cell line was derived from a lymphoid malignancy in an Eµ-myc transgenic mouse and upon IV injection, can develop B-ALL in C57BL/6 mice. The Eµ-ALL cells were co-cultured with feeder NIH-3T3 cells that were irradiated at 60 Gy, in RPMI 1640 media supplemented with 10% FBS, 0.05 mM 2-Mercaptoethanol and antibiotics. Eµ-ALL cells were transfected with luciferase via lentivirus. $2 \times 10^6$ Eµ-ALL cells were IV injected in female 6-8 week-old C57BL/6 mice via tail vein and after 6 days, mice were IP injected with cyclophosphamide (CPA) at 100 mg/kg for pre-conditioning as described elsewhere (see, e.g., Davila et al., 2013 *PLoS One* 8:e61338). One day after CPA treatment, $10 \times 10^6$ mCART19 cells were IV injected in the mice. Metyrosine was injected IP at 40 mg/kg/day for three days before the mCART19 injection. On the day of mCART19 injection, a fourth dose of 40 mg/kg was given IP and the mice were subsequently injected four more times at daily intervals at 30 mg/kg. One day before mCART19 injection, mini-osmotic pumps (ALZET) loaded with hANP with a release rate of 12 µg/day were implanted subcutaneously in the back of mice. Tumor load was monitored by Xenogen before and after mCART19 injection.

Measurement of Catecholamines and Cytokines in Mouse Plasma

Blood samples were collected into tubes containing 5 mM EDTA and 4 mM sodium metabisulfite after puncturing the facial vein or (terminally) by cardiac puncture. Subsequently, the samples were centrifuged and the plasmas were stored at −80° C. prior to analysis. Catecholamines (dopamine, norepinephrine and epinephrine) were measured using the 3-CAT Research ELISA kit from Labor Diagnostika Nord GmbH/Rocky Mountain Diagnostics. Cytokines were measured using Luminex assays based on Millipore Mouse and Human Cytokine/Chemokine panels or ELISA kits for mouse or human IL-6, TNF-α, MIP-1α, KC and IL-2 (R&D Systems) per manufacturer's instructions.

Results

Figure 16A:
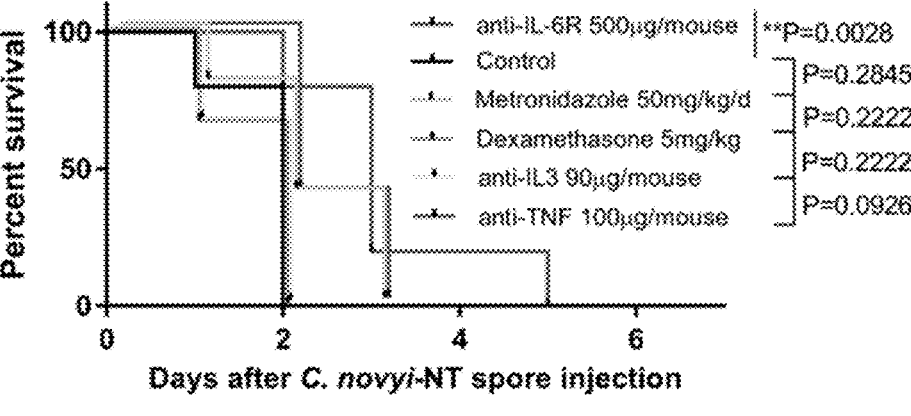
FIGS. 16A-16M show in vitro and in vivo studies of ANP-*C. novyi*-NT.

The study reported here began with experiments employing the anaerobic spore-forming bacterial strain *C. novyi*-NT to treat cancer (see, e.g., Staedtke et al., 2016 *Genes and Diseases* 3:144-152). These bacteria are strict anaerobes, and when spores are injected into animals or humans, bacteria germinate exclusively in hypoxic tumor tissues and can destroy them (see, e.g., Roberts et al. 2014 *Sci Transl Med* 6:249ra111). However, when very high doses of spores are injected into very large tumors, a massive infection occurs and the animals die within a few days with severe cytokine release due to a combination of tumor lysis and direct toxic effects of the bacteria (sepsis; see, e.g., Agrawal et al., 2004 *Proc Natl Acad Sci USA* 101:15172-15177; and Diaz Jr. et al., 2005 *Toxicol Sci* 88:562-575). To mitigate this dose-limiting toxicity, pre-treating mice, prior to injection of spores, with a variety of agents known to downregulate the inflammatory immune response was attempted (see, e.g., Grupp et al., 2013 *N Engl J Med* 368:1509-1518; Riedemann et al., 2003 *J Immunol* 170:503-507; Qiu et al., 2013 *Crit Care Med* 41:2419-2429; Weber et al., 2015 *Science* 347:1260-1265; and Annane et al., 2002 *JAMA* 288:862-871). Unfortunately, blocking antibodies to the receptors for the pro-inflammatory cytokines IL-6R or IL-3, and antibodies directed against circulating TNF-α, had limited effects on survival with only anti-IL-6R showing a significant but marginal improvement (FIG. 16A). Similarly, the antibiotic metronidazole and anti-inflammatory agent dexamethasone did not protect animals from sepsis, even when used at very high doses.

Figure 16B:
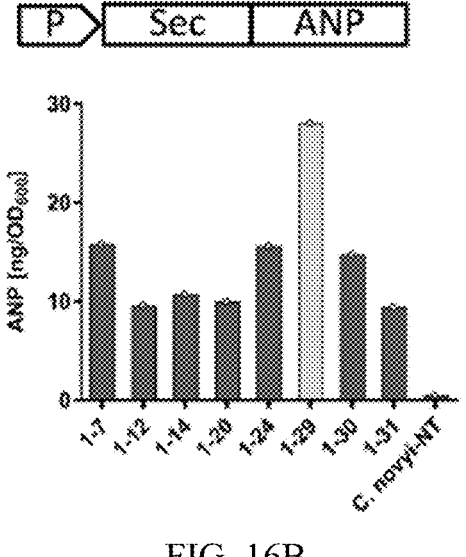
Figure 16C:
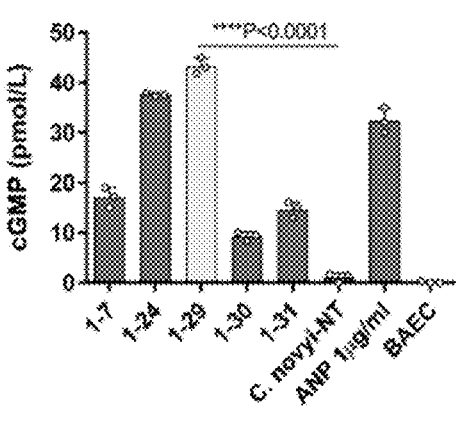
Figure 16D:
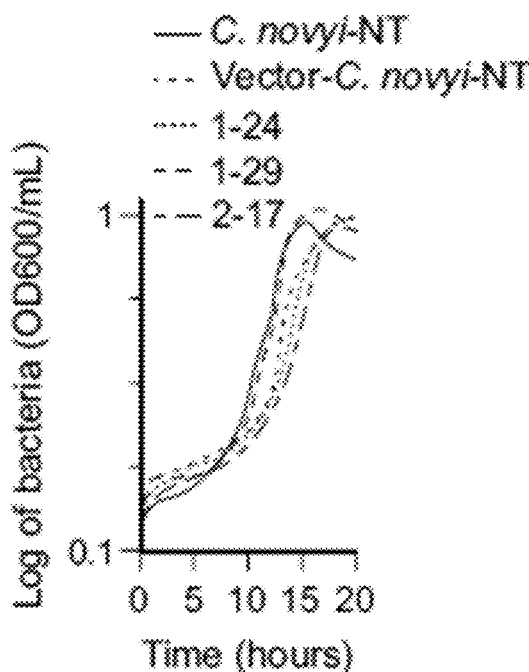

Engineering the bacteria to secrete various anti-inflammatory proteins that might mitigate the bacteria-associated toxicity was then attempted; atrial natriuretic peptide (ANP) was the only protein that proved successful in these experiments without compromising the efficacy. To see if ANP could protect mice from massive bacterial infections such as those caused by *C. novyi*-NT, *C. novyi*-NT was engineered to express and secrete ANP. A gene cassette encoding the ANP of 28-AA fused with a signal peptide at the N-terminus was optimized for *C. novyi* codon usage. This gene cassette was stably integrated into the *C. novyi*-NT genome using a method that combined the group II Intron targeting and bacterial conjugation (see Methods). Selected *C. novyi*-NT clones were characterized for ANP expression, biologic activity, and growth patterns in vitro (FIG. 16B-16D). The clone with the highest expression of ANP, called ANP-*C. novyi*-NT, was selected for further studies.

Figure 16E:
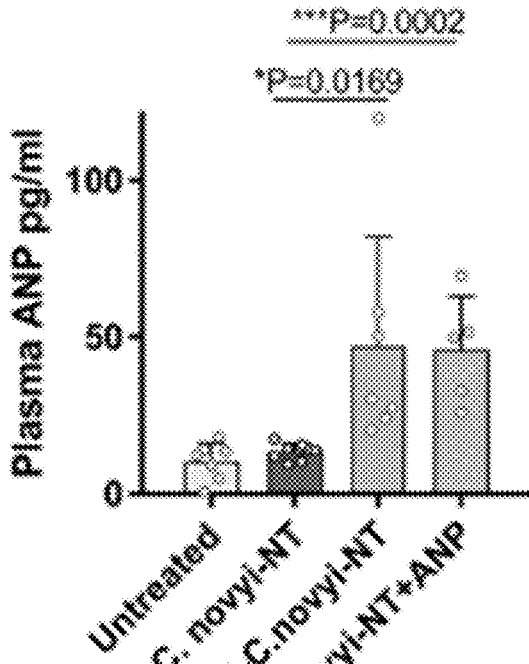
Figure 16F:
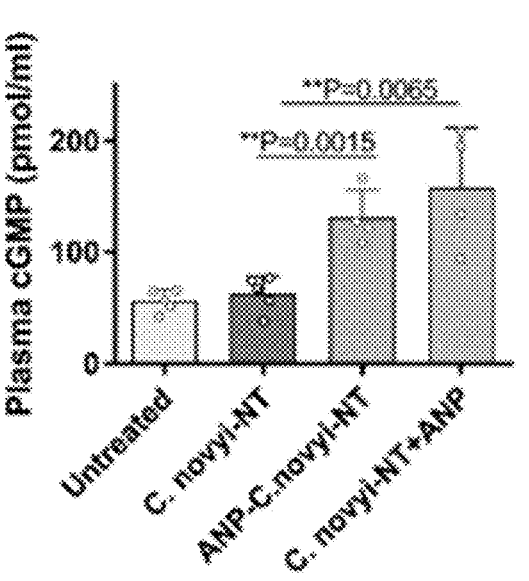
Figure 16G:
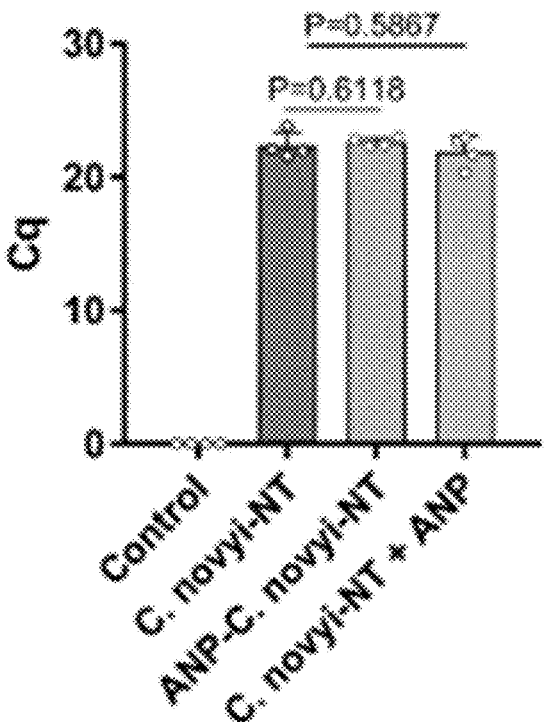
Figure 16H:
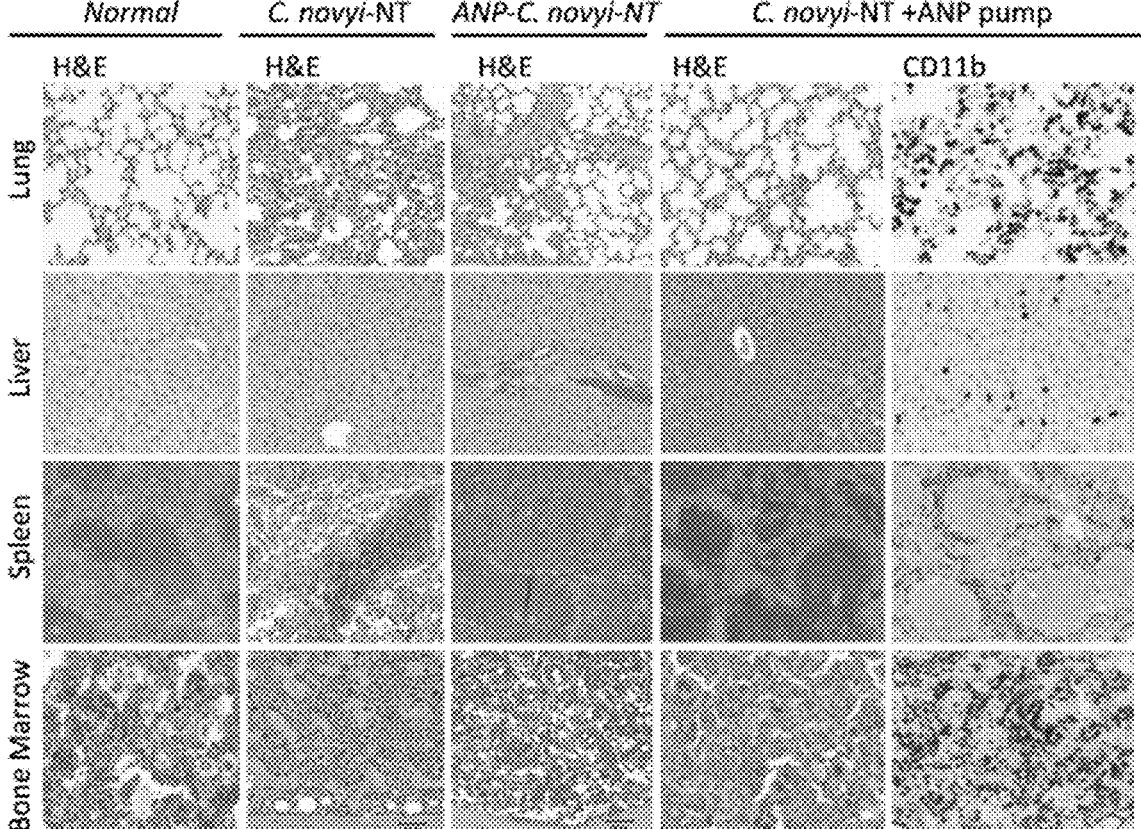
Figure 16I:
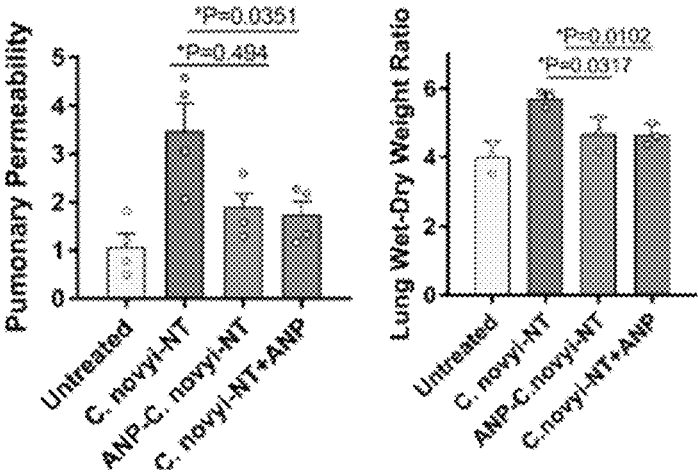

A single dose of ANP-*C. novyi*-NT spores injected into subcutaneously implanted CT26 colorectal tumors resulted in robust germination and cures. Levels of both plasma ANP and cGMP in mice injected with the ANP-*C. novyi*-NT strain were increased two to four times over that of mice injected with the parental *C. novyi*-NT strain (FIGS. 16E and 16F). Strikingly, at similar efficiencies of germination and proliferation between the two strains (FIG. 16G), ~80% of the animals receiving the ANP-*C. novyi*-NT strain survived while none of the mice treated with the parental *C. novyi*-NT strain alone did (FIG. 17A). Moreover, 84% of the surviving mice treated with ANP-*C. novyi*-NT strain had complete tumor regressions and long-term cures (FIG. 17A).

There was a noticeable reduction of tissue damage and inflammatory effects in the liver, spleen, and lungs of ANP-*C. novyi*-NT treated mice, as demonstrated by fewer infiltrating CD11b positive (CD11b+) myeloid cells in these organs and a less elevated pulmonary permeability compared to control animals that were given *C. novyi*-NT (FIG. 16H-17B). Those mice had evidence of severe inflammatory changes, many infiltrating CD11b+ myeloid cells in the liver and lungs correlating with a high pulmonary permeability index (FIG. 16H-17B).

Figure 16J:
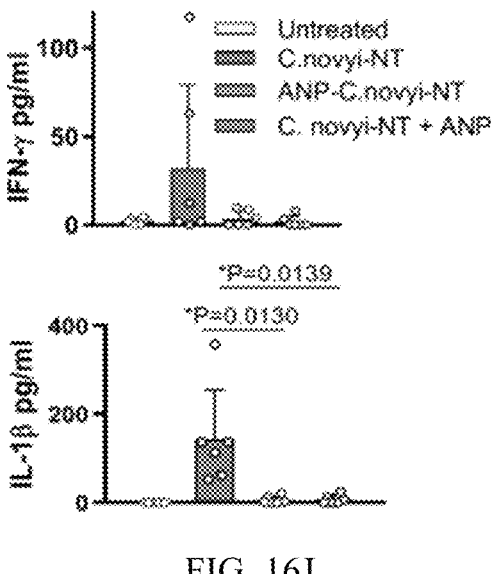
Figure 16M:
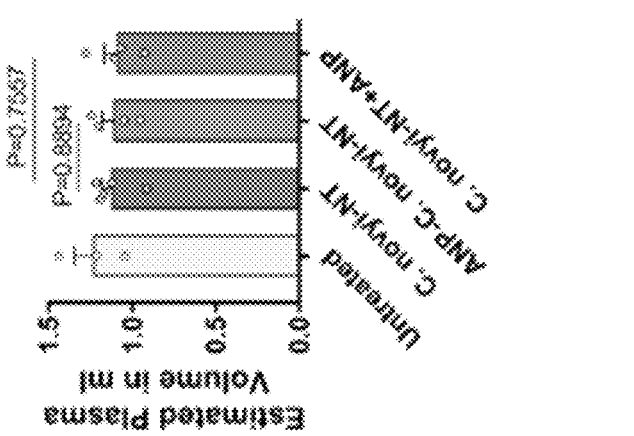
Figure 16L:
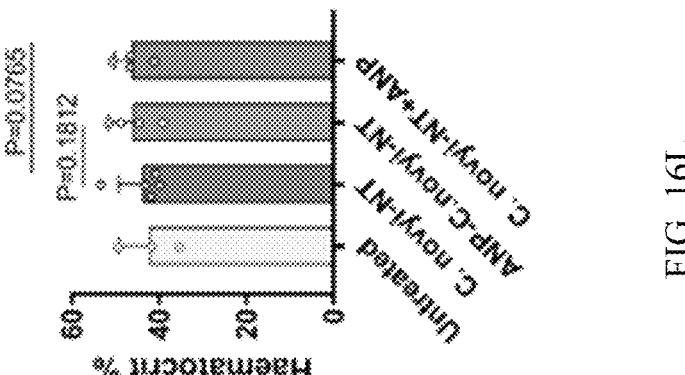
Figure 16K:
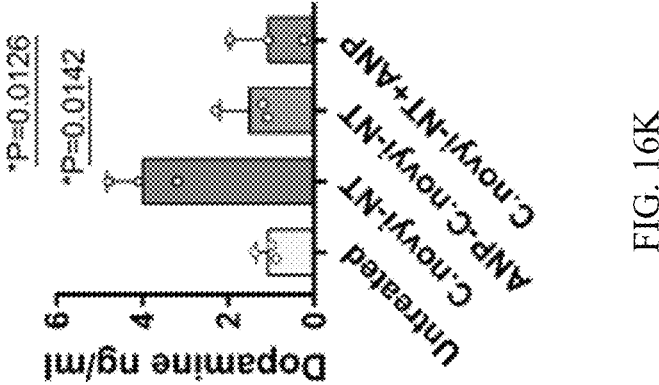

Likewise, mice injected with the ANP-*C. novyi*-NT strain had significantly less inflammatory cytokines and chemokines in their circulation than those treated with the parental strain. In particular, there were drastic reductions in cytokines and chemokines released from activated myeloid cells (IL-1β, IL-6, MIP-2, TNF-α), as well as chemoattractants (KC), and to a lesser degree in IFN-γ, MIP-1β, IL-12, IL-10 and MCP-1 (FIG. 17C). Interestingly, the cytokine reductions observed in ANP-*C. novyi*-NT treated mice were accompanied by significantly lower levels of circulating catecholamine compared to mice treated with *C. novyi*-NT (FIGS. 16K and 17D). This finding did not appear to be related to changes in the volume homeostasis as estimated plasma and volume hematocrit were similar in animals treated with *C. novyi*-NT and ANP-*C. novyi*-NT at 36 hours (FIGS. 16L and 16M). We next repeated the study in a different tumor type in another strain of mice. Using subcutaneous implants of the glioblastoma cell line GL-261 in C56Bl/6 mice, we found that 100% of mice treated with ANP-*C. novyi*-NT survived and had substantial tumor reductions, while nearly all of the mice treated with the parental strain of *C. novyi*-NT died within 72 hours of infection (FIG. 18A).

It was then sought to determine whether the protective effect was due to the expression of ANP rather than to some other unknown change in the engineered strain. For this purpose, mice were pre-treated with ANP released from an osmotic pump that was implanted 12 hours prior to injection with parental *C. novyi*-NT spores. The ANP delivered by this pump proved efficacious, with ~73% of the mice surviving, even though it did not have any effect on tumor colonization of *C. novyi*-NT (FIG. 17A). Of those that survived, all animals showed significant therapeutic responses: in ~80%, the tumor was completely eradicated and in the other 23%, a robust but not curative response was observed (FIG. 17A). Systemically delivered ANP also resulted in major reductions of circulating pro-inflammatory cytokines and catecholamines as well as tissue injury, similar to what was observed with ANP-*C. novyi*-NT (FIGS. 16J and 17C).

It was then sought to investigate the mechanism underlying the protective effects of ANP. BMS-345541 was administered to mice bearing large CT26 tumors prior to intratumoral injection with the parental strain of *C. novyi*-NT. However, unlike the case with ANP, there was no significant improvement in survival after pre-treatment with BMS-345541 (FIG. 18B). This result suggested that ANP inhibits the hyperinflammation resulting from *C. novyi*-NT infection through means in addition to, or other than, those involving the NF-κB pathway. In this regard, the changes to the catecholamine levels during the bacterial therapy were particularly intriguing and prompted us to investigate their relationship to the protective effects of ANP.

It was determined which catecholamines contributed to the CRS severity. For this purpose, subcutaneously implanted osmotic pumps that continuously released epinephrine, norepinephrine or dopamine into the circulation of mice treated with the potent inflammatory stimulant LPS were used. Mice co-treated with epinephrine had an earlier onset and exacerbated disease course, as demonstrated by increased mortality and elevated levels of catecholamines and IL-6, TNF-α, MIP-2, and KC, compared with that of LPS-only treated mice (FIG. 19A-19D). This effect was less pronounced in animals co-treated with norepinephrine and absent with dopamine. Furthermore, it was found that epinephrine can moderately stimulate cytokine release of IL6, KC and MIP-2, even though no effect on animal survival was observed (FIG. 19A-19D).

Next, it was investigated the catecholamine synthesis in mouse peritoneal macrophages. ANP was found to suppress the increased production of the macrophageal catecholamines (epinephrine, norepinephrine and dopamine) induced by LPS and this suppression correlated with a reduction in the cytokine levels of IL-6, TNF-α, 162 MIP-2, and KC compared to the controls (FIG. 20A-20B). Peritoneal macrophages treated with epinephrine alone also showed a mild but noticeable upregulation of the catecholamine and cytokine (IL-6, TNF-α, MIP-2, and KC) production, which was also suppressed by ANP (FIG. 19F-19G). Subsequently, epinephrine in combination with LPS vigorously augmented the inflammatory response and this amplification was inhibited by ANP (FIG. 20A-20B).

If the protective effects of ANP were due to its ability to interfere with catecholamine production, then inhibition of catecholamine synthesis should mimic the effects of ANP. α-methyltyrosine (metyrosine) is a specific inhibitor of catecholamine synthesis. Metyrosine binds to the active site of tyrosine hydroxylase (TH) and prevents binding of its natural substrate L-tyrosine, thereby inhibiting its conversion to L-dihydroxyphenylalanine (L-DOPA), the precursor of dopamine, norepinephrine and epinephrine. Pre-treatment with metyrosine greatly reduced the catecholamines produced by mouse macrophages exposed to LPS, epinephrine or the combination of both (FIG. 19F-19G; FIG. 20A-20B). Consistent with this, the cytokines released by macrophages were diminished by metyrosine pretreatment (FIG. 19F-19G; FIG. 20A-20B). Comparable results were obtained using human U937-derived macrophage cells (FIG. 21A).

To further confirm that the production of catecholamines from macrophages drives the inflammatory response, isolated peritoneal macrophages from mice with selective deletion of the gene encoding TH in LysM+ myeloid cells (LysMcre:TH fl/fl or THD$^{ΔLysM}$) were used. These mice showed significantly reduced TH expression in the harvested peritoneal macrophages (FIG. 21C) but not in lymphoid cell populations. Peritoneal macrophages with myeloid-specific deletion of TH showed a reduced secretion of catecholamines and inflammatory cytokines upon stimulation with LPS and epinephrine, which confirmed the role for autocrine catecholamine production in macrophages in the amplification of the inflammatory cascade (FIG. 21C-21E). Consistently, the LPS-induced production of catecholamines as well as inflammatory cytokines was abrogated in the THD$^{ΔLysM}$ mice that showed a survival benefit of 66%, while >65% of control mice died from the lethal toxicity (FIG. 20C-20E).

Metyrosine was found to have similar effects in vivo. When mice were pre-treated with metyrosine and then administered the same inflammatory stimulant, ~75% of the mice survived, whereas only 10% survived without metyrosine pre-treatment (FIG. 22). Both the levels of catecholamines and the levels of inflammatory cytokines were substantially reduced in the mice pre-treated with metyrosine (FIG. 22). The efficacy of metyrosine was dose-dependent; animal survival correlated with the degree of catecholamine depletion and cytokine reductions (FIG. 22). Metyrosine dosed at 20 mg/kg was ineffective. Serial plasma sampling of LPS-treated mice showed correlating inductions of catecholamines and cytokines in a time course of 3, 8 and 24 hours (FIG. 22). To document the generality of the effects of metyrosine, mice were treated with it prior to the induction of CRS by infection with parental *C. novyi*-NT. It was found that 85% of the mice pre-treated with metyrosine survived while only 8% of the mice in the control arm survived (FIG. 23). As predicted, catecholamines and cytokines were substantially reduced in animals pre-treated with metyrosine (FIG. 23).

To determine whether metyrosine could protect mice from bacterial infections in general, its effects were evaluated when administered prior to cecal ligation and puncture (CLP), a particularly challenging sepsis model. This puncture releases large numbers of enteric bacteria, including many species of gram-negative bacteria, into the peritoneum, causing polymicrobial peritoneal sepsis. Metyrosine significantly reduced the mortality from the polymicrobial peritoneal sepsis—22% of the mice survived the acute phase, while all animals died in the control arm (FIG. 23). However, when mice were pre-treated with metyrosine as well as with the β-lactam antibiotic imipenem at 20 hours after CLP, >⅔ of the mice survived CLP, while >90% of mice treated with the antibiotic alone died. This experiment highlights the fact that death from overwhelming bacterial infections is due to two factors: the bacteria themselves and the host reaction to the infection (i.e. CRS). To demonstrate that the detrimental host response was diminished by metyrosine pre-treatment, we measured the levels of circulating cytokines as described above. Multiple cytokines characteristic of sepsis or inflammation were substantially reduced by metyrosine after infection with *C. novyi*-NT or induction of polymicrobial peritonitis by CLP (FIG. 23). The expected effects of metyrosine on circulating catecholamines were also documented (FIG. 23).

To investigate which adrenergic receptor mediates the protective effect, adrenergic inhibitors prazosin, RX 821002, metoprolol, and ICI 118551 were used to block the respective α1, α2, β1 and 02-adrenoceptors in mice treated with LPS. Blockade of α1 adrenergic receptors substantially reduced mortality and suppressed the production of catecholamines and cytokines, achieving results similar to those of metyrosine, while blockade of α2, β1 and β2-adrenergic receptors did not reduce mortality (FIG. 24).

CRS is also observed after the administration of therapeutics not involving bacteria, and in particular with therapies that engage T cells, including anti-T cell antibodies. Injection of an anti-murine CD3 monoclonal antibody 145-2C11 into adult 5-6 months old BALB/c mice led to a massive transient T-cell activation with high levels of IL-6, TNF-α, KC and MIP-2 and even death, recapitulating the CRS observed in human patients (FIG. 25). To determine whether catecholamines may also drive non-bacterial, T-cell antibody-related CRS, catecholamine levels were first measured in mice 24 hours after injection of anti-CD3 antibody. Indeed, the levels of epinephrine, norepinephrine and dopamine all increased substantially, along with cytokine release (FIG. 25). However, when mice were treated with metyrosine prior to administering anti-CD3 antibody, the levels of circulating catecholamines were significantly reduced compared to the untreated controls. This decrease was associated with major reductions of the pro-inflammatory cytokines IL-6, TNF-α, KC, MIP-2 and MIP-1α, while IL-2 and IFN-γ were not significantly affected (FIG. 25). Most importantly, pre-treatment with metyrosine significantly improved the survival of mice: the majority of those treated only with anti-CD3 antibodies died, while twelve of the fifteen mice pre-treated with metyrosine survived (FIG. 25). These results were genetically substantiated in mice with myeloid-specific deletion of TH, resulting in an impaired ability to synthesize catecholamines. These mice (without metyrosine treatment) did not exhibit excessive cytokine release upon anti-CD3 exposure, mimicking wild-type mice pre-treated with metyrosine (FIG. 25).

To investigate whether CARTs can generate and release significant amounts of catecholamines during tumor cell killing, human Burkitt's lymphoma-derived CD19+ Raji cells were incubated with CD19-directed CARTs (hCART19) in vitro. For this purpose, primary donor T-cells were transduced with mouse FMC63 anti-CD19 scFv containing a CD28-based hinge region, transmembrane domain and costimulatory intracellular domains from CD28 and 4-1BB coupled with the CD3ζ activation domain (CD19scFv-CD28-4-1BB-CD3ζ), as detailed in Methods. In vitro, cytolysis of Raji cells by hCART19 resulted in substantially increased levels of epinephrine and norepinephrine as well as various cytokines such as IL-2, TNF-α, IFN-γ and MIP-1α in culture supernatants (FIG. 27A-27B). To demonstrate the epinephrine-driven autocrine induction, co-cultured Raji and hCART19 cells were treated with epinephrine, which resulted in an amplified catecholamine and cytokine response (FIG. 26A-26C).

To determine whether the autocrine epinephrine-induced production of catecholamines and cytokines takes place via new production rather than through the release of preformed catecholamines and cytokines, protein synthesis inhibitor cycloheximide (CHX) was used to treat the hCART19 cells during Raji exposure. It was found that the increase of catecholamines and cytokines (including TNF-α, MIP-1α, IFN-γ and GM-CSF) was greatly suppressed by treatment with CHX, suggesting that de novo protein synthesis is required for their increased levels (FIG. 26D-26E).

Untransduced T-cells did not result in any significant changes to the catecholamine or cytokine levels, unlike the situation with transduced (i.e., CART) cells (FIG. 27). Blockade of catecholamine synthesis with ANP or metyrosine significantly decreased the hCART19-induced catecholamines and subsequent inflammatory responses as defined by cytokine production (FIG. 27).

To investigate the effect of catecholamine suppression on CART19-elicited CRS in vivo, an NSG™-SGM3 (NSGS) xenograft model was employed. In contrast to NSG mice that do not develop CRS, NSGS mice that express human myelo-supportive cytokines (IL3, GM-CSF and SCF) promote enhanced human T-cell engraftment and expansion and enable better modeling of T-cell associated diseases including CRS. NSGS mice can partially cause CRS (see, e.g., Wunderlich et al., 2010 *Leukemia* 24:1785-1788; Sentman et al., 2016 *J Immunol* 197:4674-4685; Wunderlich et al., 2016 *JCI Insight* 1:e88181; and Gill et al., 2014 *Blood* 123:2343-2354).

Cohorts of NSGS mice were first irradiated at a sublethal dose. The mice were IV injected with $10^6$ Raji cells one day later. Raji tumors were allowed to grow for 6 days to the half time of the median survival of untreated mice to establish a condition in which CART cells would meet a high tumor burden and initiate lethal CRS within a few days, as is commonly observed in patients (FIG. 27 and FIG. 28). Blood obtained at 24 and 72 hours after hCART19 treatment revealed high levels of catecholamines (FIG. 27D and FIG. 28B), similar to what was observed after administration of anti-CD3 antibodies to T-cells in the experiments described above. This was accompanied by an acute inflammatory response, as defined by significant elevations of various human T-cell-produced cytokines in the circulation, including IL-2 (hIL-2), IFN-γ (hIFN-γ), and TNF-α (hTNF-α) as well as the release of endogenous host induced mouse cytokines IL-6, KC and MIP-2 consistent with CRS seen in human patients (FIG. 27E and FIG. 28C). hCART19-treated NSGS mice died 3-4 days after hCART19 injection with cytokine levels in the blood that proved lethal in the anti-CD3 experiments (FIG. 27C). However, mice pre-treated with metyrosine showed significantly lower catecholamine and cytokine levels (FIG. 27D-27E and FIG. 28B-28C), although mice eventually died with progressive lymphoma. Animals treated with the same amount of untransduced T-cells did not show any changes to survival, catecholamine or cytokine levels (FIG. 27 and FIG. 28).

The experiments described in FIG. 27-28 were designed to assess the effects of metyrosine on lethal toxicity associated with CRS following CART therapy. It was conceivable that the reduction of catecholamines and certain cytokines could interfere with the tumor response to CARTs, given the pleiotropic effects of catecholamines. To assess this issue, a low tumour burden model was employed to evaluate the impact of catecholamine blockage on the anti-tumor response (FIG. 29). hCART19 could eradicate tumors under these conditions (FIG. 29) but could not eradicate the larger tumors described in FIG. 27. Bioluminescent imaging (BLI) was used to quantify the tumor burden over time after CART injection (FIG. 29). The lymphoma burden diminished within one week after hCART19 treatment in mice treated with metyrosine or controls, but significantly more so in the mice treated with metyrosine. Tumors were eradicated, defined as BLI below $10^6$, in 6 out of 10 and 4 out of 10 animals treated with the combination of hCART19 plus metyrosine and measured on day 6 and 19, respectively, compared to 0 out of 10 in the CART19 group, correlating with a long-term survival of 40% of the metyrosine-treated hCART19 mice versus 0% in hCART19 only group (FIG. 29). Although none of the mice developed any clinical signs of toxicity, non-lethal elevation of catecholamines as well as human and mouse cytokines were still present in the hCART19 cohort and reduced in the metyrosine-treated hCART19 cohort (FIG. 29). These experiments were repeated with ANP, which also abrogated the hCART19-induced catecholamines and cytokine release in a similar way. Neither metyrosine nor ANP substantially interfered with in vivo CART cell expansion or tumor clearance (FIG. 28I and FIG. 29), and both were effective at preventing CRS, as evidenced by the significant reduction in the levels of mouse cytokines IL-6, KC and MIP-2 (FIG. 29).

Because available preclinical xenograft mouse models are poorly predictive of the clinical behavior of CART cells, a second syngeneic mouse model was applied to assess whether antitumor activity might be affected by CRS prophylaxis with metyrosine or ANP. For this aim, C57BL/6 mice were engrafted with Eμ-ALL cells that developed CD19-positive B-ALL. After verifying the establishment of the leukemic tumor burden, mice were infused with mouse CART19 (mCART19) cells directed against mouse CD19 and containing the costimulatory intracellular domain from CD28 coupled with the CD3ζ activation domain (m1928z), as detailed in Methods. Mice undergoing pharmacologic prophylaxis with ANP or metyrosine matched the therapeutic efficacy of control mice treated with mCART19 alone while the catecholamine and cytokine release was reduced (FIG. 30) thereby confirming that either drug may prevent CRS while maintaining intact antitumor efficacy. A model explaining the reduced toxicity resulting from pre-treatment with metyrosine is depicted in FIG. 15. Briefly, these data suggest that catecholamines triggers CRS via a self-amplifying feed-forward loop in immune cells such as macrophages whereas myeloid-specific deletion of TH was protective.

This study provides evidence that catecholamines are drivers for CRS and that enhanced production of catecholamines increases the intensity of the inflammatory response in bacterial and non-bacterial causes. Blockage of catecholamine synthesis reduced lethal cytokine levels into a non-lethal range that not only ensured animal survival but also was still sufficient enough to allow effective tumor eradication.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

---

What is claimed is:

1. A method for treating a mammal having cytokine release syndrome (CRS), wherein said method comprises administering a catecholamine inhibitor to said mammal.

2. The method of claim 1, wherein said catecholamine is selected from the group consisting of epinephrine, norepinephrine, dopamine, and combinations thereof.

3. The method of claim 2, wherein said catecholamine is epinephrine.

4. The method of claim 1, wherein said mammal is a human.

5. The method of claim 1, wherein said catecholamine inhibitor comprises a tyrosine hydroxylase inhibitor, and wherein said tyrosine hydroxylase inhibitor is metyrosine.

6. The method of claim 1, wherein said catecholamine inhibitor comprises a natriuretic peptide selected from the group consisting of atrial natriuretic peptide (ANP), brain natriuretic peptide (BNP), C-type natriuretic peptide (CNP), and dendroaspis natriuretic peptide (DNP).

7. The method of claim 6, wherein said natriuretic peptide is ANP, and wherein said ANP comprises SEQ ID NO:1.

8. The method of claim 1, wherein said catecholamine inhibitor comprises an agent that can accelerate catecholamine degradation, and wherein said agent that can accelerate catecholamine degradation is a monoamine oxidase A activator or a catechol-O-methyltransferase (COMT) activator.

9. The method of claim 1, wherein said catecholamine inhibitor comprises an agent that can block catecholamine release, wherein said agent that can block catecholamine release is gabapentin.

10. The method of claim 1, wherein said catecholamine inhibitor comprises an agent that can block the α1 adrenergic receptor, wherein said agent that can block the α1 adrenergic receptor is prazosin.

11. The method of claim 1, wherein said catecholamine inhibitor comprises both a natriuretic peptide and a hydroxylase inhibitor, wherein said natriuretic peptide is atrial natriuretic peptide (ANP) and wherein said tyrosine hydroxylase inhibitor is metyrosine.

12. The method of claim 1, wherein said CRS is associated with sepsis.

13. The method of claim 1, wherein said CRS is associated with an immunotherapy.

14. The method of claim 13, wherein said immunotherapy is selected from the group consisting of orthoclone OKT3, muromonab-CD3, rituximab, alemtuzumab, tosituzumab, CP-870,893, LO-CD2a/BTI-322, TGN1412, tisagenlecleucel, axicabtagene ciloleucel, bi-specific T-cell engagers (BiTEs), adoptive T-cell therapy, dendritic cell therapy, interferon therapy, interleukin therapy, bacterial therapy, and viral therapy.

15. The method of claim 13, wherein said immunotherapy is a cancer immunotherapy.

* * * * *

SEQUENCE LISTING

```
Sequence total quantity: 2
SEQ ID NO: 1            moltype = AA  length = 28
FEATURE                 Location/Qualifiers
source                  1..28
                        mol_type = protein
                        organism = Homo sapiens
SEQUENCE: 1
SLRRSSCFGG RMDRIGAQSG LGCNSFRY                                28

SEQ ID NO: 2            moltype = DNA  length = 87
FEATURE                 Location/Qualifiers
source                  1..87
                        mol_type = other DNA
                        organism = Homo sapiens
SEQUENCE: 2
tcattaagaa gatcttcatg ttttggagga agaatggata gaataggagc tcaatcagga  60
ttaggatgta attcattcag atattaa                                      87
```